US012734173B2

(12) United States Patent
Shilatifard et al.

(10) Patent No.: US 12,734,173 B2
(45) Date of Patent: Sep. 15, 2026

(54) USE OF NUCLEOTIDE SYNTHESIS INHIBITORS FOR TARGETED THERAPY IN MLL3/4 COMPASS MUTANT CANCER

(71) Applicant: Northwestern University, Evanston, IL (US)

(72) Inventors: Ali Shilatifard, Chicago, IL (US); Zibo Zhao, Chicago, IL (US)

(73) Assignee: Northwestern University, Evanston, IL (US)

( * ) Notice: Subject to any disclaimer, the term of this patent is extended or adjusted under 35 U.S.C. 154(b) by 484 days.

(21) Appl. No.: 18/328,011

(22) Filed: Jun. 2, 2023

(65) Prior Publication Data

US 2023/0390297 A1 Dec. 7, 2023

Related U.S. Application Data

(60) Provisional application No. 63/348,333, filed on Jun. 2, 2022.

(51) Int. Cl.
*A61K 31/519* (2006.01)
*A61K 31/42* (2006.01)
*A61K 31/4375* (2006.01)
*A61P 35/00* (2006.01)

(52) U.S. Cl.
CPC ............ *A61K 31/519* (2013.01); *A61K 31/42* (2013.01); *A61K 31/4375* (2013.01); *A61P 35/00* (2018.01)

(58) Field of Classification Search
CPC .............................. A61K 31/519; A61P 35/00
See application file for complete search history.

(56) References Cited

U.S. PATENT DOCUMENTS

2021/0145855 A1 5/2021 Ahmed et al.

FOREIGN PATENT DOCUMENTS

| | | | | |
|---|---|---|---|---|
| GB | 2552269 | A | 1/2018 | |
| WO | 2009014642 | A1 | 1/2009 | |
| WO | 2014018862 | A1 | 1/2014 | |
| WO | WO-2018222831 | A1 * | 12/2018 | ............. A61P 35/00 |
| WO | 2022226312 | A1 | 10/2022 | |

OTHER PUBLICATIONS

Alam, H., et al., KMT2D Deficiency Impairs Super-Enhancers to Confer a Glycolytic Vulnerability in Lung Cancer. Cancer Cell 37, 599-617 e597 (2020).
Anders, S., P. T. Pyl, W. Huber, HTSeq—a Python framework to work with high-throughput sequencing data. Bioinformatics 31, 166-169 (2015).
Andrews, S., FastQC: a quality control tool for high throughput sequence data. Available online. http://www.bioinformatics.babraham.ac.uk/projects/fastqc (2010).
Ashokkumar, D., et al., MLL4 is required after implantation, whereas MLL3 becomes essential during late gestation. Development 147, (2020).
Bolger, A. M., M. Lohse, B. Usadel, Trimmomatic: a flexible trimmer for Illumina sequence data. Bioinformatics 30, 2114-2120 (2014).
Cao, K., et al., An MII4/COMPASS-Lsd1 epigenetic axis governs enhancer function and pluripotency transition in embryonic stem cells. Sci Adv 4, eaap8747 (2018).
Cao, K., et al., SET1A/COMPASS and shadow enhancers in the regulation of homeotic gene expression. Genes Dev 31, 787-801 (2017).
Cheon, C. K., et al., Identification of KMT2D and KDM6A mutations by exome sequencing in Korean patients with Kabuki syndrome. Journal of human genetics 59, 321-325 (2014).
Cocciadiferro, D., et al., Dissecting KMT2D missense mutations in Kabuki syndrome patients. Hum Mol Genet 27, 3651-3668 (2018).
Deberardinis, R. J., N. S. Chandel, We need to talk about the Warburg effect. Nat Metab 2, 127-129 (2020).
Doench, J. G., et al., Optimized sgRNA design to maximize activity and minimize off-target effects of CRISPR-Cas9. Nat Biotechnol 34, 184-191 (2016).
Fantini, D., et al., A Carcinogen-induced mouse model recapitulates the molecular alterations of human muscle invasive bladder cancer. Oncogene 37, 1911-1925 (2018).
Gibcus J. H. et al., A pathway for mitotic chromosome formation. Science 359, (2018).
Grasso, C. S., et al., The mutational landscape of lethal castration-resistant prostate cancer. Nature 487, 239-243 (2012).
Gui, Y., et al., Frequent mutations of chromatin remodeling genes in transitional cell carcinoma of the bladder. Nat Genet 43, 875-878 (2011).
Hashizume R. et al., Pharmacologic inhibition of histone demethylation as a therapy for pediatric brainstem glioma. Nat Med 20, 1394-1396 (2014).
Herz, H. M., D. Hu, A. Shilatifard, Enhancer malfunction in cancer. Mol Cell 53, 859-866 (2014).
Herz, H. M., et al., Enhancer-associated H3K4 monomethylation by Trithorax-related, the Drosophila homolog of mammalian MII3/MII4. Genes Dev 26, 2604-2620 (2012).
Hu, D., et al., The MLL3/MLL4 branches of the COMPASS family function as major histone H3K4 monomethylases at enhancers. Mol Cell Biol 33, 4745-4754 (2013).
Jang, C., L. Chen, J. D. Rabinowitz, Metabolomics and Isotope Tracing. Cell 173, 822-837 (2018).
Jones, D. T., et al., Dissecting the genomic complexity underlying medulloblastoma. Nature 488, 100-105 (2012).
Kalu, N. N., et al., Comprehensive pharmacogenomic profiling of human papillomavirus-positive and -negative squamous cell carcinoma identifies sensitivity to aurora kinase inhibition in KMT2D mutants. Cancer Lett 431, 64-72 (2018).
Kim, D., et al., TopHat2: accurate alignment of transcriptomes in the presence of insertions, deletions and gene fusions. Genome biology 14, R36 (2013).

(Continued)

*Primary Examiner* — Sarah Pihonak
*Assistant Examiner* — Mikhail O'donnel Robinson
(74) *Attorney, Agent, or Firm* — Quarles & Brady LLP

(57) ABSTRACT

Disclosed herein are methods and compositions for treating a subject comprising the administration of an effective amount of a nucleotide synthesis inhibitor to a subject in need of treatment for a MLL3/4 COMPASS deficient cancer or a MLL3/4 loss of function mutation.

23 Claims, 66 Drawing Sheets

Specification includes a Sequence Listing.

(56) References Cited

OTHER PUBLICATIONS

Kim, J. H., et al., UTX and MLL4 coordinately regulate transcriptional programs for cell proliferation and invasiveness in breast cancer cells. Cancer Res 74, 1705-1717 (2014).
Langmead, B., C. Trapnell, M. Pop, S. L. Salzberg, Ultrafast and memory-efficient alignment of short DNA sequences to the human genome. Genome biology 10, R25 (2009).
Lawrence, M., et al., Software for computing and annotating genomic ranges. PLoS computational biology 9, e1003118 (2013).
Lawson, A. R. J., et al., Extensive heterogeneity in somatic mutation and selection in the human bladder. Science 370, 75-82 (2020).
Li, R., et al., Macroscopic somatic clonal expansion in morphologically normal human urothelium. Science 370, 82-89 (2020).
Li, W., et al., MAGeCK enables robust identification of essential genes from genome-scale CRISPR/Cas9 knockout screens. Genome Biol 15, 554 (2014).
Li, W., et al., Quality control, modeling, and visualization of CRISPR screens with MAGeCK-VISPR. Genome Biol 16, 281 (2015).
Liu, Y. L., et al., Structural insights into trans-histone regulation of H3K4 methylation by unique histone H4 binding of MLL3/4. Nature Communications 10, (2019).
Lohr, J. G., et al., Discovery and prioritization of somatic mutations in diffuse large B-cell lymphoma (DLBCL) by whole-exome sequencing. Proc Natl Acad Sci U S A 109, 3879-3884 (2012).
Maitituoheti, M., et al., Enhancer Reprogramming Confers Dependence on Glycolysis and IGF Signaling in KMT2D Mutant Melanoma. Cell Rep 33, 108293 (2020).
Martincorena, I., et al., Somatic mutant clones colonize the human esophagus with age. Science 362, 911-917 (2018).
Meeks, Joshua J., and Ali Shilatifard. "Multiple roles for the MLL/COMPASS family in the epigenetic regulation of gene expression and in cancer." Annual Review of Cancer Biology 1 (2017): 425-446.
Moore, L., et al., The mutational landscape of normal human endometrial epithelium. Nature 580, 640-646 (2020).
Morgan, M. A., A. Shilatifard, Chromatin signatures of cancer. Genes Dev 29, 238-249 (2015).
Morin, R. D., et al., Frequent mutation of histone-modifying genes in non-Hodgkin lymphoma. Nature 476, 298-303 (2011).
Ng, S. B., et al., Exome sequencing identifies the cause of a mendelian disorder. Nat Genet 42, 30-35 (2010).
Pacelli, C., et al., Loss of Function of the Gene Encoding the Histone Methyltransferase KMT2D Leads to Deregulation of Mitochondrial Respiration. Cells 9, (2020).
Parsons, D. W., et al., The genetic landscape of the childhood cancer medulloblastoma. Science 331, 435-439 (2011).
Pasqualucci, L., et al., Analysis of the coding genome of diffuse large B-cell lymphoma. Nat Genet 43, 830-837 (2011).
Pugh, T. J., et al., Medulloblastoma exome sequencing uncovers subtype-specific somatic mutations. Nature 488, 106-110 (2012).
Quinlan, A. R., I. M. Hall, BEDTools: a flexible suite of utilities for comparing genomic.
Rickels, R., et al., A small UTX stabilization domain of Trr is conserved within mammalian MLL3-4/COMPASS and is sufficient to rescue loss of viability in null animals. Genes Dev, (2020).
Rickels, R., et al., Histone H3K4 monomethylation catalyzed by Trr and mammalian COMPASS-like proteins at enhancers is dispensable for development and viability. Nat Genet 49, 1647-1653 (2017).
Robinson, M. D., D. J. Mccarthy, G. K. Smyth, edgeR: a Bioconductor package for differential expression analysis of digital gene expression data. Bioinformatics 26, 139-140 (2010).
Shen, L., N. Shao, X. Liu, E. Nestler, ngs.plot: Quick mining and visualization of next-generation sequencing data by integrating genomic databases. BMC Genomics 15, 284 (2014).
Stine, Z. E., Z. T. Schug, J. M. Salvino, C. V. Dang, Targeting cancer metabolism in the era of precision oncology. Nat Rev Drug Discov 21, 141-162 (2022).
Szczepanski A. P., et al., ASXL3 bridges BRD4 to BAP1 complex and governs enhancer activity in small cell lung cancer. Genome Med 12, 63 (2020).
Sze, C. C., A. Shilatifard, MLL3/MLL4/COMPASS Family on Epigenetic Regulation of Enhancer Function and Cancer. Cold Spring Harb Perspect Med 6, (2016).
Vander Heiden, M. G., R. J. DeBerardinis, Understanding the Intersections between Metabolism and Cancer Biology. Cell 168, 657-669 (2017).
Villa, E., E. S. Ali, U. Sahu, I. Ben-Sahra, Cancer Cells Tune the Signaling Pathways to Empower de Novo Synthesis of Nucleotides. Cancers (Basel) 11, (2019).
Wang, B., et al., Integrative analysis of pooled CRISPR genetic screens using MAGeCKFlute. Nat Protoc 14, 756-780 (2019).
Wang, C., et al., Enhancer priming by H3K4 methyltransferase MLL4 controls cell fate transition. Proc Natl Acad Sci U S A 113, 11871-11876 (2016).
Wang, G., et al., CRISPR-GEMM Pooled Mutagenic Screening Identifies KMT2D as a Major Modulator of Immune Checkpoint Blockade. Cancer Discov 10, 1912-1933 (2020).
Wang, L., et al., Resetting the epigenetic balance of Polycomb and COMPASS function at enhancers for cancer therapy. Nat Med 24, 758-769 (2018).
Wang, S. P., et al., A UTX-MLL4-p300 Transcriptional Regulatory Network Coordinately Shapes Active Enhancer Landscapes for Eliciting Transcription. Mol Cell 67, 308-321 e306 (2017).
Wu, Huai-liang, et al. "Targeting nucleotide metabolism: a promising approach to enhance cancer immunotherapy." Journal of Hematology & Oncology 15.1 (2022): 1-21.
Yizhak, K., et al., RNA sequence analysis reveals macroscopic somatic clonal expansion across normal tissues. Science 364, (2019).
Yokoyama, A., et al., Age-related remodelling of oesophageal epithelia by mutated cancer drivers. Nature 565, 312-317 (2019).
Yu, G., L. G. Wang, Q. Y. He, ChIPseeker: an R/Bioconductor package for ChIP peak annotation, comparison and visualization. Bioinformatics 31, 2382-2383 (2015).
Zhang Y., et al., Model-based analysis of ChIP-Seq (MACS). Genome Biol 9, R137 (2008).
Zhang, J., et al., Disruption of KMT2D perturbs germinal center B cell development and promotes lymphomagenesis. Nat Med 21, 1190-1198 (2015).
Zhang, Y., G. Parmigiani, W. E. Johnson, ComBat-seq: batch effect adjustment for RNA-seq count data. NAR Genom Bioinform 2, Iqaa078 (2020).
Zhao, Z. et al., Systematic analyses of the cytotoxic effects of compound 11a, a putative synthetic agonist of photoreceptor-specific nuclear receptor (PNR), in cancer cell lines. PloS one 8, e75198 (2013).
Zhou Y., et al., Metascape provides a biologist-oriented resource for the analysis of systems-level datasets. Nat Commun 10, 1523 (2019).
Brzezinka, K., Nevedomskaya, E., Lesche, R et al. Functional diversity of inhibitors tackling the differentiation blockage of MLL-rearranged leukemia. J Hematol Oncol 12, 66 (2019). https://doi.org/10.1186/s13045-019-0749-y.
Robinson, AD, Eich, M-L, Varambally, S. Dysregulation of de novo nucleotide biosynthetic pathway enzymes in cancer and targeting opportunities. Cancer Letters 470, 1, 134-140 (2020). https://doi.org/10.1016/j.canlet.2019.11.013.
Yadira M. Soto-Feliciano, Francisco J. Sánchez-Rivera, Florian Perner, et al.; A Molecular Switch between Mammalian MLL Complexes Dictates Response to Menin-MLL Inhibition. Cancer Discov Jan. 1, 2023; 13 (1): 146-169. https:// doi.org/10.1158/2159-8290.CD-22-0416.
Davison, C., Morelli, R., Knowlson, C et al. Targeting nucleotide metabolism enhances the efficacy of anthracyclines and anti-metabolites in triple-negative breast cancer. npj Breast Cancer 7, 38 (2021). https://doi.org/10.1038/ s41523-021-00245-5.
Wang X, Su W, Jiang Y, et al. Regulation of Nucleotide Metabolism with Nutrient-Sensing Nanodrugs for Cancer Therapy. Adv Sci 9, 20 (2022). https://doi.org/10.1002/advs.202200482.

(56) References Cited

OTHER PUBLICATIONS

C Sessa, J de Jong, M D'Incalci, S Hatty, O Pagani, F Cavalli; Phase I study of the antipurine antifolate lometrexol (DDATHF) with folinic acid rescue . . . Clin Cancer Res Jul. 1, 1996; 2 (7): 1123-1127.

Teresa Alati, John F. Worzalla, Chuan Shih, Jesse R. Bewley, Sidney Lewis, Richard G. Moran, Gerald B. Grindey; Augmentation of the Therapeutic Activity of Lometrexol [(6-R)5,10-Dideazatetrahydrofolate] by Oral Folic Acid1. Cancer Res May 15, 1996; 56 (10): 2331-2335.

D. Fantini, J. J. Meeks, The BBN model: a mouse bladder cancer model featuring basal-subtype gene expression and MLL3/MLL4 genetic disruption. Oncoscience 5, 172-173 (2018).

* cited by examiner

C
purine/pyrimidine synthesis
genes essential in Mll3/4 KO
RRA
(neg|score)
1e−14
1e−08
1e−02
0
5000
10000
15000
20000
Genes
Ppat
Mthfd1
Umps
Ak2
Gmps
Pfas
Ctps
Cad
Gart
Adsl
Paics
Dhodh
D
MLE – beta scores
KO
1
0
−1
−1.0
−0.5
0.0
0.5
1.0
WT
E
sgRNAs in Ppat
Read counts
70
50
30
20
sgRNAs in Mthfd1
Read counts
50
20
10
5
WT_d3
WT_d15
WT_d21
KO_d3
KO_d15
KO_d21

D
N-carb-asp (M+1)
Orotate (M+1)
UMP (M+1)
UTP (M+1)
Peak area (x 10³)
*
WT
Mll3/4KO
N-carb-asp (M+1)
Orotate (M+1)
UMP (M+1)
UTP (M+1)
Fractional abundance (%)
E
Hypoxanthine (M+5)
IMP (M+5)
AMP (M+5)
GMP (M+5)
Fractional abundance (%)
*
*
*
WT
Mll3/4KO A
% of inhibition
log2[lometrexol conc.(μM)]
WT
WT+HPX
Mll3/4 KO
Mll3/4 KO+HPX
B
rescue
treatment
WT.DMSO
WT.HPX
WT.LTX
WT.LTX+HPX
KO.DMSO
KO.HPX
KO.LTX
KO.LTX+HPX
KO vs. WT
C
PC1: 94% variance
PC2: 3% variance
Mll3/4 KO
HPX
LTX
group
KO:DMSO
KO:HPX
KO:LTX
KO:LTX_HPX
WT:DMSO
WT:HPX
WT:LTX
WT:LTX_HPX
D
KO_DMSO_vs_WT_DMSO (adj.p < 0.01)
cluster
treatment
type

H

B condition
shControl
shTarget
log2FC(KO/WT)
4 2 0 -2 -4
shDnmt3l
shMcf2
shFabp3
shUtf1
shSdc4
PLKO
PLKO
PLKO
shSusd2
shGlipr2
shAlpl
shHormad1
shBhmt
shDdc
shKhdc3
shCth
shSparc
shCd109
shDazl
shNcoa6
shMap6
z-score
4 2 0 -2 -4
C

D 100000 (cis)

B-B

A-A 0.0 0.2 0.4 0.6 0.8 1.0

E1 quantiles (contact frequency / expected)

2 1 0.5

WT 100000 (cis)

B-B

A-A 0.0 0.2 0.4 0.6 0.8 1.0

E1 quantiles (contact frequency / expected)

2 1 0.5

MLL3/4 KO

E
B-B
A-A
log2FC of MLL3/4 KO / WT
1.0
0.5
0.0
−0.5
−1.0
log2 fold change
F
180.2M
(6.79%)
B-A
A-B
(2.01%)
53.3M
Eigenvector in MLL3/4 KO
Eigenvector in WT
G
logFC of gene expression
(MLL3/4 KO/WT)
B-A
(361/1301)
stable
A-B
(91/229)

A

B

LTX (1 μM)
MLL4 Mutant
MLL4 WT
RKO HCT116 DLD1 Caco2 HT55 SW1417
H3 Ser10-p
CDT1
CyclinB1
Geminin
CyclinE1
CyclinA2
P-cdc2
Hsp90
PARP
Caspase3
β-tubulin
100
75
25
15

C
Downregulated genes with LTX treatmer
RKO
HCT116
DLD1
1038
656
1677
885
401
310
500
D
mutation
line
treatment
3
2
1
0
-1
-2
-3
mutation
Mutant
WT
line
RKO
HCT116
DLD1
HT55
Caco2
SW1417
treatment
DMSO
LTX
Commonly downregulated gene expression in LTX_vs_DMSO in RKO, HCT116 and DLD1 (n = 885)

Continued
C
Mll3/4 DKO/WT
H3K4me1
H3K27Ac
RNA
11,069 MLL4 peaks
Group1 (3826)
Group2 (7245)
-5kb 5' 3' 5kb
-5kb 5' 3' 5kb
LogFC (ChIP-seq)
3
0
-3
LogFC (RNA-seq)
1.5
0
-1.5
D
Feature
Promoter (<=1kb)
Promoter (1~2kb)
Promoter (2~3kb)
5' UTR
3' UTR
1st Exon
Other Exon
1st Intron
Other Intron
Downstream (<=300)
Distal Intergenic
Group1
Group2
0
25
50
75
100
Percentage (%)

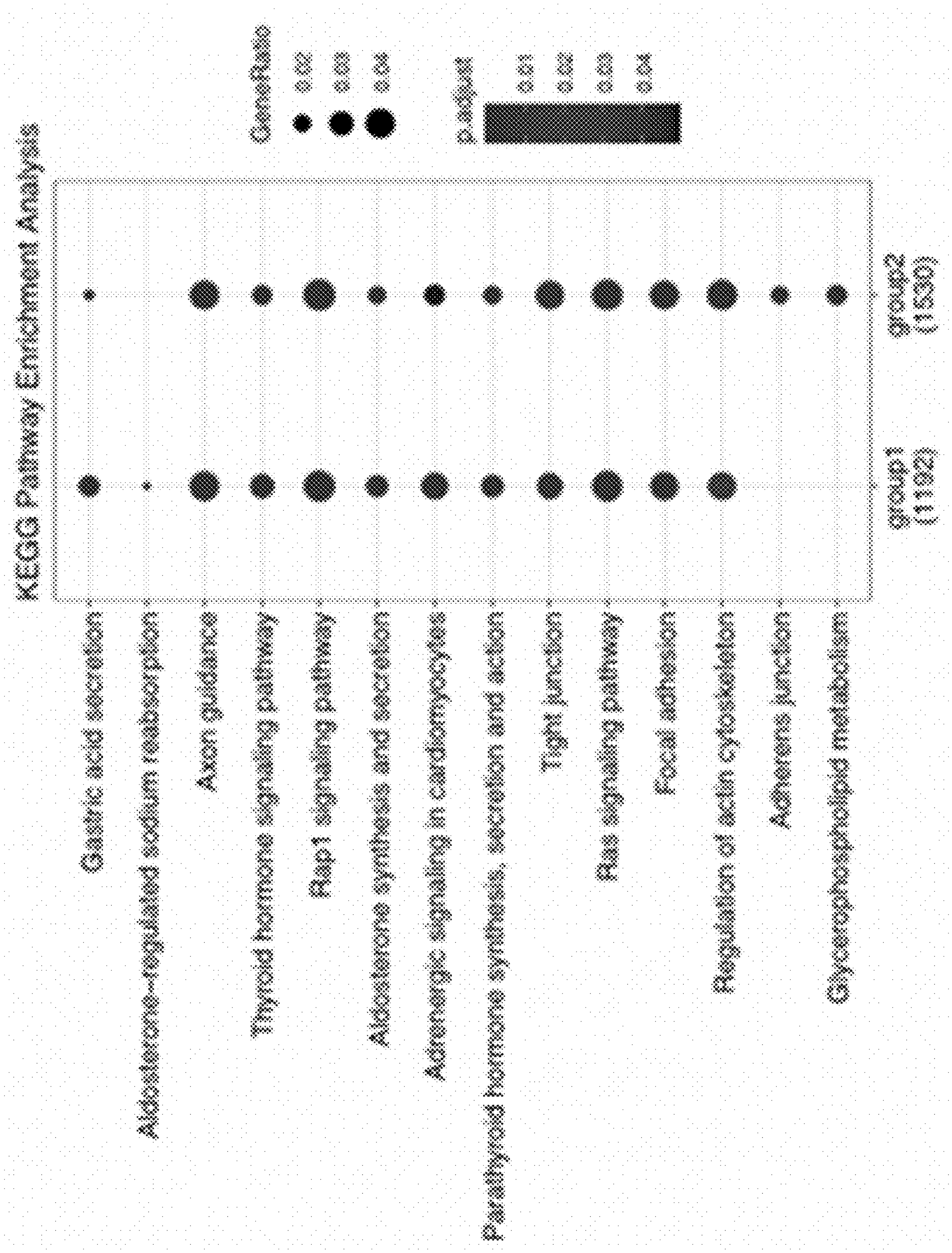

E

KEGG Pathway Enrichment Analysis

Gastric acid secretion
Aldosterone-regulated sodium reabsorption
Axon guidance
Thyroid hormone signaling pathway
Rap1 signaling pathway
Aldosterone synthesis and secretion
Adrenergic signaling in cardiomyocytes
Parathyroid hormone synthesis, secretion and action
Tight junction
Ras signaling pathway
Focal adhesion
Regulation of actin cytoskeleton
Adherens junction
Glycerophospholipid metabolism group1 (1192)
group2 (1530)

GeneRatio
0.02
0.03
0.04 p.adjust
0.01
0.02
0.03
0.04

C
sgRNAs in Umps
sgRNAs in Ak2
sgRNAs in Ctps
sgRNAs in Cad
sgRNAs in Gmps
sgRNAs in Pfas
sgRNAs in Paics
sgRNAs in Dhodh
sgRNAs in Gart
sgRNAs in Adsl
Read counts
WT_d3
WT_d15
WT_d21
KO_d3
KO_d15
KO_d21

A
% of inhibition
log2[LTX conc.(uM)]
WT
Mll3/4 KO#1
Mll3/4 KO#2
Mll3/4 KO#3
B
% of inhibition
log2[MTX conc.(uM)]
WT
Mll3/4 KO#1
Mll3/4 KO#2
Mll3/4 KO#3
C
% of inhibition
log2[SHIN1 conc.(μM)]
WT
Mll3/4 KO#1
Mll3/4 KO#2
Mll3/4 KO#3
D
LTX_vs_DMSO: Up-regulated
(adj.p <0.01)
WT
1894
1195
KO
1724

C
MLL4 using {7} peptides
NCOA6 using {3} peptides
UTX using {11} peptides
PAGR1 using {1} peptides
PAXIP1 using {11} peptides
DPY30 using {3} peptides
RBBP5 using {13} peptides
ASH2L using {19} peptides
WDR5 using {10} peptid
TMT RA
WT
KO

| Sample | WT | MLL3/4 KO |
|---|---|---|
| Loop number (10 kb) | 10,118 | 13,695 |
| TAD number (40 kb) | 2,514 | 2,447 |
| A/B Compartment number (100 kb) | 10,884/14,178 | 12,141/12,874 |

B
Top 100 upregulated genes in MLL3/4 KO versus WT
Average 3 bins
Average 5 bins
Eigenvector
p.val < 0.001
p.val < 0.001
WT
MLL3/4 KO
WT
MLL3/4 KO
C
Top 100 downregulated genes in MLL3/4 KO versus WT
Average 3 bins
Average 5 bins
Eigenvector
WT
MLL3/4 KO
WT
MLL3/4 KO

B

C

D

E

F

A

| Cell Line | FHC, normal | Caco2 | SW1417 | HT55 | SW480 | DLD1 | HCT116 | RKO |
|---|---|---|---|---|---|---|---|---|
| KMT2D | - | WT | WT | WT | D1633N | F5284L, L2304M, P1931H, E1667D, E1517D | R2443Sfs*6, V160M | L5056P, G3465*, P2550Lfs*33, L1600P, R1189H |
| KMT2C | - | S2427G | S1418L, P2050L | G1584L | Q4279* | G3438D, I1706V | I1344* | R3853W |
| KDM6A | - | WT | WT | WT | WT | WT | WT | WT |

B

C
DLD1
(KMT2D Mutant)
HCT116
(KMT2D Mutant)
RKO
(KMT2D Mutant)
SW480
(KMT2D Mutant)
% of inhibition
100
50
0
LTX conc. (μM)
0.000
0.005
0.014
0.041
0.123
0.370
1.111
3.333
10.000
30.000
0
10
30

F
HCT116
G
RKO
H
Caco2
I
HT55
shCtrl #1
shCtrl #2
shGART #1
shGART #2
shPAICS #1
shPAICS #2
D0
D1
D2
D3
D4
J
shCtrl
shGART
shPAICS
RKO
HCT116
Caco2
HT55

A

B

| Line | KMT2D | direction | LTX_vs_DMSO |
|---|---|---|---|
| RKO | Mut | up | 2922 |
| RKO | Mut | dn | 2980 |
| HCT116 | Mut | up | 3642 |
| HCT116 | Mut | dn | 3528 |
| DLD1 | Mut | up | 2147 |
| DLD1 | Mut | dn | 2096 |
| HT55 | WT | up | 1 |
| HT55 | WT | dn | 0 |
| Caco2 | WT | up | 22 |
| Caco2 | WT | dn | 3 |
| SW1417 | WT | up | 91 |
| SW1417 | WT | dn | 53 |

D

USE OF NUCLEOTIDE SYNTHESIS INHIBITORS FOR TARGETED THERAPY IN MLL3/4 COMPASS MUTANT CANCER

CROSS-REFERENCE TO RELATED APPLICATIONS

This application claims priority to U.S. Provisional Application No. 63/348,333 filed on Jun. 2, 2022, the contents of which are incorporated by reference in their entireties.

STATEMENT REGARDING FEDERALLY SPONSORED RESEARCH

This invention was made with government support under grant number CA197569 awarded by the National Institutes of Health. The government has certain rights in the invention.

REFERENCE TO AN ELECTRONIC SEQUENCE LISTING

The contents of the electronic sequence listing (702581.02344.xml; Size: 30,686 bytes; and Date of Creation: May 30, 2023) is herein incorporated by reference in its entirety.

BACKGROUND

MLL3 and MLL4, within the Complex of Proteins Associated with Set1 (COMPASS) family, are the major histone H3K4 mono-methyltransferases functioning at enhancers. Their roles in enhancer activity regulation and gene expression rely on both catalytic-dependent functions through H3K4 mono-methylation and catalytic-independent activities via co-function with UTX and p300 for enhancer activation. MLL3 and MLL4 are essential for a variety of developmental processes including mammalian myogenesis and adipogenesis, macrophage activation, cardiac development, and B-cell lymphomagenesis just to mention a few. The distinct requirement for MLL3 and MLL4 during mammalian development is stage dependent: MLL4 is required after implantation, and its action is dosage dependent; MLL3 is essential during late gestation and for organ maturation. In mouse embryonic stem cells (mESCs), MLL4 is dispensable for cell identity and self-renewal, but is essential for cells to exit pluripotency state and cell fate transition.

The emerging roles of chromatin function in developmental diseases and cancers involves the multifaceted and orchestrated interplay between chromatin-modifying enzymes, chromatin regulatory factors, and the regulatory elements on chromatin. The large consortium project, Catalogue Of Somatic Mutations In Cancer (COSMIC), has identified a large number of somatic mutations in chromatin modifiers that regulate enhancer chromatin across a wide-range of human tumor types. The most frequently mutated factors include H3K4 mono-methyltransferases MLL3 and MLL4 (KMT2C and KMT2D) and their cofactor H3K27 demethylase UTX (KDM6A) indicating the broad tumor suppressor roles of these proteins. Intriguingly, mutations resulting in loss-of-function on MLL4 and UTX also results in the developmental disorders such as Kabuki syndrome. Despite the extensive characterization of recurrent mutations across different cancer types and developmental disorders, scarce information has been acquired regarding the molecular mechanisms and functional consequences of the mutations in these essential genes that regulate enhancer chromatin function. In view of the foregoing, it would be desirable to better understand the functional outcomes of these mutations in MLL3/4 and any therapeutic insight it may provide.

SUMMARY

The inventors have demonstrated MLL3/4 COMPASS mutation may predict a higher sensitivity and response to nucleotide synthesis inhibitors in human cancers. Provided herein are methods and compositions for treating a subject in need of treatment for a MLL3/4 COMPASS deficient cancer or a MLL3/4 loss of function mutation.

One aspect of the present invention provides a method for treatment of a subject having a MLL3/4 COMPASS deficient cancer comprising administering to the subject an effective amount of a nucleotide synthesis inhibitor. In some embodiments, the subject has a MLL3/4 loss of function mutation. In some embodiments, the MLL3/4 COMPASS deficient cancer is a colorectal cancer, a breast cancer, a lung cancer, an esophageal cancer, a gastric cancer, a prostate cancer, a bladder cancer, a lymphoma, a leukemia or a medulloblastoma.

In some embodiments, the nucleotide synthesis inhibitor is a de novo purine synthesis inhibitor. In some embodiments, the purine synthesis inhibitor comprises a glycinamide ribonucleotide formyltransferase (GARFT) inhibitor, a phosphoribosyl pyrophosphate amidotransferase (PPAT) inhibitor, a phosphoribosylformylglycinamidine synthase (PFAS) inhibitor, phosphoribosylaminoimidazole succinocarboxamide synthetase (PAICS) inhibitor, an adenylosuccinate lyase (ADSL) inhibitor, an adenylosuccinate synthetase (AdSS) inhibitor, or a guanosine monophosphate synthetase (GMPS) inhibitor. In some embodiments, the purine synthesis inhibitor comprises lometrexol, methotrexate, or pelitrexol.

In some embodiments, the nucleotide synthesis inhibitor is a de novo pyrimidine synthesis inhibitor. In some embodiments, the pyrimidine synthesis inhibitor comprises a carbamoyl-phosphate synthetase 2, aspartate transcarbamoylase, and dihydroorotase (CAD) inhibitor; a dihydroorotate dehydrogenase (DHODH) inhibitor; or a Uridine 5'-monophosphate (LIMPS) inhibitor. In some embodiments the pyrimidine synthesis inhibitor comprises Brequinar or Leflunomide.

A second aspect of the present invention provides a method for treatment of a subject having a MLL3/4 loss of function mutation, the method comprising administering the subject an effective amount of a nucleotide synthesis inhibitor. In some embodiments, the subject has cancer.

In some embodiments the cancer is a colorectal cancer, a breast cancer, a lung cancer, an esophageal cancer, a gastric cancer, a prostate cancer, a bladder cancer, a lymphoma, a leukemia or a medulloblastoma.

In some embodiments the nucleotide synthesis inhibitor comprises a de novo purine synthesis inhibitor. In some embodiments the purine synthesis inhibitor comprises a glycinamide ribonucleotide formyltransferase (GARFT) inhibitor, a phosphoribosyl pyrophosphate amidotransferase (PPAT) inhibitor, a phosphoribosylformylglycinamidine synthase (PFAS) inhibitor, phosphoribosylaminoimidazole succinocarboxamide synthetase (PAICS) inhibitor, an adenylosuccinate lyase (ADSL) inhibitor, an adenylosuccinate synthetase (AdSS) inhibitor, or a guanosine monophosphate synthetase (GMPS) inhibitor. In some embodiments, the purine synthesis inhibitor comprises lometrexol, methotrexate, or pelitrexol.

In some embodiments, the nucleotide synthesis inhibitor comprises a de novo pyrimidine synthesis inhibitor. In some embodiments, the pyrimidine synthesis inhibitor comprises a carbamoyl-phosphate synthetase 2, aspartate transcarbamoylase, and dihydroorotase (CAD) inhibitor; a dihydroorotate dehydrogenase (DHODH) inhibitor; or a Uridine 5'-monophosphate (LIMPS) inhibitor. In some embodiments, the pyrimidine synthesis inhibitor comprises Brequinar or Leflunomide.

Another aspect of the present disclosure provides a method for the treatment of a subject, the method comprising obtaining a sample from a subject; testing the sample for the presence of a biomarker for a MLL3/4 COMPASS deficient cancer; and administering an effective amount of a nucleotide synthesis inhibitor to the subject if the sample tests positive for the biomarker. In some embodiments, the biomarker is a MLL3/4 loss of function mutation.

BRIEF DESCRIPTION OF THE DRAWINGS

The present technology can be better understood by reference to the following drawings. The drawings are merely exemplary to illustrate certain features that may be used singularly or in combination with other features and the present technology should not be limited to the embodiments shown.

(F), The roadmap of molecular changes and cellular phenotypes when mESCs lose MLL3/4.

DETAILED DESCRIPTION

Figure 1:
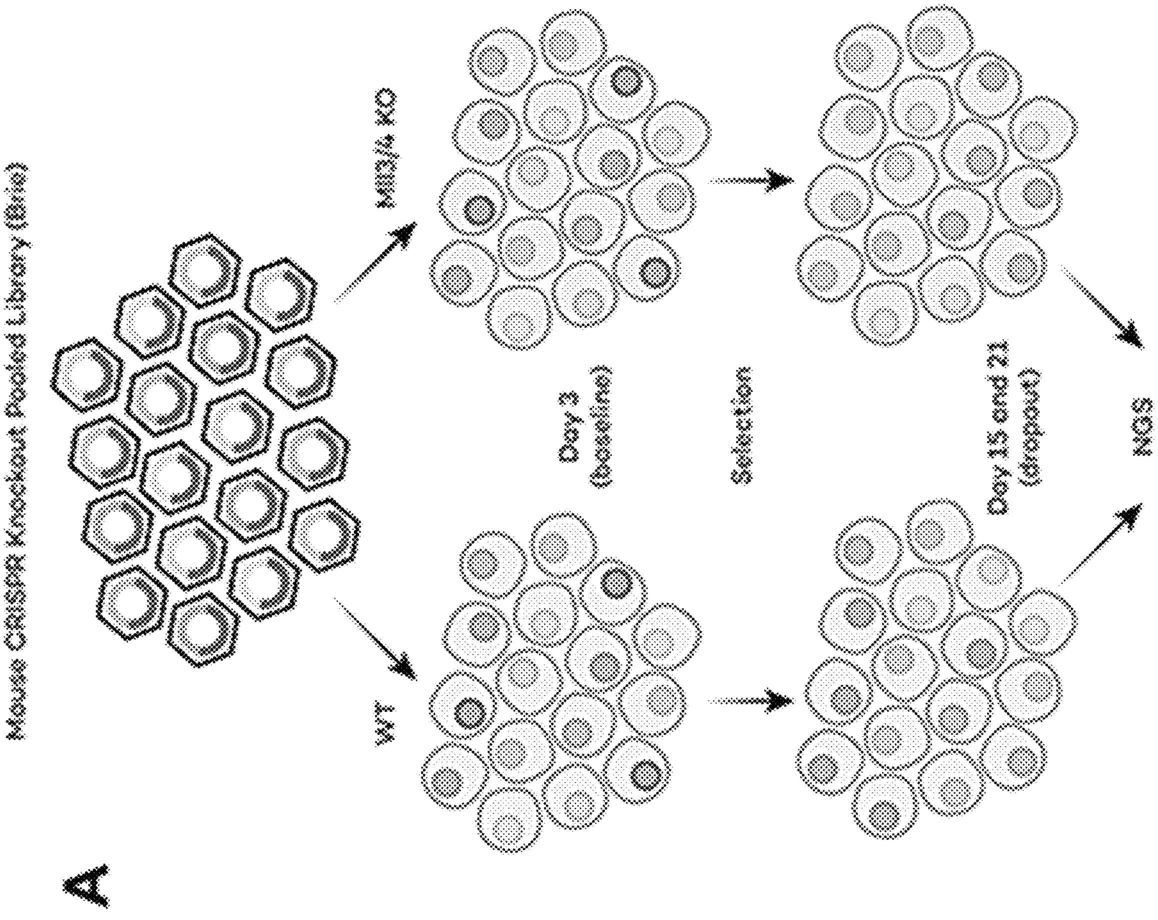
FIG. 1. Genome-wide Screens Identify Purine and Pyrimidine Synthesis Pathways Essential for viability in Mll3/4 KO mESCs. (A) The flowchart showing CRISPR Knockout dropout screening in WT and KO cells. (B) The GO biological process pathway analysis of top 300 negatively selected genes in Mll3/4 KO cells using MAGeCK analysis. (C) The rank plot showed the distribution of negative RRA score and highlighted the RRA scores of 12 genes essential in Mll3/4 KO involved in purine/pyrimidine synthesis. (D) Beta scores of gene essentialities were calculated for WT and KO cells. The 12 genes involved in purine/pyrimidine synthesis were shown in the 9-square view. (E) Distribution of sgRNA read counts (normalized) of two representative genes Ppat and Mthfd1 in WT and KO cells at different time points.
Figure 1:
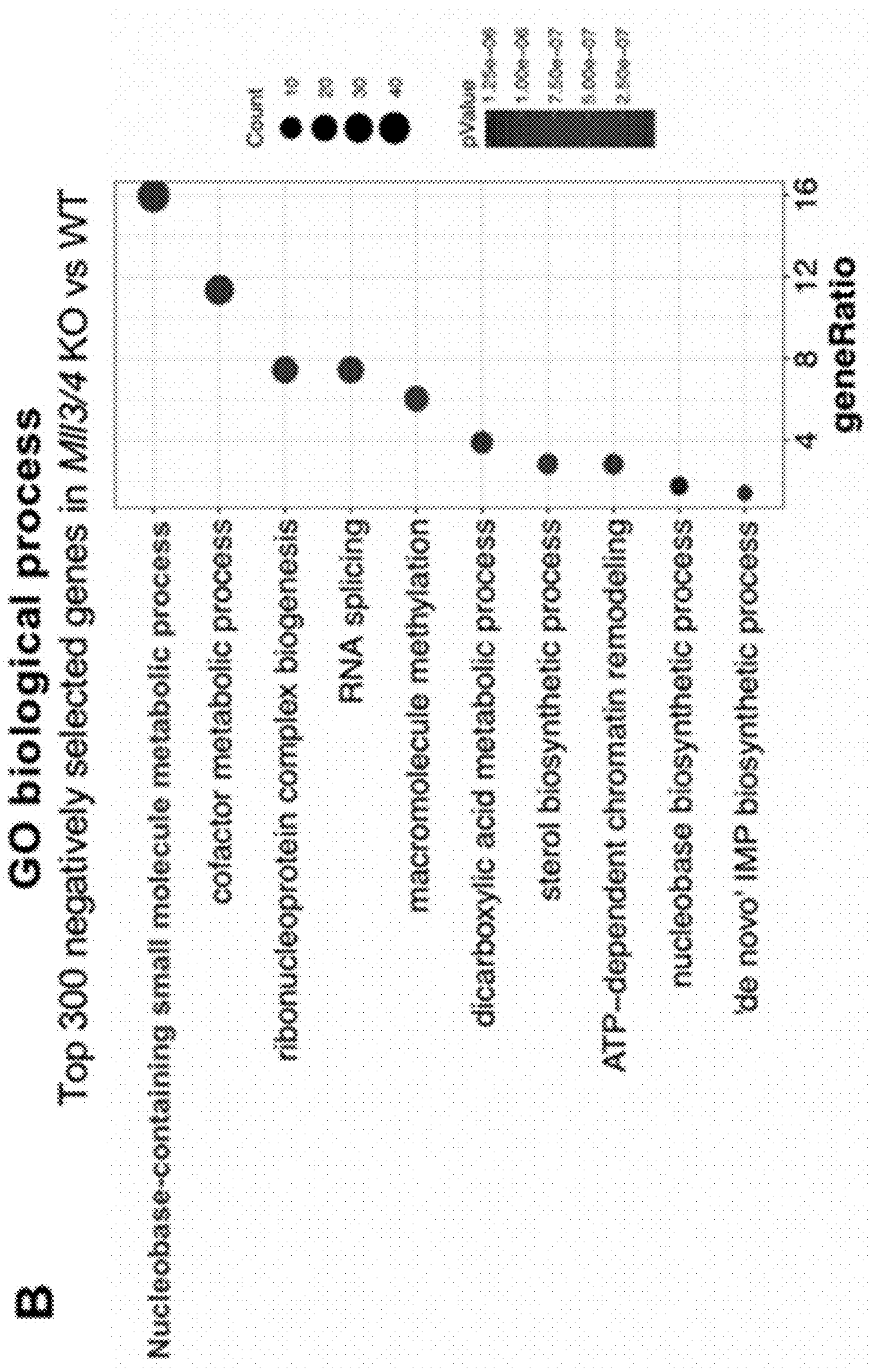
Figure 1:
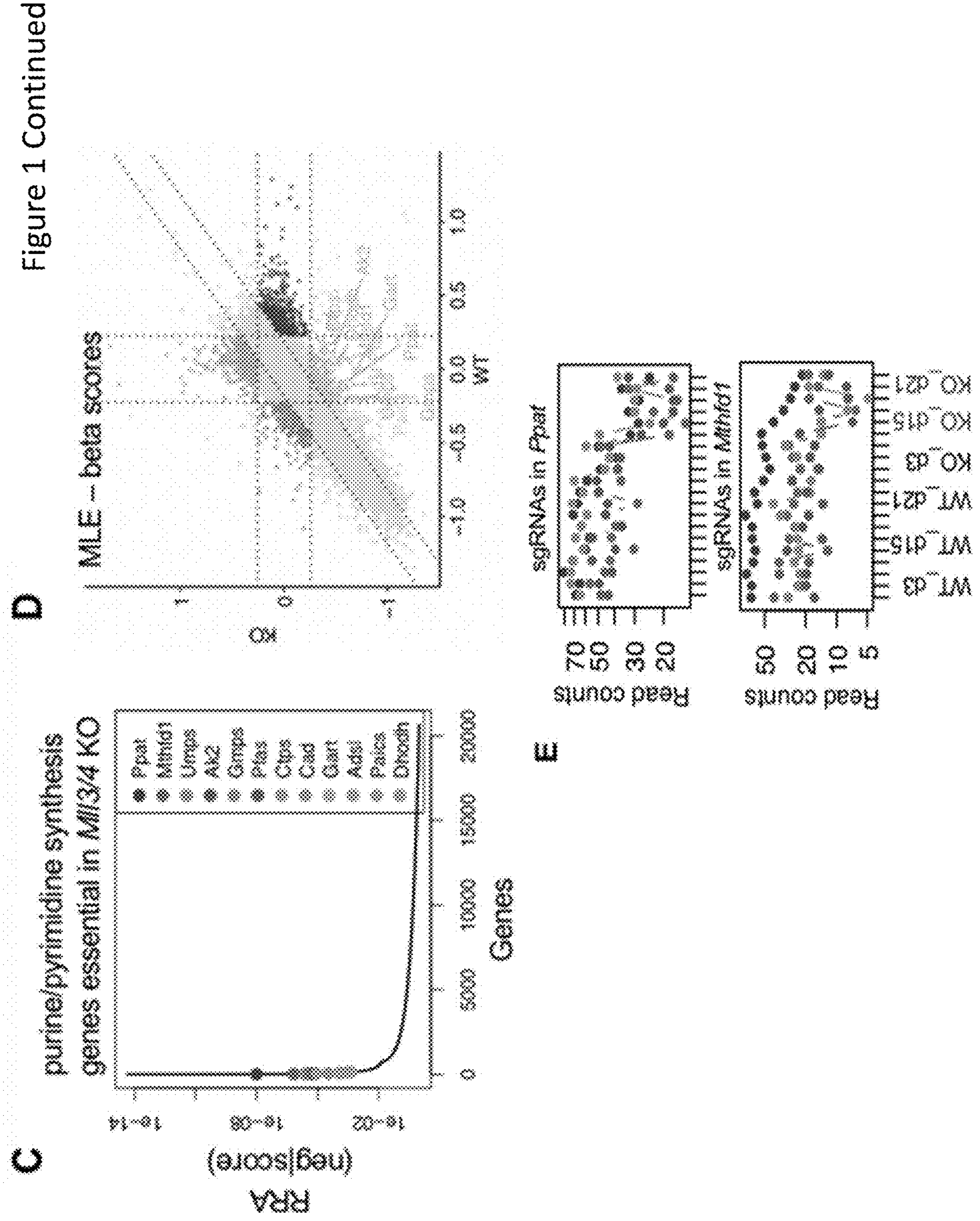

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

The examples provided herein demonstrate that MLL3/4 COMPASS mutations may predict a higher sensitivity and response to nucleotide synthesis inhibitors in human cancers. The present disclosure provides a method for treatment of a subject having a MLL3/4 COMPASS deficient cancer. The method includes administering the subject an effective amount of a nucleotide synthesis inhibitor. The present disclosure is based on phenotypic and genetic profiling following depletion of MLL3 and MLL4. These screens identified the existence of a de novo nucleotide synthesis dependency alteration when the functions of MLL3 and MLL4 were diminished in mESCs.

Methods for treating subjects with the compounds disclosed herein are provided. Suitably, the methods for treating a subject comprise administering to the subject an effective amount of a nucleotide synthesis inhibitor or a pharmaceutical composition comprising the effective amount of a nucleotide synthesis inhibitor. As used herein, a "subject" may be interchangeable with "patient" or "individual" and means an animal, which may be a human or non-human animal, in need of treatment. In particular embodiments, the subject is a human subject.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration. In some embodiments, the subject is responsive to therapy with one or more of the compounds disclosed herein in combination with one or more additional therapeutic agents.

A "subject in need of treatment" may include a subject having a disease, disorder, or condition that may be characterized by an absence of MLL3 and/or MLL4; MLL3 and/or MLL4 present at a lower level than expected for a particular cell, tissue, or organ type; or mutation affecting the activity or function of MLL3 and/or MLL4. The subject may have a disease, disorder, or condition characterized as having a MLL3 and/or MLL4 loss of function mutation.

A large number of somatic mutations have been identified in chromatin modifiers that regulate enhancer chromatin across a wide-range of human tumor types. The most frequently mutated factors include H3K4 mono-methyltransferases MLL3 and MLL4 (KMT2C and KMT2D) and their cofactor H3K27 demethylase UTX (KDM6A) indicating the broad tumor suppressor roles of these proteins.

COMPASS is also known as Complex Proteins Associated with Set1. COMPASS is a macromolecular complex that plays a role as a H3K4me3 methylase in eukaryotes. There are at least six members of the COMPASS family in mammals, two of which are MLL3 and MLL4. MLL3, and MLL4 are part of the COMPASS family of histone H3 lysine 4 (H3K4) methyltransferases responsible for catalyzing histone 3 lysine 4 monomethylation (H3K4me1) at enhancer chromatin. These enzymes form complexes with components common to all COMPASS members, as well as complex-specific subunits that enable unique functions. MLL3 is also known as Lysine N-methyltransferase 2C (KMT2C) and Myeloid/lymphoid or mixed-lineage leukemia 3. MLL4 is also known as Myeloid/lymphoid or mixed-lineage leukemia 4 and Lysine N-methyltransferase 2C (KMT2D).

In some embodiments, the subject has a disease, disorder, or condition characterized as a MLL3/4 COMPASS deficient cancer. MLL3/4 COMPASS deficient cancers are cancers in any organ of the body in which MLL3 and/or MLL4 are not present, present at a lower level than expected for the particular cell, tissue, or organ, or having a mutation affecting the activity of MLL3 and/or MLL4, e.g., a loss of function mutation. MLL3/4 COMPASS deficient cancers include, but are not limited to colorectal cancer, lung cancer, breast cancer, esophageal cancer, gastric cancer, prostate cancer, bladder cancer, leukemia, lymphoma, or medulloblastoma.

In some embodiments, the present disclosure provides a method for the treatment of a subject with a MLL3 and/or a MLL4 loss of function mutation, which may be termed a MLL3/4 loss of function mutation. A loss of function mutation is any mutation in which the altered gene product lacks the molecular function of the wild-type, or unmutated gene. A loss of function mutation results in reduced, altered or abolished protein function. A loss of function mutation can also be any genetic lesion that prevents the normal gene product from being produced or renders it inactive. A mutation that can cause of loss of function can include, but is not limited to substitution mutations, deletion mutations, insertion mutations, translocation mutations, frameshift mutations or nonsense mutations.

As used herein, a subject with a MLL3 and/or MLL4 loss of function mutation includes any genetic change in the MLL3 and/or MLL4 gene that abolishes protein function, diminishes protein function, inactivates protein function or prevents protein production. In some instances, the subject has a MLL4 loss of function mutation. In some instances, the subject has a MLL3 loss of function mutation. In some instances, the subject had both a MLL3 loss of function mutation and a MLL4 loss of function mutation.

The method of the present disclosure includes administering the subject an effective amount of a nucleotide synthesis inhibitor. As used herein, the term "administering" an agent, such as a therapeutic entity to a subject, animal or cell, is intended to refer to dispensing, delivering or applying the substance to the intended target. In terms of the therapeutic agent, the term "administering" is intended to refer to contacting or dispensing, delivering or applying the therapeutic agent to a subject by any suitable route for delivery of the therapeutic agent to the desired location in the animal, including delivery by either the parenteral or oral route, intramuscular injection, subcutaneous/intradermal injection, intravenous injection, intrathecal administration, buccal administration, transdermal delivery, topical administration, and administration by the intranasal or respiratory tract route.

As used herein the term "effective amount" refers to the amount or dose of the composition or compound that provides the desired effect. In some embodiments, the effective amount is the amount or dose of the compound, upon single or multiple dose administration to the subject, which provides the desired effect in the subject under diagnosis or treatment. Suitably the desired effect may be reduced tumor size and/or tumor progression.

An effective amount can be readily determined by those of skill in the art, including an attending diagnostician, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

In the present disclosure, a method is provided which comprises administering an effective amount of a nucleotide synthesis inhibitor to subjects having a MLL3/4 COMPASS deficient cancer or a MLL3/4 loss of function mutation. As used herein, a nucleotide synthesis inhibitor prevents the production of nucleic acids. Nucleotide metabolism is an essential metabolic process that enables the maintenance of cellular homeostasis. Nucleotides support nucleic acid and protein synthesis, energy preservation, signaling activity, and cytoskeletal function. Nucleotides can be produced through the de novo or salvage synthesis pathways. As used herein, “de novo” refers to the formation of any of the various complex biomolecules from simple molecules or precursors via a certain biochemical pathway. The de novo pathways utilize amino acids (such as glutamine and other small molecules) to build the purine and pyrimidine rings.

A de novo purine synthesis inhibitor blocks, prevents or hinders the enzymes catalyzing reactions in the de novo pathways for biosynthesis of purine nucleotides. Similarly, a de novo pyrimidine synthesis inhibitor blocks, prevents or hinders the enzymes catalyzing reactions in the de novo pathways for biosynthesis of pyrimidine nucleotides. De novo nucleotide synthesis inhibitors can be synthetic or natural-product analogues of pathway intermediates or inhibitors rationally designed from a knowledge of the catalytic mechanism.

In some embodiments the purine nucleotide synthesis inhibitor is a glycinamide ribonucleotide formyltransferase (GARFT) inhibitor but it need not be. GARFT is an enzyme in the process of de novo purine biosynthesis and catalyzes the N-formylation of glycinamide ribonucleotide. It converts glycinamide ribonucleotide (GAR) to glycinamide ribonucleotide formyl-acid (FGAR) by using N-10-formyl-tetrahydrofolate as the formyl donor. In some embodiments, the nucleotide synthesis inhibitor may be a phosphoribosyl pyrophosphate amidotransferase (PPAT), phosphoribosylformylglycinamidine synthase (PFAS), phosphoribosylaminoimidazole succinocarboxamide synthetase (PAICS), adenylosuccinate lyase (ADSL), adenylosuccinate synthetase (AdSS) or guanosine monophosphate synthetase (GMPS) inhibitor.

In some embodiments, the purine nucleotide synthesis inhibitor is lometrexol, ((2S)-2-[[4-[2-[(6R)-2-amino-4-oxo-5,6,7,8-tetrahydro-3H-pyrido[2,3-d]pyrimidin-6-yl] ethyl]benzoyl]amino]pentanedioic acid) but it need not be. Lometrexol is a folate analog antimetabolite with antineoplastic activity. Lometrexol inhibits GART preventing de novo purine synthesis, inhibiting DNA synthesis, arresting cells in the S phase of the cell cycle, and inhibiting tumor cell proliferation. Lometrexol also inhibits one carbon metabolism pathway enzymes including SHMT1 and SHMT2. In some embodiments, the nucleotide synthesis inhibitor comprises pelitrexol ((2S)-2-[[5-[2-[(6S)-2-amino-4-oxo-5,6,7,8-tetrahydro-3H-pyrido[2,3-d]pyrimidin-6-yl] ethyl]-4-methylthiophene-2-carbonyl]amino]pentanedioic acid) or methotrexate ((2S)-2-[[4-[(2,4-diaminopteridin-6-yl)methyl-methylamino]benzoyl]amino]pentanedioic acid).

In some embodiments the pyrimidine nucleotide synthesis inhibitor comprises a Carbamoyl-phosphate synthetase 2, Aspartate transcarbamoylase, and Dihydroorotase (CAD) inhibitor; dihydroorotate dehydrogenase (DHODH) inhibitor (for example BAY-2402234); or Uridine 5'-monophosphate (LIMPS) inhibitor (for example Pyrazofurin).

In some embodiments, the pyrimidine nucleotide synthesis inhibitor is selected from Brequinar (6-Fluoro-2-(2'-fluoro-[1,1'-biphenyl]-4-yl)-3-methylquinoline-4-carboxylic acid) and Leflunomide (5-methyl-N-[4-(trifluoromethyl)phenyl]-1,2-oxazole-4-carboxamide).

The methods disclosed herein may utilize two or more nucleotide synthesis inhibitors. Combinations of two or more purine nucleotide synthesis inhibitors may be utilized in the present methods. Combinations of two or more pyrimidine nucleotide synthesis inhibitors may be utilized in the present methods. Combinations of one or more purine nucleotide synthesis inhibitors and one or more pyrimidine nucleotide synthesis inhibitors may also be utilized in the present methods.

Another aspect of the present disclosure provides a method for the treatment of a subject, comprising, consisting of, or consisting essentially of: (a) obtaining a sample from a subject; (b) testing the sample for the presence of a biomarker for a MLL3/4 COMPASS deficient cancer; (c) and administering an effective amount of a nucleotide synthesis inhibitor to the subject if the sample tests positive for the biomarker.

The term “sample” as used herein includes, but is not limited to, a sample containing tissues, cells, and/or biological fluids isolated from a subject. Examples of samples include, but are not limited to, tissues, cells, biopsies, blood, lymph, serum, plasma, urine, saliva, mucus and tears. In some embodiments, the sample is a biopsy (such as a tumor biopsy). A biological sample may be obtained directly from a subject (e.g., by blood or tissue sampling) or from a third party (e.g., received from an intermediary, such as a health-care provider or lab technician).

The term “biomarker” as used herein refers to a naturally occurring biological molecule present in a subject at varying concentrations useful in predicting the risk or incidence of a disease or a condition, such as a MLL3/4 COMPASS deficient cancer. For example, the biomarker can be a protein present in higher or lower amounts in a subject at risk for or diagnosed with colorectal cancer. The biomarker can include nucleic acids, ribonucleic acids, polypeptide, presence of a mutation, methylation status, or pattern, or other epigenetic marker or pattern used as an indicator or marker for colorectal cancer in the subject. An exemplary biomarker may also include a MLL4 and/or a MLL3 loss of function mutation. A sample which tests positive for the biomarker is any sample that shows the presence, or any other corollary change in the appropriate marker.

The present disclosure provides a pharmaceutical composition for treating the MLL3/4 COMPASS deficient cancer. The present disclosure also provides a pharmaceutical composition for treating a subject having the MLL3/4 loss of function mutation. The compositions comprising the effective amount of a nucleotide synthesis inhibitor and a pharmaceutically acceptable excipient, carrier, or diluent.

The compositions described herein includes a suitable carrier or vehicle for delivery. As used herein, the term “carrier” refers to a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, may be found in the U.S. Pharmacopeia National Formulary, 1857-1859, (1990).

Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator.

Examples of pharmaceutically acceptable antioxidants include water soluble antioxidants such as ascorbic acid, cysteine hydrochloride, sodium bisulfate, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

The present formulation may also comprise other suitable agents such as a stabilizing delivery vehicle, carrier, support or complex-forming species. The coordinate administration methods and combinatorial formulations of the instant invention may optionally incorporate effective carriers, processing agents, or delivery vehicles, to provide improved formulations for delivery of the nucleotide synthesis inhibitor described herein.

The composition may additionally include a biologically acceptable buffer to maintain a pH close to neutral (7.0-7.3). Such buffers preferably used are typically phosphates, carboxylates, and bicarbonates. More preferred buffering agents are sodium phosphate, potassium phosphate, sodium citrate, calcium lactate, sodium succinate, sodium glutamate, sodium bicarbonate, and potassium bicarbonate. The buffer may comprise about 0.0001-5% (w/v) of the formulation, more preferably about 0.001-1% (w/v). Other excipients, if desired, may be included as part of the final composition.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the present disclosure. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps.

All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

In those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The following examples are meant only to be illustrative and are not meant as limitations on the scope of the invention or of the appended claims.

EXAMPLES

Figure 7:
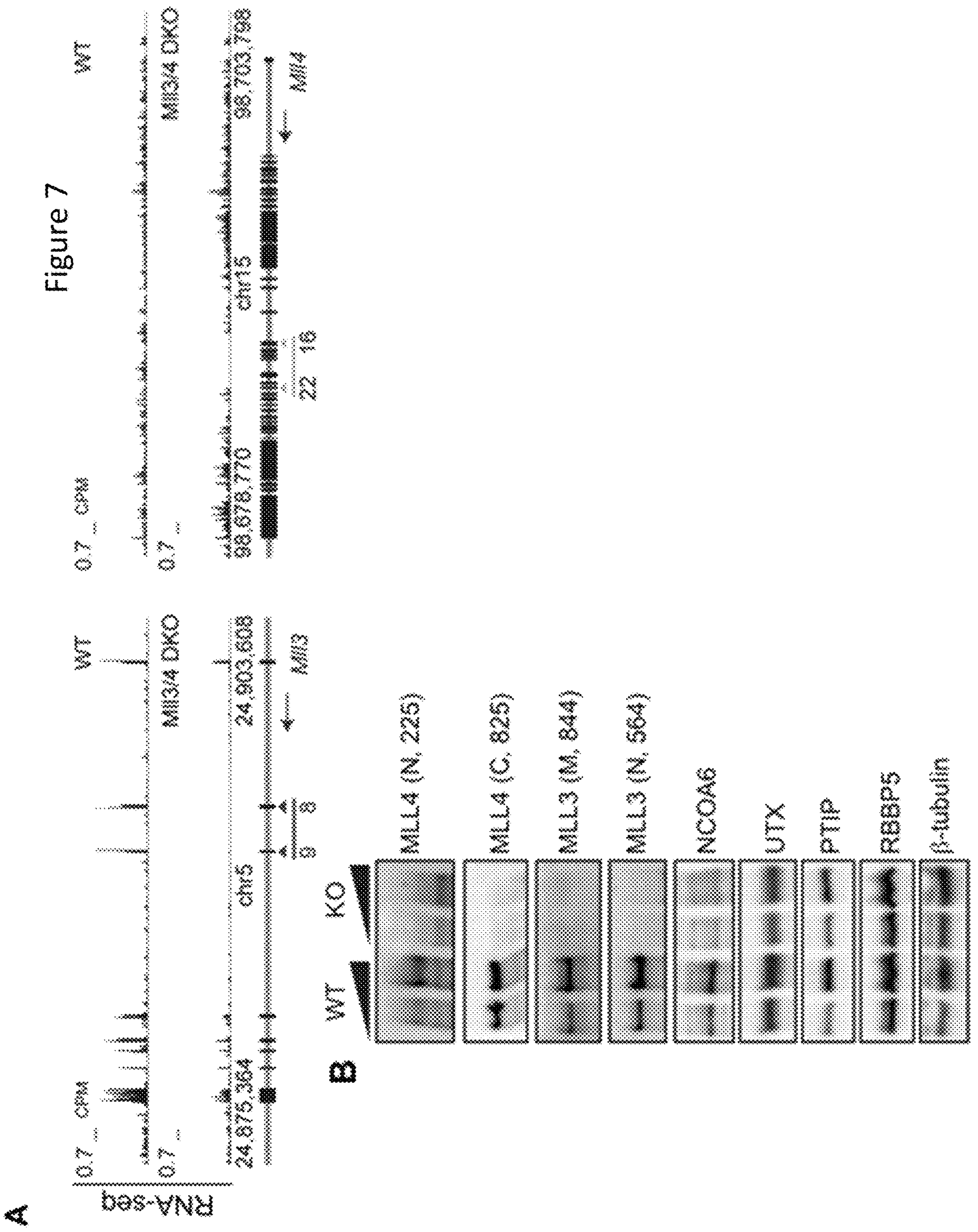
FIG. 7. Characterization of M113 and M114 double knockout mESCs. (A) RNA-seq track showing the CRISPR strategy to knock out M113 and M114 at exon 8-9 and exon 16-22 respectively. (B) Western blot showing the successful knockout of MLL3 and MLL4 with β-tubulin and RBBP5 as internal control. Other subunits of MLL3/4 COMPASS including NCOA6, UTX, and PTIP were also shown with decreased signals in Mll3/4 KO cells. N, N-terminus; M, middle region; C, C-terminus. Uncropped western blot images were shown in FIG. S15. (C) H3K4me1 and H3K27Ac ChIP-seq was performed in WT and Mll3/4 KO cells. K-means clustering (k=2) separated the previous defined MLL4 peaks (9) into two groups based on the log 2 fold change ChIP-seq signal of H3K4me1 and H3K27Ac. Meta-analysis showed Group2, with prominent H3K4me1 and H3K27Ac reduction in Mll3/4 KO cells, had strongly reduced gene expression of those occupied by MLL4. (D-E) Feature distribution of group1 and group2 MLL4 peaks (D) and the KEGG pathway enrichment analysis of group1 and group2 genes (E) using ChIPseeker package (62). (F) RNA-seq track showing the Pou5f1 and Nanog gene expression in WT and Mll3/4 KO cells. (G) Cell growth rates of WT and Mll3/4K0 cells. Cells were seeded in 6-well plates at 1×105 cells/mL. Cell number was counted with Beckman Vi-Cell XR Cell Viability Analyzer. Cell numbers were normalized to day 1.
Figure 7:
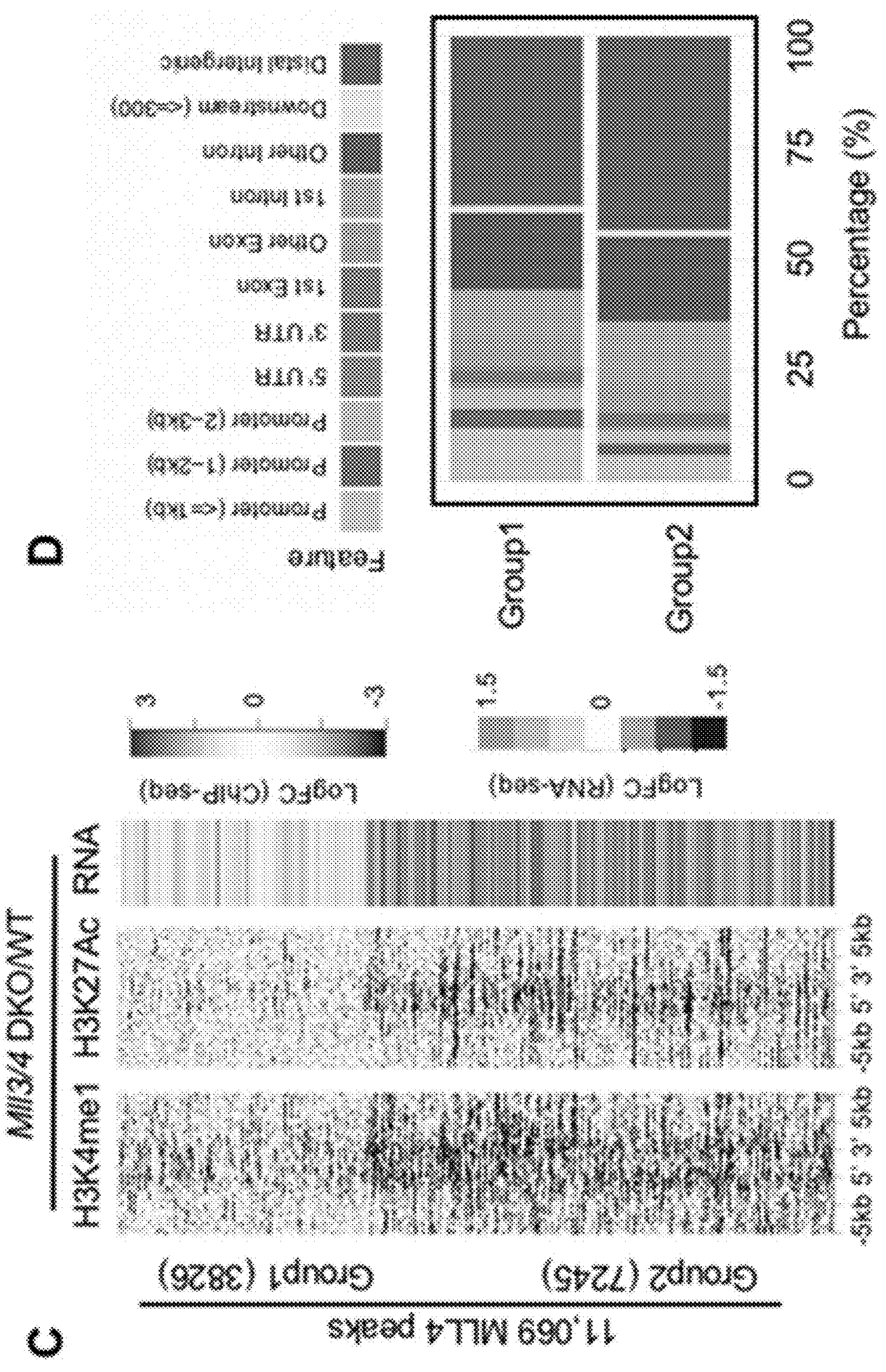
Figure 7:
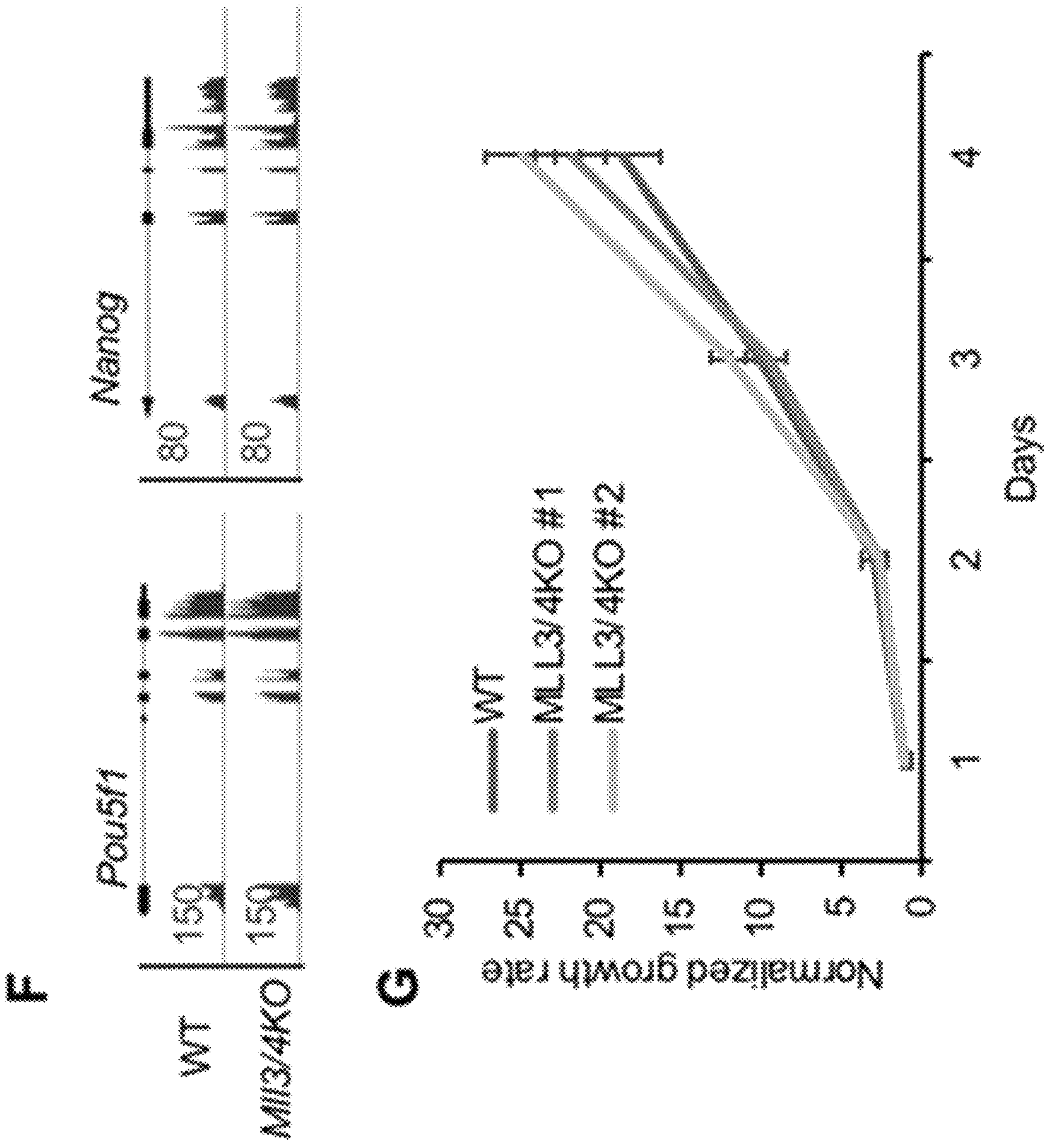

Example 1: Synthetic Lethal Approach Using Nucleotide Synthesis Inhibitors to Target Vulnerable Epigenetic Modifier Mutations in Cancer Results Genome-Wide Screens Identify Purine and Pyrimidine Synthesis Pathways Essential for Viability in Mll3/4 KO mESCs To characterize the consequences and phenotypic changes of MLL3/4 loss, we generated an Mll3/4 double knockout mouse ES cell line by deleting exon8-9 of Mll3 and exon 16-22 of Mll4 respectively (FIG. 7A). Successful knockout of Mll3 and Mll4 was confirmed by Western blot analysis using antibodies against different regions of MLL3 and MLL4, and subunits unique to MLL3/4 branch of COMPASS (including NCOA6, UTX, and PTIP) (FIG. 7B). To examine the histone modifications and gene expression pattern changes in Mll3/4 KO cells, we performed H3K4me1 and H3K27Ac ChIP-seq. K-means clustering (k=2) separated the previous defined M114 peaks (9) into two groups based on the log 2 fold change ChIP-seq signal of H3K4me1 and H3K27Ac (FIG. 7C). Meta-analysis of Group2 revealed that prominent H3K4me1 and H3K27Ac reduction in Mll3/4 KO cells coincided with strongly reduced gene expression of those where MLL4 peaks were found (FIG. 7C). Feature distribution of MLL4 peaks and the KEGG pathway enrichment analysis of nearby genes demonstrated similar distribution of MLL4 peaks. These peaks were mostly at enhancer regions in group 1 and group2 defined by K-means clustering and enriched in pathways related to cytoskeleton and junction organization (FIG. 7D, E). Finally, pluripotency markers, including Pou5f1 and Nanog gene expression, remained the same in WT and Mll3/4 KO cells suggesting MLL3/4 are dispensable for self-renewal of the mESCs (FIG. 7F). The cellular growth rates of WT and MLL3/4K0 cells were comparable (FIG. 7G).

Figure 8:
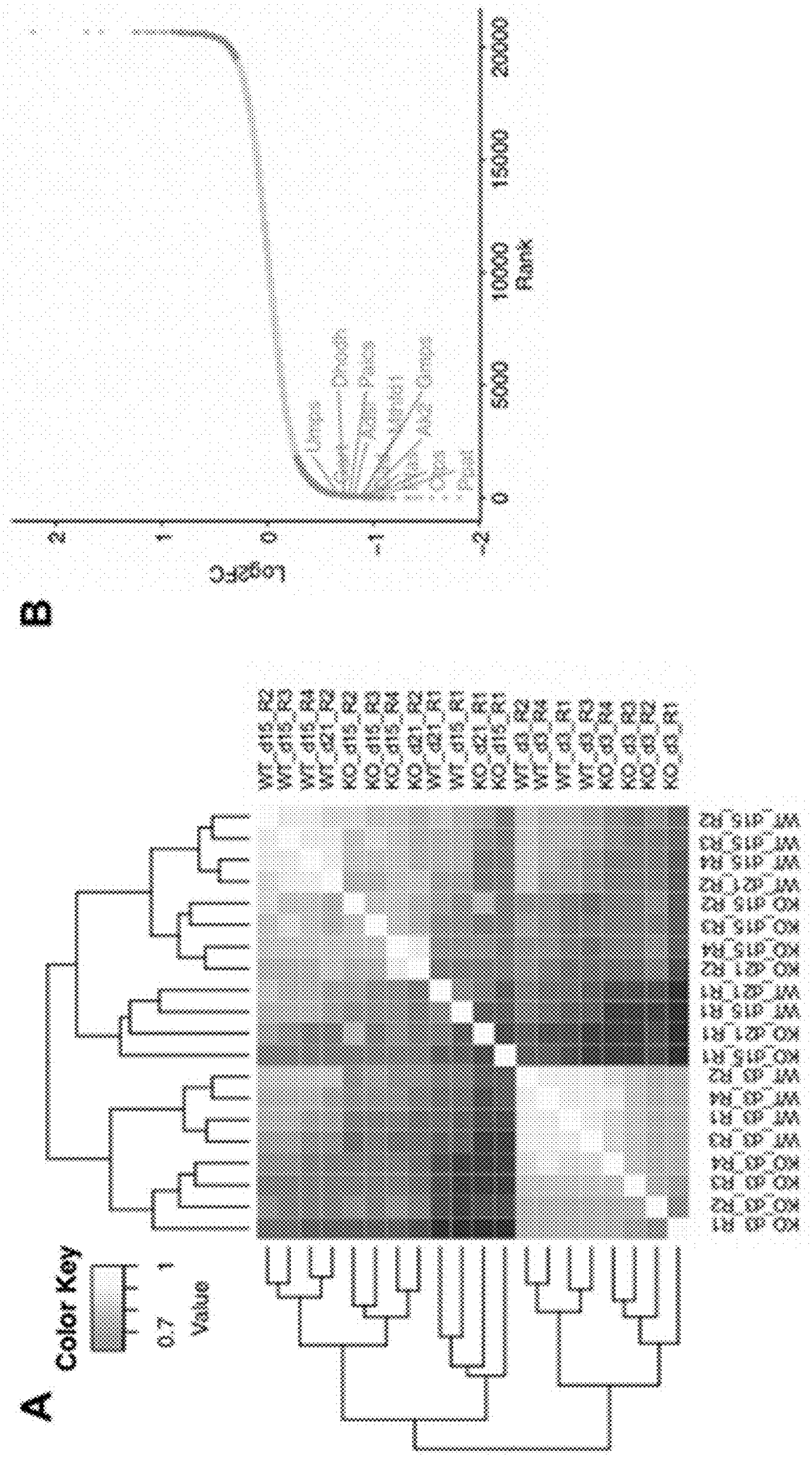
FIG. 8. Genome-wide Screens Identify Purine and Pyrimidine Synthesis Pathways Essential in Mll3/4 KO mESCs. (A) Sample clustering showed the groups based on time points and replicates of different conditions. (B) Overall log 2FC rank plot with purine/pyrimidine genes highlighted. (C) Distribution of sgRNA read counts (normalized) of purine/pyrimidine synthesis genes in WT and KO cells at different time points. (D) WT and KO cells were labeled with GFP and mCherry and were mixed 1:1 ratio. Mixed cells were infected with sgRNAs, and fluorescence was analyzed with flow cytometry. (E) The validation of several negatively selected genes in Mll3/4 KO. Normalized ratio of mCherry/GFP is calculated indicating KO cells are selectively targeted by these sgRNAs.
Figure 8:
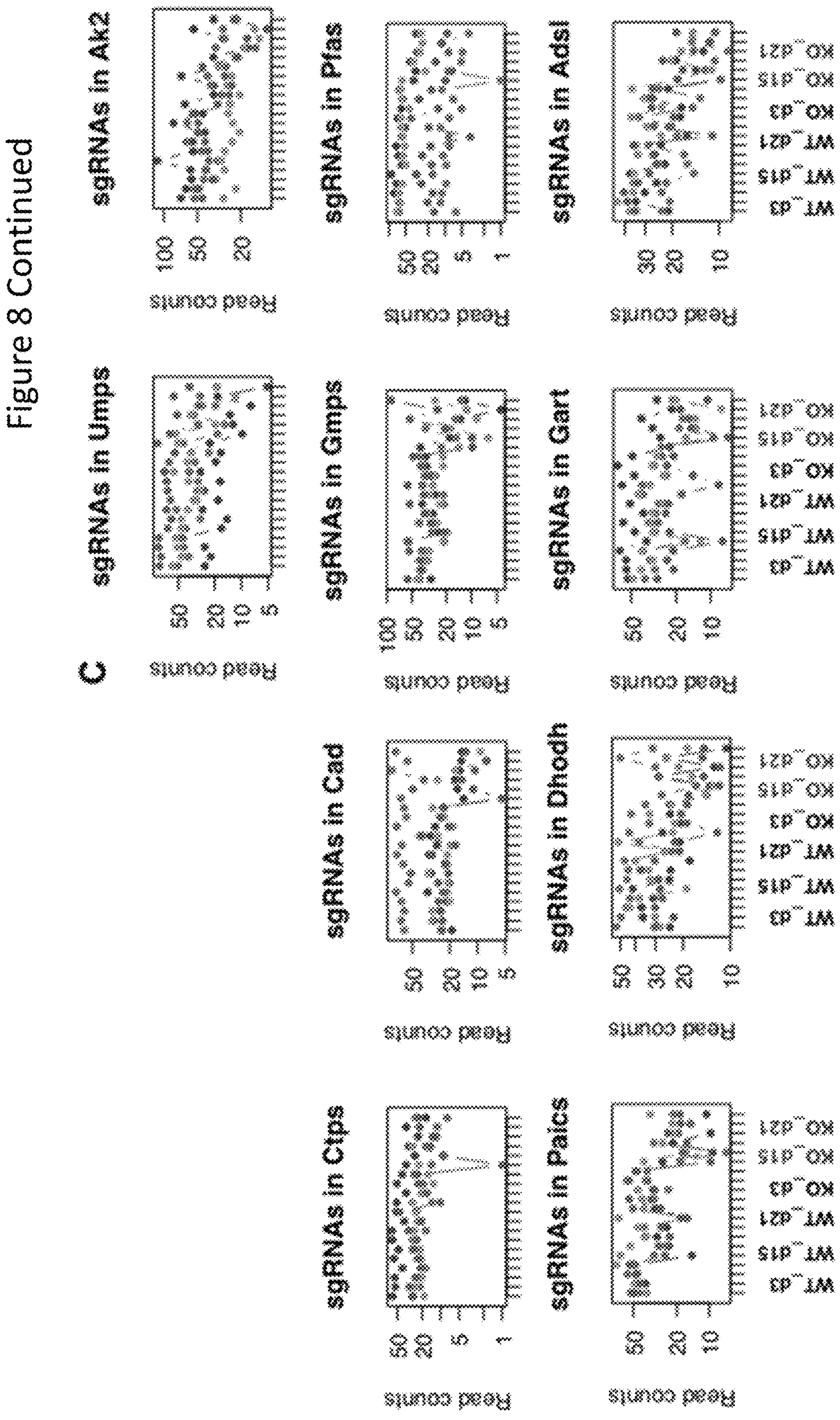
Figure 8:
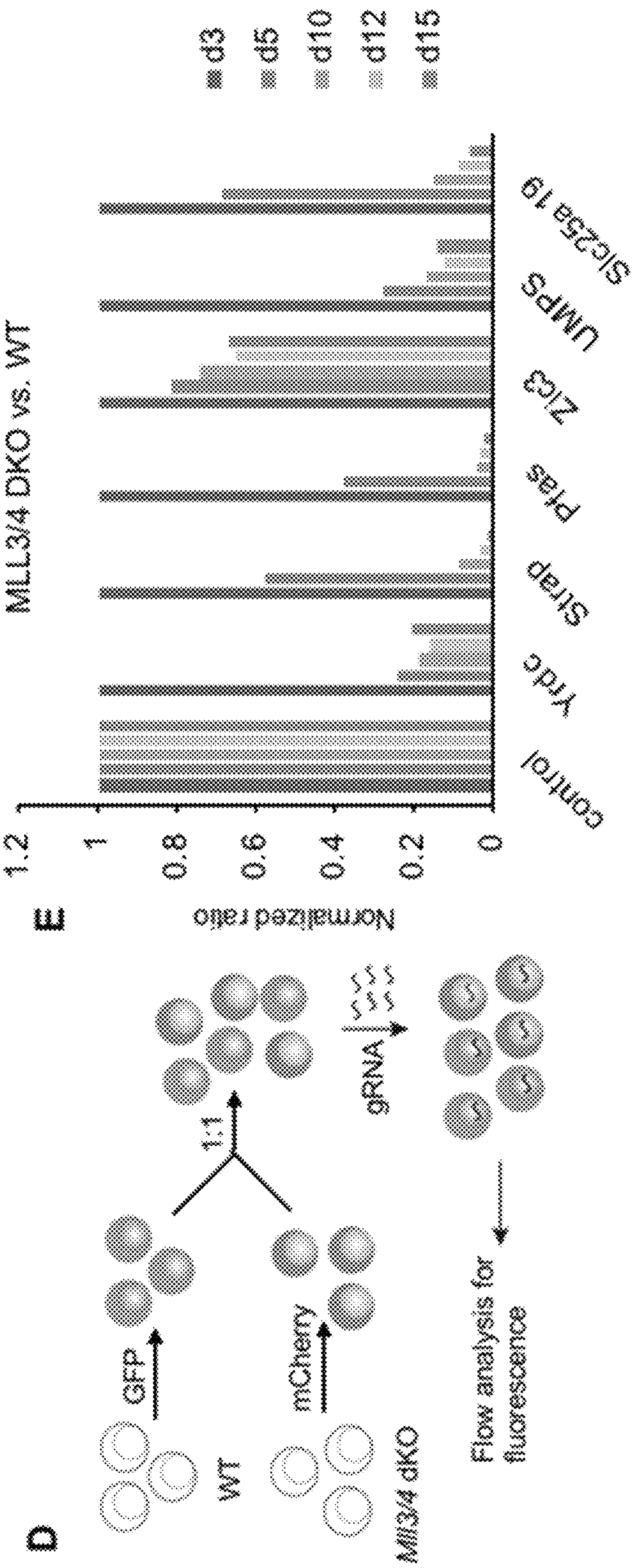

To investigate the cellular vulnerabilities with MLL3/4 depletion, we performed a dropout screen with the Brie CRISPR knockout library in WT and Mll3/4 KO mESCs (FIG. 1A). We took day 3 as initial state and day 15/21 as final state. After scrutinizing normalized read counts and sample clustering (FIG. 8A), the enrichment of sgRNAs in live cells after 15 and 21 days of selection was compared with cells harvested at 3 days of infection without selection (FIG. 1A). The top 300 negatively selected genes in Mll3/4 KO cells, in comparison with wild type cells, were enriched in pathways related to a variety of metabolic processes including 'nucleobase-containing small molecule metabolic process' (FIG. 1B). Specifically, the 12 critical metabolic enzymes involved in purine and pyrimidine synthesis (16) were all essential at final state as shown in the rank plot based on the negative RRA score (17) (FIG. 1C). To further examine the dependencies of these metabolic genes, the beta score of gene essentiality was calculated for WT and KO cells using MLE algorithm (18). Indeed, all these critical purine and pyrimidine de novo synthesis genes were only essential in KO, but not WT cells, as shown in the scatter plot (FIG. 1D). This was further explored by examining the log 2 fold change of sgRNA enrichment (FIG. 8B). For instance, distribution of normalized sgRNA read counts of Ppat and Mthfd1 were depleted only in Mll3/4 KO cells at final state (day 15 and day 21) (FIG. 1E). Similar trends were also observed with other genes encoding the critical metabolic enzymes for de novo purine and pyrimidine synthesis (FIG. 8C). To validate the CRISPR screening results, WT and KO cells were labeled with GFP and mCherry fluorescent proteins and mixed one-to-one ratio for individual sgRNAs infection. Fluorescent signals were captured with flow cytometry during the indicated time course (FIG. 8D). Normalized ratio of mCherry/GFP was calculated for several negatively selected genes in Mll3/4 KO cells (including Yrdc, Strap, Pfas, Zic3, Umps and Slc25a19) suggesting KO cells are preferentially more sensitive to the depletion of these genes by sgRNAs (FIG. 8E). Overall, our CRIPSR screen identified the existence of a de novo nucleotide synthesis dependency alteration when the functions of MLL3 and MLL4 were diminished in mESCs.

Loss of MLL3 and MLL4 Increases Flux Through Purine Synthesis in mESCs

Figure 9:
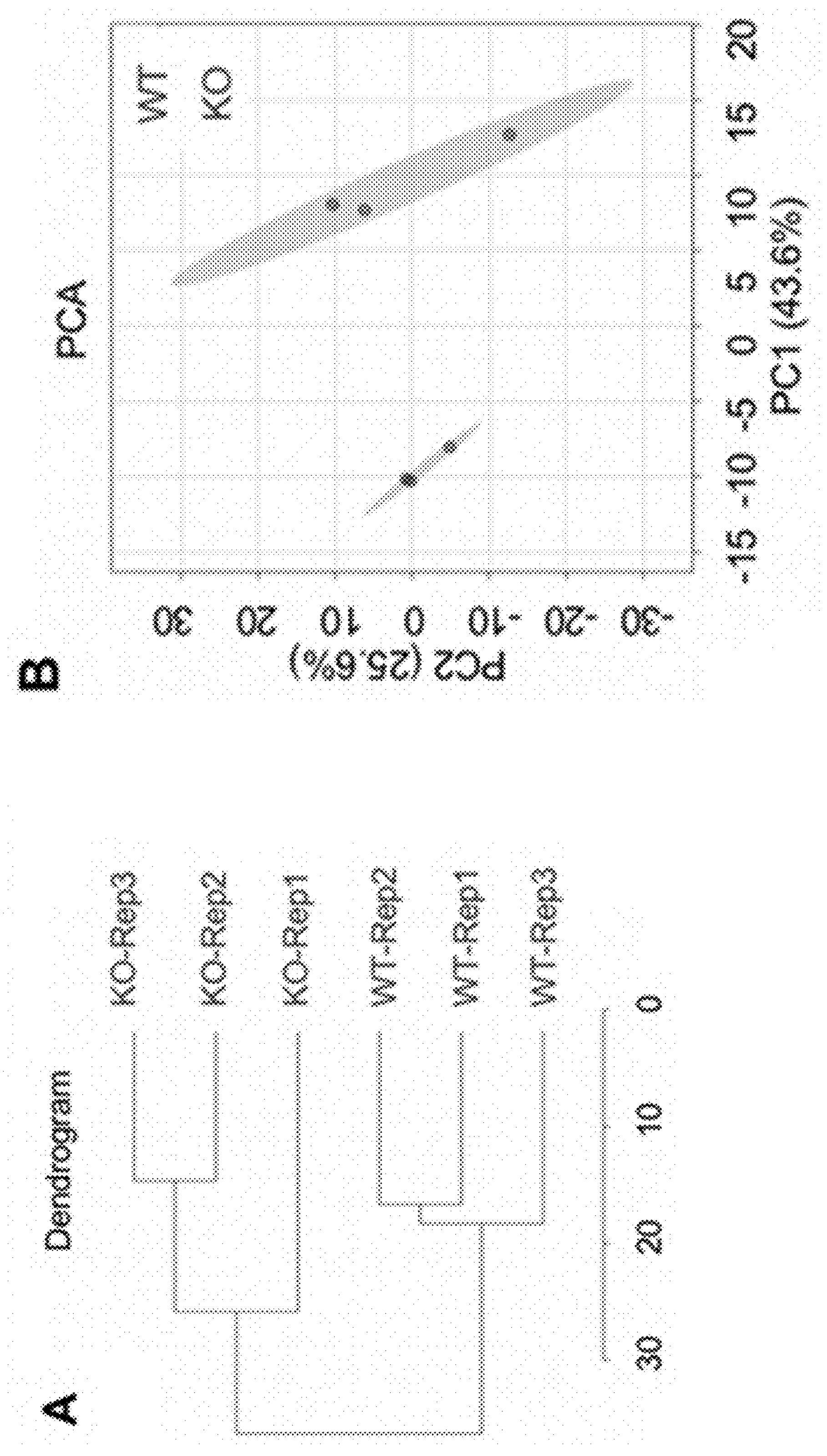
FIG. 9. Global Steady State Metabolomics of WT and Mll3/4 KO mESCs. (A) Dendrogram of WT and KO cells steady state metabolomics. (B) PC analysis of WT and KO cells steady state metabolomics. (C) Hierarchical clustering heatmap showing the differentially changed metabolites in WT and KO cells. (D) Volcano plot showing the significantly altered metabolites by log 10 p value and log 2 fold change. (E) Different important features in WT and KO cells ranked by the VIP scores.
Figure 9:
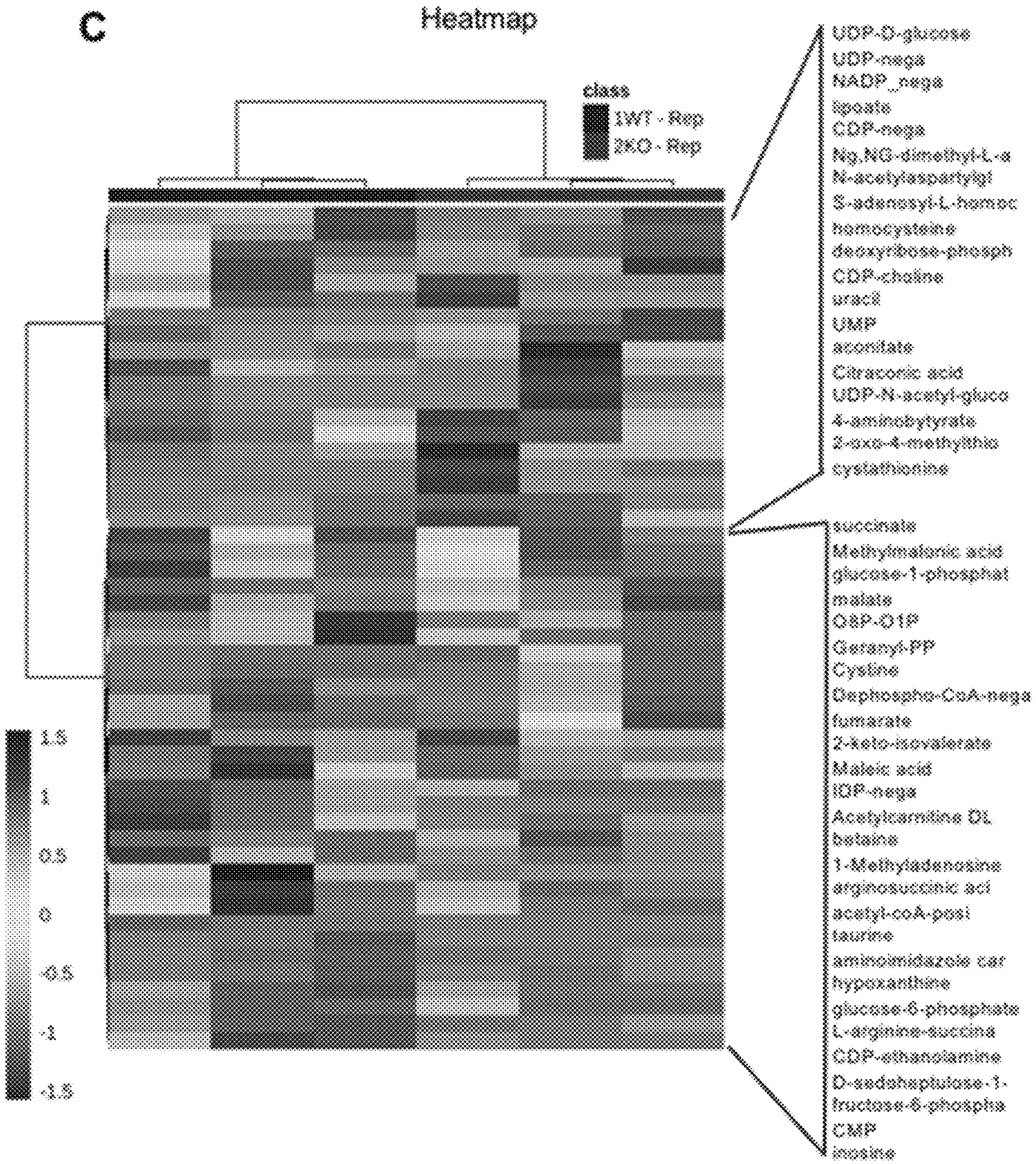
Figure 9:
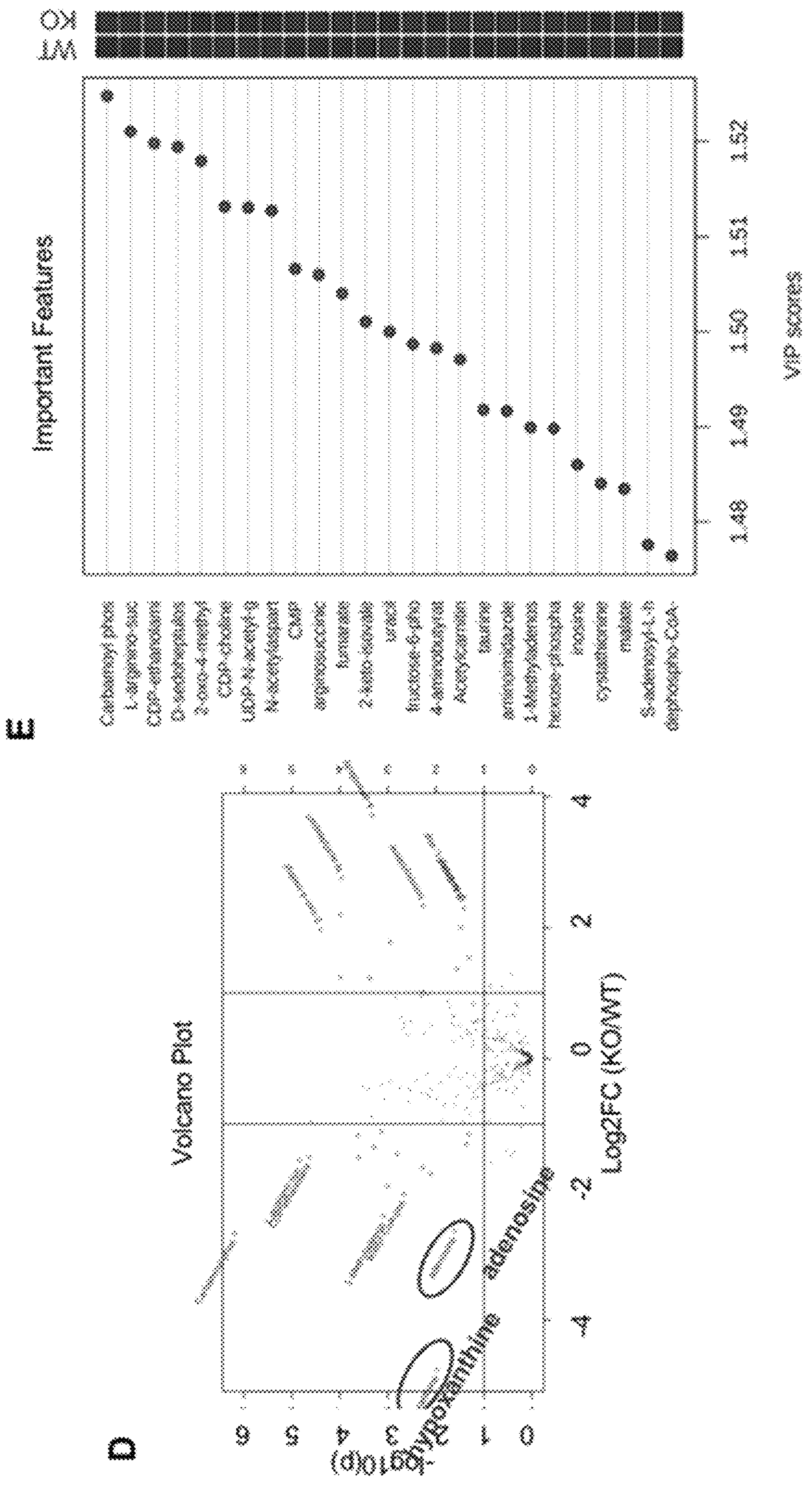

Due to the cellular dependency alteration of nucleotide synthesis pathway genes in Mll3/4 KO cells, we performed liquid-chromatography (LC) tandem mass spectrometry (MS/MS)-based steady-state metabolite profiling to globally assess the metabolome of WT and Mll3/4 KO cells (FIG. 9). Among the small molecules detected, the steady-state levels of metabolites involved in methionine metabolism (S-adenosylhomocysteine, homocysteine, cystathionine), urea cycle (argininosuccinate, carbamoyl-phosphate) and nucleotide metabolism (UMP, CMP, AICAR, carbamoyl-phosphate, inosine, adenosine, and hypoxanthine) were significantly altered in MLL3/4-deficient cells compared to wild-type cells (FIG. 9C-E). We note that, at the steady-state levels, information about the dynamic regulation of the metabolic pathways is not complete, and parallel approaches must be employed to reach a conclusion on whether the activity of a metabolic pathway is altered (19).

Because several metabolite intermediates involved in nucleotide metabolism were altered in Mll3/4 KO cells, we decided to focus our study on the role of MLL3/4 on nucleotide synthesis. Nucleotide metabolism is an essential metabolic process that enables the maintenance of cellular homeostasis. Nucleotides support nucleic acid and protein synthesis, energy preservation, signaling activity, and cytoskeletal function (16). Nucleotides can be produced through the de novo or salvage synthesis pathways. The de novo pathways utilize amino acids (such as glutamine and other small molecules) to build the purine and pyrimidine rings.

Figure 2:
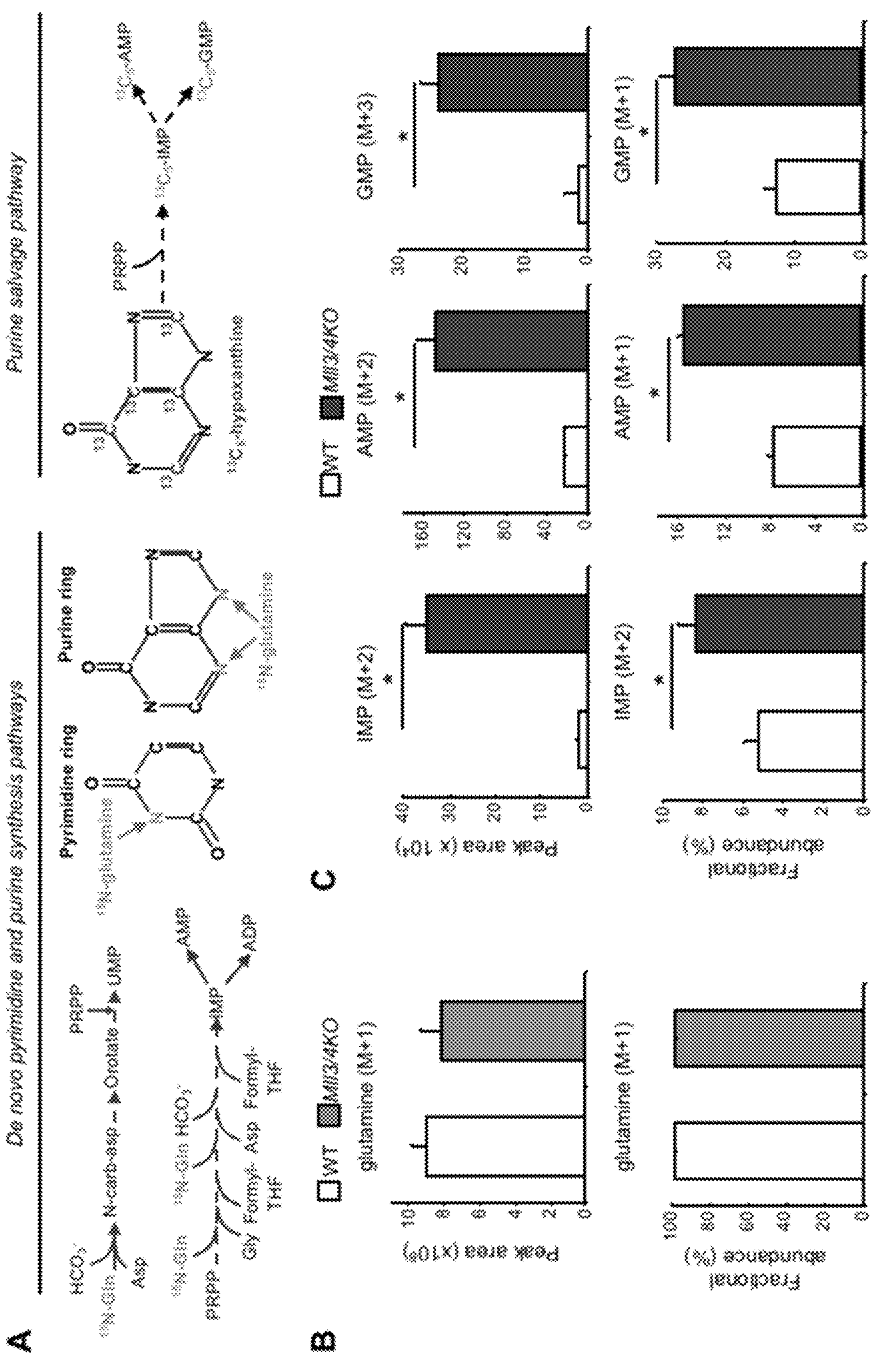
FIG. 2. Loss of MLL3 and MLL4 increases flux through purine synthesis in mESCs. (A) The flowchart of $^{15}N$ glutamine and $^{13}C$ hypoxanthine isotope tracing. (B) Tracer levels of glutamine (M+1) in WT and KO cells. (C) Labeled purine metabolite levels with $^{15}N$ glutamine tracing. (D) Labeled pyrimidine metabolite levels with $^{15}N$ glutamine tracing. (E) $^{13}C$ Hypoxanthine Tracing and labeled metabolite levels.
Figure 2:
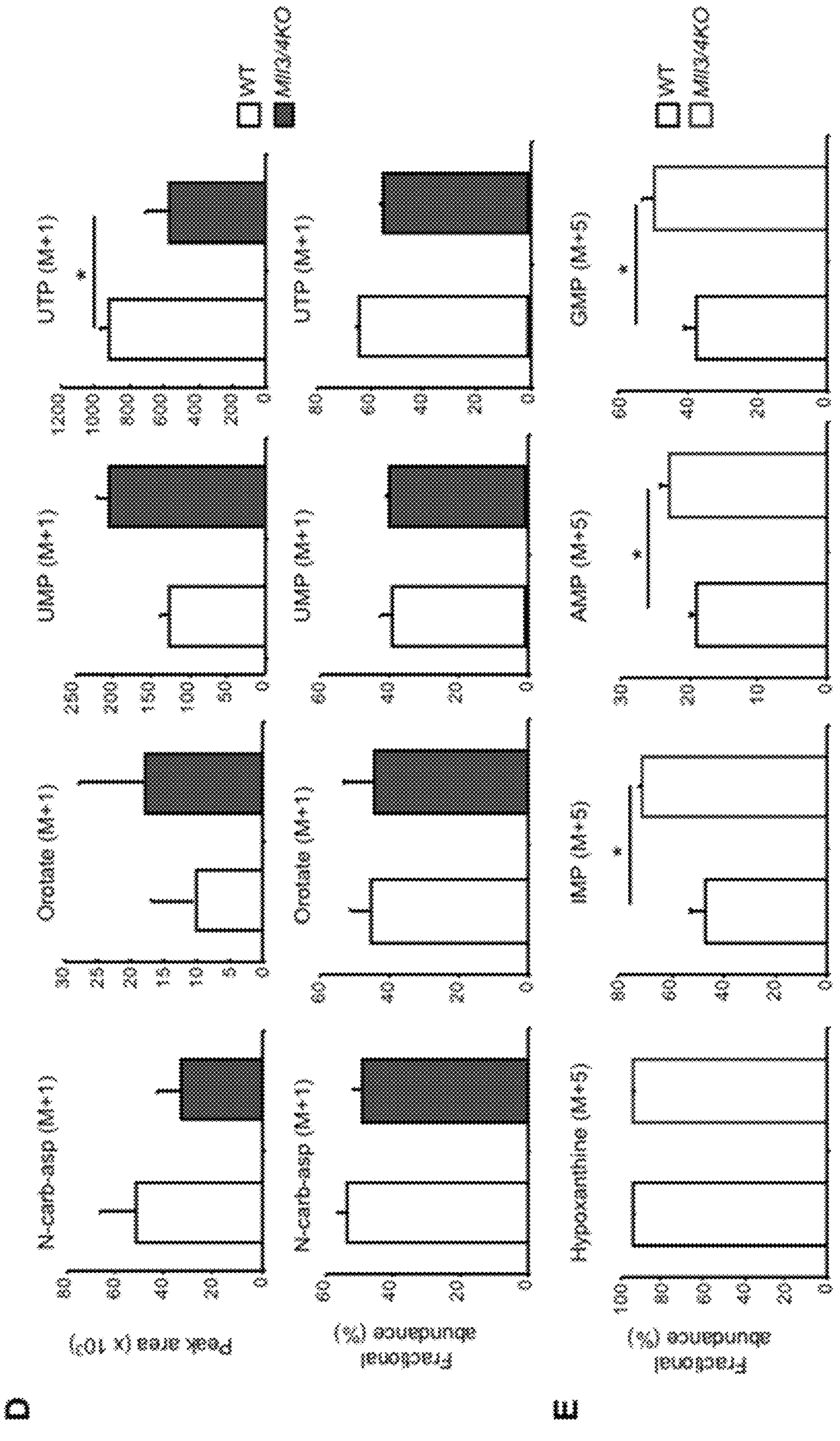

On the other hand, the purine salvage pathway recycles existing nucleosides and nucleobases such as hypoxanthine to maintain purine nucleotide pools. To further investigate whether changes in nucleotide levels observed in Mll3/4 KO cells reflect alteration in metabolic flux through the de novo or purine salvage pathways (FIG. 2A), we employed LC-MS-based isotope tracing ($^{15}$N-(amide)-glutamine and $^{13}$C-hypoxanthine). $^{15}$N-glutamine tracing study revealed that Mll3/4 KO cells exhibit increased flux through de novo purine synthesis but not significantly through de novo pyrimidine synthesis (FIG. 2B-D). Interestingly, $^{13}$C-hypoxanthine tracing study also showed that the purine salvage pathway is also slightly increased in Mll3/4 KO cells (FIG. 2E). Overall, these metabolic studies suggest that cells depleted of MLL3 and MLL4 have a higher flux through purine synthesis and are more dependent on purine metabolic pathway genes for survival.

Mll3/4 KO mESCs Confer Enhanced Sensitivity to Purine Synthesis Inhibition

Figure 10:
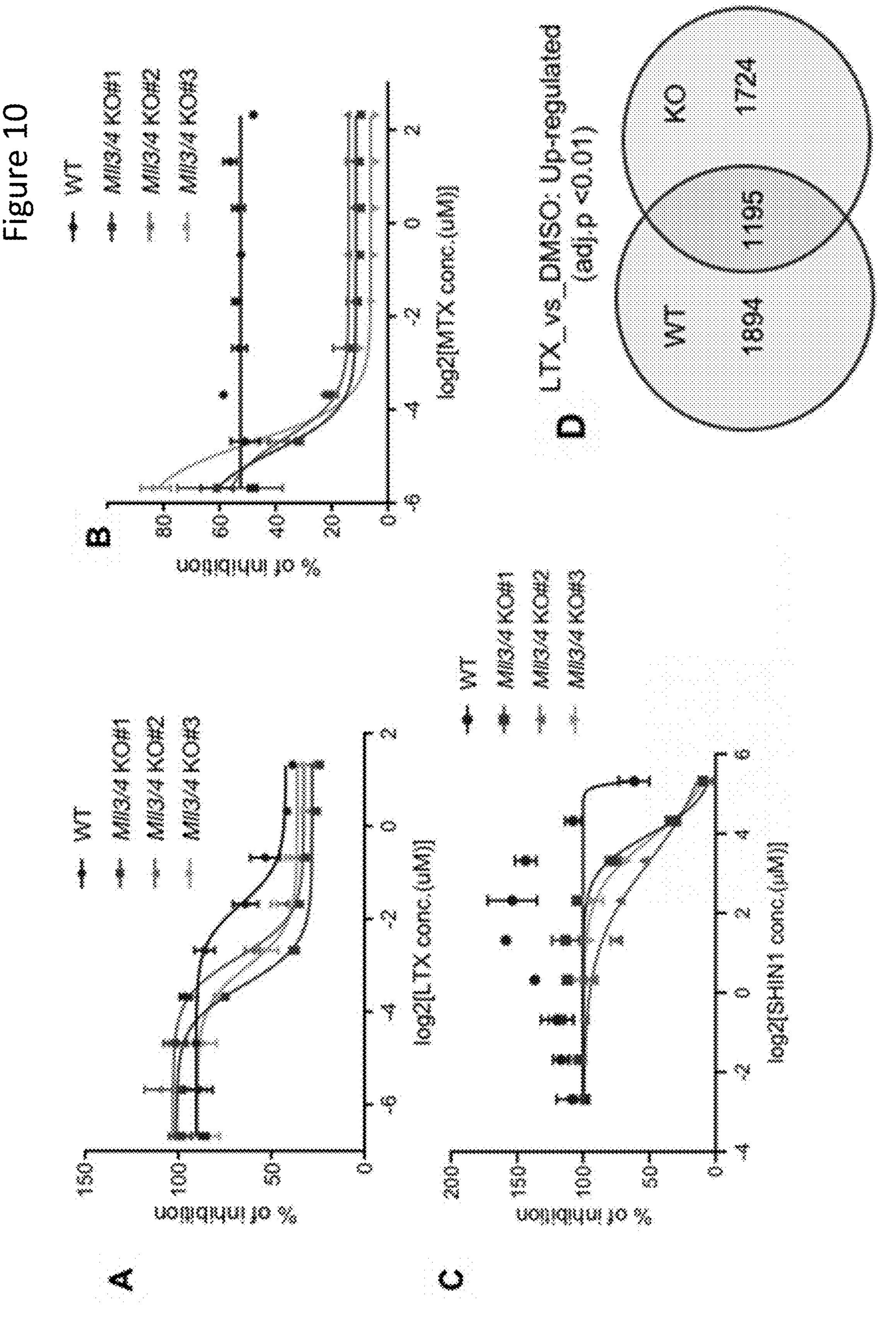
FIG. 10. Mll3/4 KO mESCs are more sensitive to purine synthesis inhibition. (A-B) WT and Mll3/4 KO cells were treated with 0-2.5 μM lometrexol (LTX) (A) or 0-5 μM methotrexate (MTX) (B) for 48 hours. CellTiter-Glo® luminescent cell viability assay was performed to determine the percentage of inhibition under these conditions with three different Mll3/4 KO clones included. (C) WT and Mll3/4 KO cells were treated with 0-40 μM SHIINI for 48 hours. MTT cell viability assay was performed to determine the percentage of inhibition under these conditions with three different Mll3/4 KO clones included. (D) Venn diagram showing the overlapped upregulated genes with LTX treatment in WT and KO cells. (E) Pathway enrichment analysis of the commonly upregulated genes in WT and KO cells with LTX treatment. (F) Pathway enrichment analysis of uniquely upregulated genes in WT cells with LTX treatment. (G) Pathway enrichment analysis of uniquely upregulated genes in Mll3/4 KO cells with LTX treatment.
Figure 10:
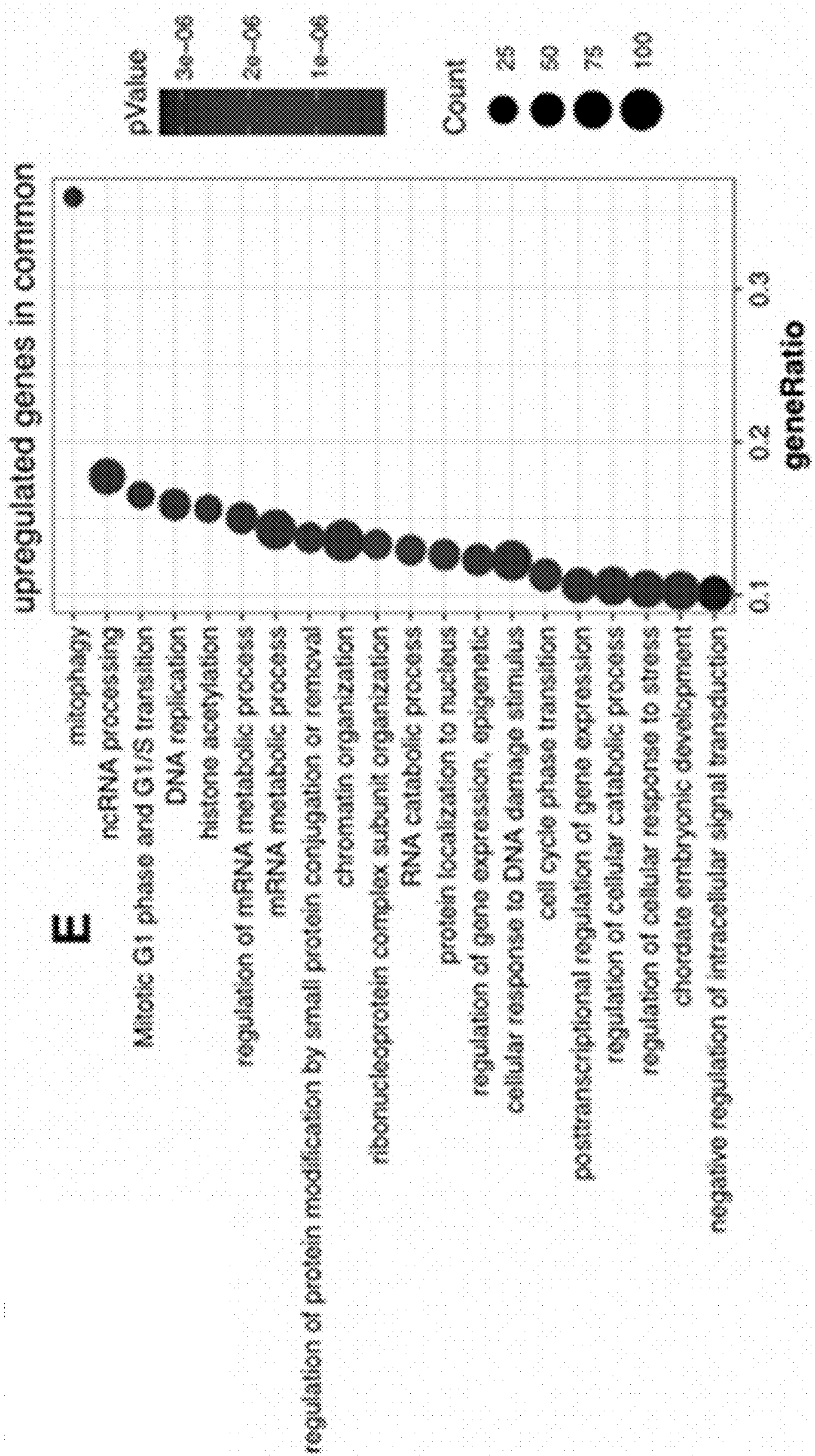
Figure 10:
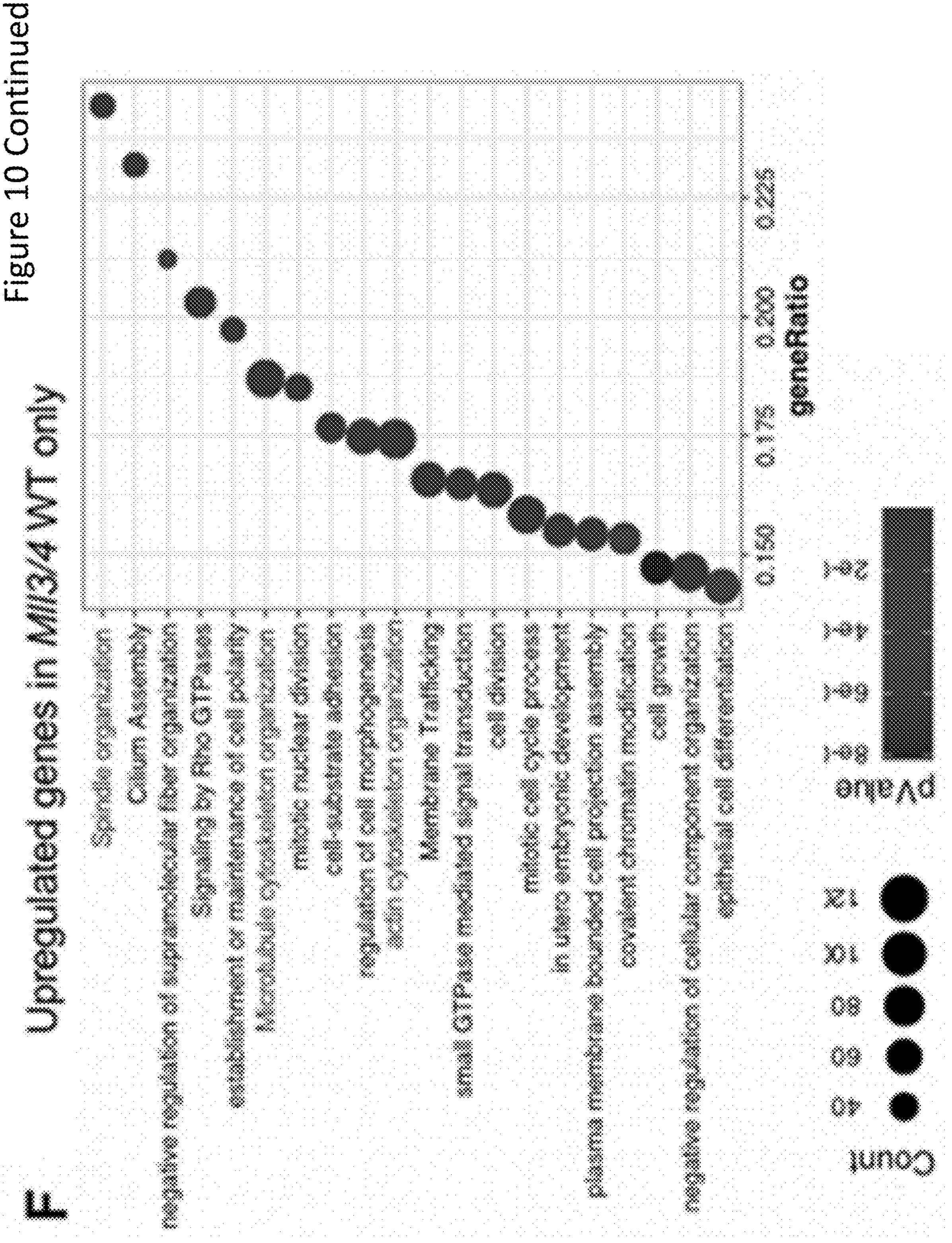
Figure 10:
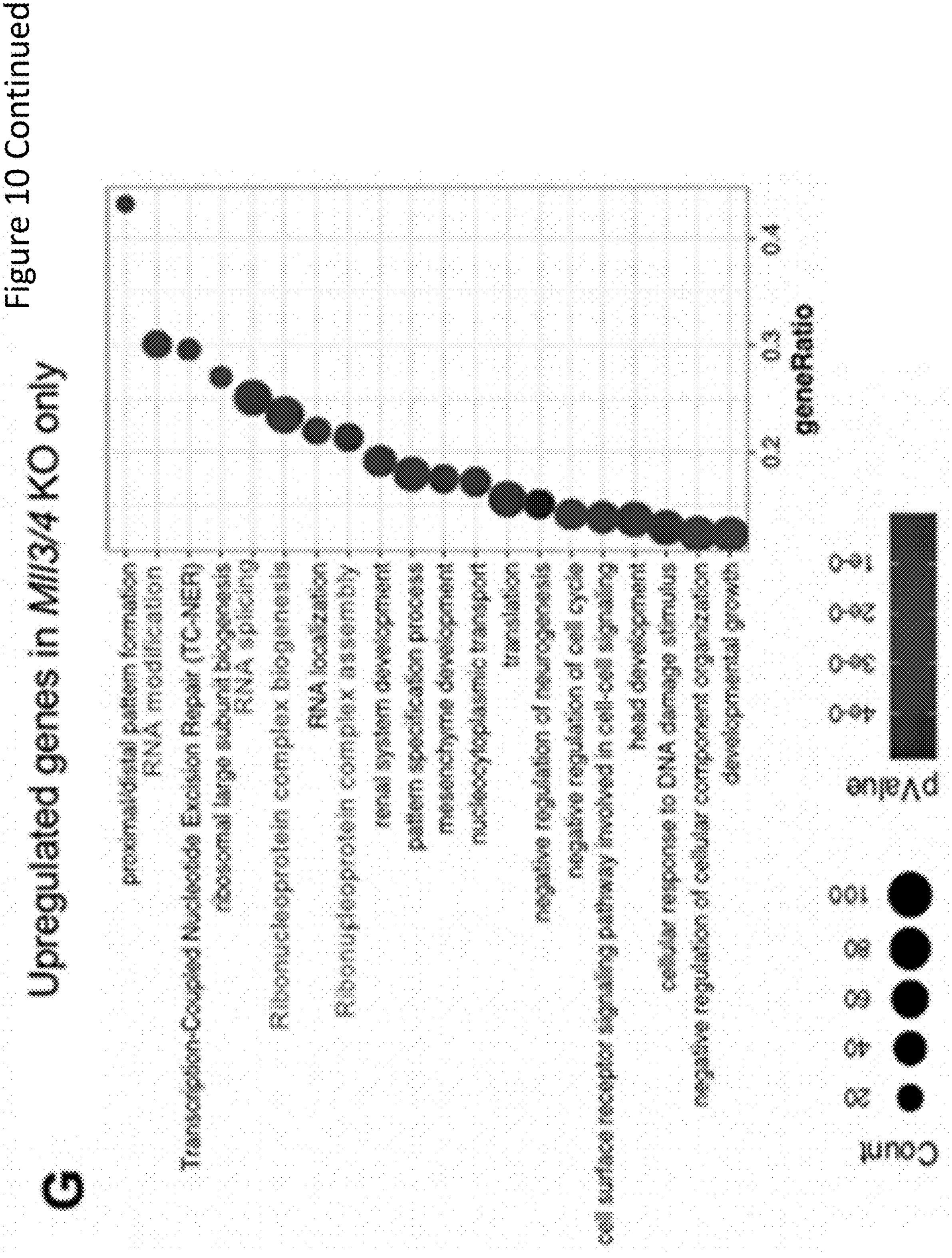

We hypothesized that Mll3/4 KO cells should have enhanced sensitivity to purine synthesis inhibition due to the metabolic dependency shift towards purine nucleotide synthesis pathways. WT and Mll3/4 KO cells were treated with lometrexol (LTX), a de novo purine synthesis inhibitor targeting glycinamide ribonucleotide formyltransferase (GART). On the other hand, hypoxanthine (HPX), one of the nucleobases for purine salvage pathway, was added to rescue the purine synthesis inhibition by LTX (FIG. 3A). We observed elevated sensitivity to LTX in Mll3/4 KO cells, and the cell growth and/or viability inhibition was completely rescued by HPX (FIG. 3A, FIG. 10A). If Mll3/4 KO cells gain sensitivity to de novo purine synthesis inhibition, we hypothesize that these cells lacking MLL3 and MLL4 should also be sensitive to pathway inhibition upstream of purine synthesis including folate-mediated one-carbon (1C) metabolism. Indeed, Mll3/4 KO cells showed enhanced sensitivity to methotrexate (MTX) and SHIN1 (FIG. C). MTX targets dihydrofolate reductase (DHFR) and de novo purine synthesis, and SHIN1 inhibits serine hydroxymethyltransferase 1 and serine hydroxymethyltransferase 2 (SHMT1/2), which further demonstrated the metabolic rewiring in Mll3/4 KO cells. In order to elucidate the differential sensitivity of LTX treatment in the presence or absence of MLL3/4, we performed RNA-seq to compare the gene expression change in WT and KO cells in response to LTX and/or HPX treatment (FIG. 3B). Interestingly, principal component (PC) analysis showed that the majority of variance of gene expression was explained by PC1 (94%) which was separated by the genotype of mESCs (WT or Mll3/4 KO) (FIG. 3C). HPX alone elicited subtle gene expression or phenotypic change, whereas LTX treatment induced significant gene expression change which was almost completely rescued by HPX in both WT and Mll3/4 KO cells (FIG. 3C). The differentially expressed genes in WT and KO cells were also uniquely altered in response to LTX treatment, with a more prominent effect in KO cells (FIG. 3D). A significant number of the upregulated genes in KO cells were further elevated by LTX treatment (top cluster in KO_LTX group), while downregulated genes in KO cells were further depressed (bottom cluster in KO_LTX group) (FIG. 3D). The differential sensitivity to LTX treatment promoted us to investigate the unique gene expression changes between WT and KO cells. First, we found 1063 genes commonly downregulated with LTX treatment in WT and KO cells (FIG. 3E). The pathway analysis demonstrated these genes enriched in biological processes related to amino acid and cofactor metabolism, which was an expected outcome of purine synthesis inhibition by targeting GART (FIG. 3F). When analyzing the pathway enrichment of uniquely downregulated genes in WT cells with LTX treatment, we identified processes related to RNA and its metabolism (FIG. 3G). In contrast, the uniquely downregulated genes in Mll3/4 KO cells with LTX treatment were enriched in pathways related to actin filament-based process and microtubule cytoskeleton organization (FIG. 311). On the other hand, there were 1195 genes commonly upregulated with LTX treatment (FIG. 10D), and they were enriched in a variety of biological processes including chromatin organization, cellular response to DNA damage, and stress stimulus (FIG. 10E). Another interesting observation was that the enriched pathways for the uniquely upregulated genes in WT and KO cells were reciprocal to that of downregulated genes (FIG. 10F, G). The distinct gene expression signature changes in the presence or absence of Mll3/4 may predict the differential sensitivity to LTX treatment.

Figure 11:
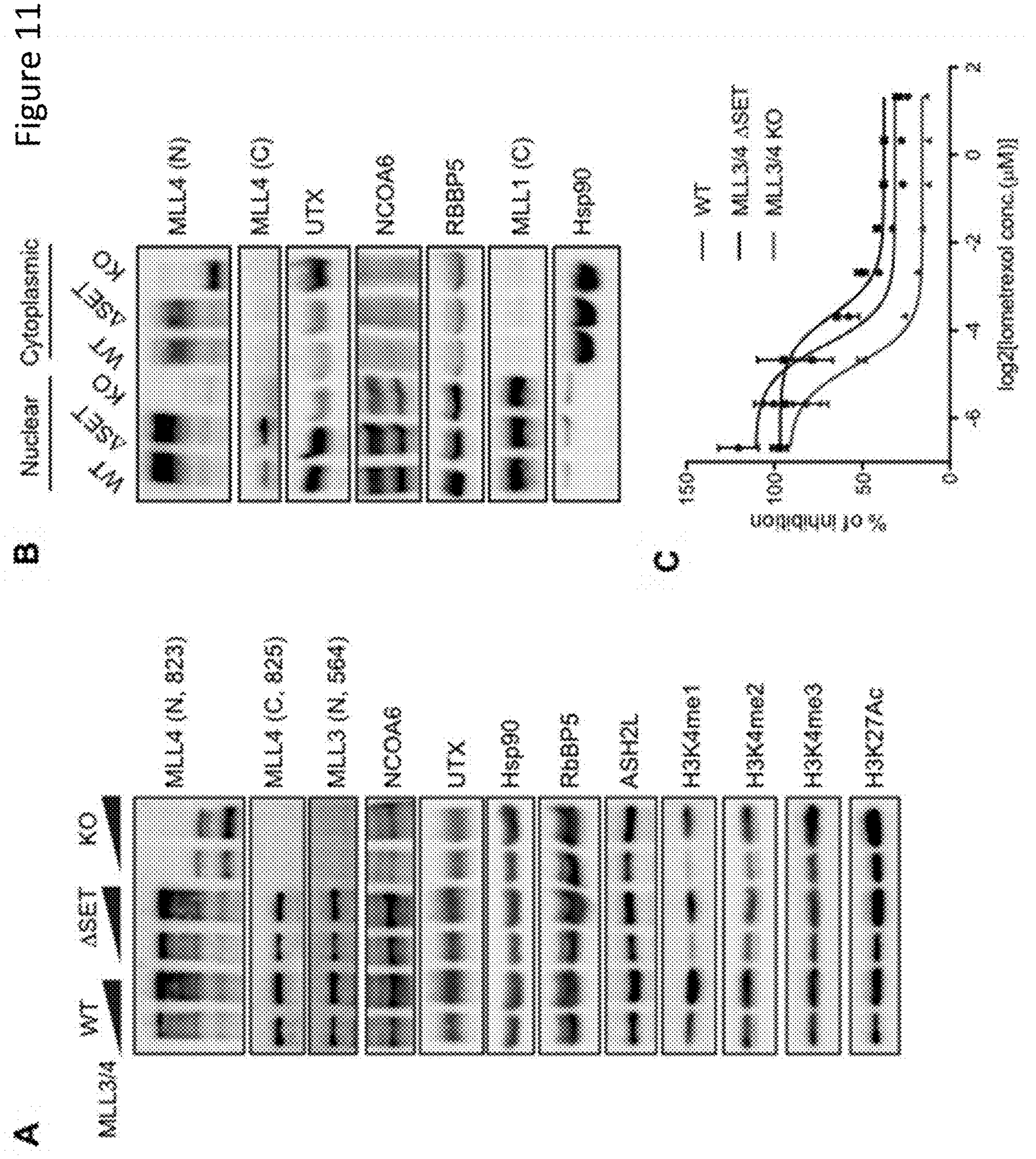
FIG. 11. SET domain of MLL3/4 does not confer sensitivity difference to purine synthesis inhibition. (A) Western blot showing MLL4, MLL3, NCOA6, UTX, RbBP5 and ASH2L protein levels in WT, MLL3/4 ΔSET and MLL3/4 KO cells with Hsp90 as the loading control. Bulk levels of histone H3K4me1, H3K4me2, H3K4me3 and H3K27Ac were also shown. N, N-terminus; C, C-terminus. mESCs harboring deletion of the SET domains of both MLL3 and MLL4 (referred to as MLL3/4 ΔSET) were generated in our previous studies (20). (B) Western blot showing nuclear and cytoplasmic MLL4, UTX, NCOA6 and RBBP5 protein levels after cell fractionation, with MLL1 and Hsp90 serving as nuclear and cytoplasmic loading control. (C) WT, MLL3/4 ΔSET and MLL3/4 KO cells were treated with 0-2.5 μM lometrexol (LTX) for 72 hours. CellTiter-Glo® luminescent cell viability assay was performed to determine the percentage of inhibition.

To investigate whether the elevated purine biosynthesis inhibition sensitivity is due to the loss of catalytic dependent or independent activity, we compared the LTX treatment in WT, MLL3/4 ΔSET (20), and MLL3/4 KO cells. Loss of SET domains did not affect COMPASS subunits stability specific to MLL3/4 including NCOA6 and UTX, but the bulk levels of H3K4me1 and H3K4me2 were reduced to a similar level in MLL3/4 ΔSET and MLL3/4 KO cells compared with WT cells (FIG. 11A). Of note, the shift of UTX proteins from nucleus to cytosol compartment and the downregulation of NCOA6 were also only observed in complete KO cells not MLL3/4 ΔSET cells (FIG. 11B). Finally, we showed the sensitivity to LTX of MLL3/4 KO cells is largely due to the catalytic independent activities of MLL3/4, as MLL3/4 ΔSET cells exhibited indistinguishable sensitivity to LTX in comparison to WT mESCs (FIG. 11C).

Figure 12:
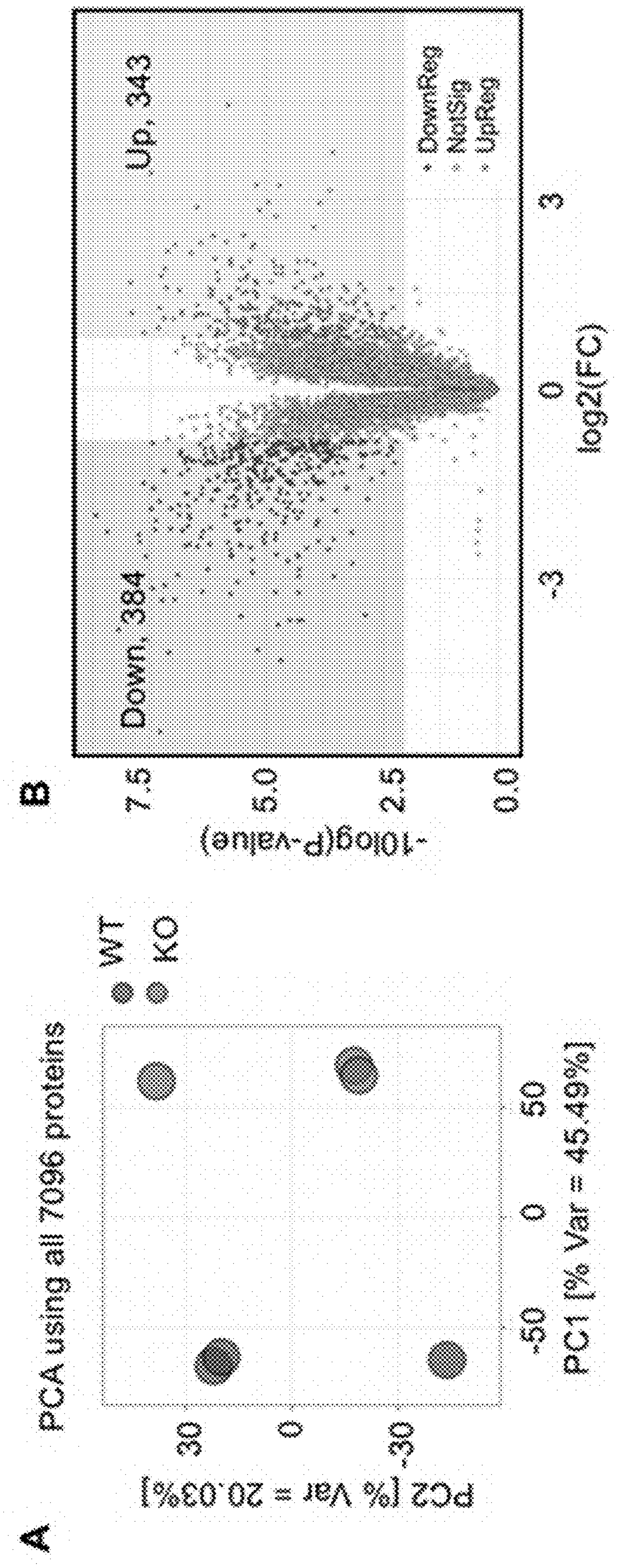
FIG. 12. TMT proteomics study identified purine metabolism upregulation in Mll3/4 KO cells. (A) TMT proteomics study was conducted in WT and Mll3/4 KO cells. PCA plot showing the separation of genotype by PC1 using all 7096 proteins identified. (B) Volcano plot showing all the differentially present proteins in WT and KO cells with the cutoff |FC|>1.75, p.val<0.01. Up, 343 proteins; Down, 384 proteins. (C) Protein levels of MLL3/4 COMPASS subunits identified and quantified by TMT approach. (D) Pathway enrichment analysis of the downregulated proteins in KO cells in comparison to WT cells. (E) Pathway enrichment analysis of the upregulated proteins in KO cells in comparison to WT cells. (F) Heatmap showing the 59 proteins in Group1 change in WT and KO cells related to nucleotide metabolic processes.
Figure 12:
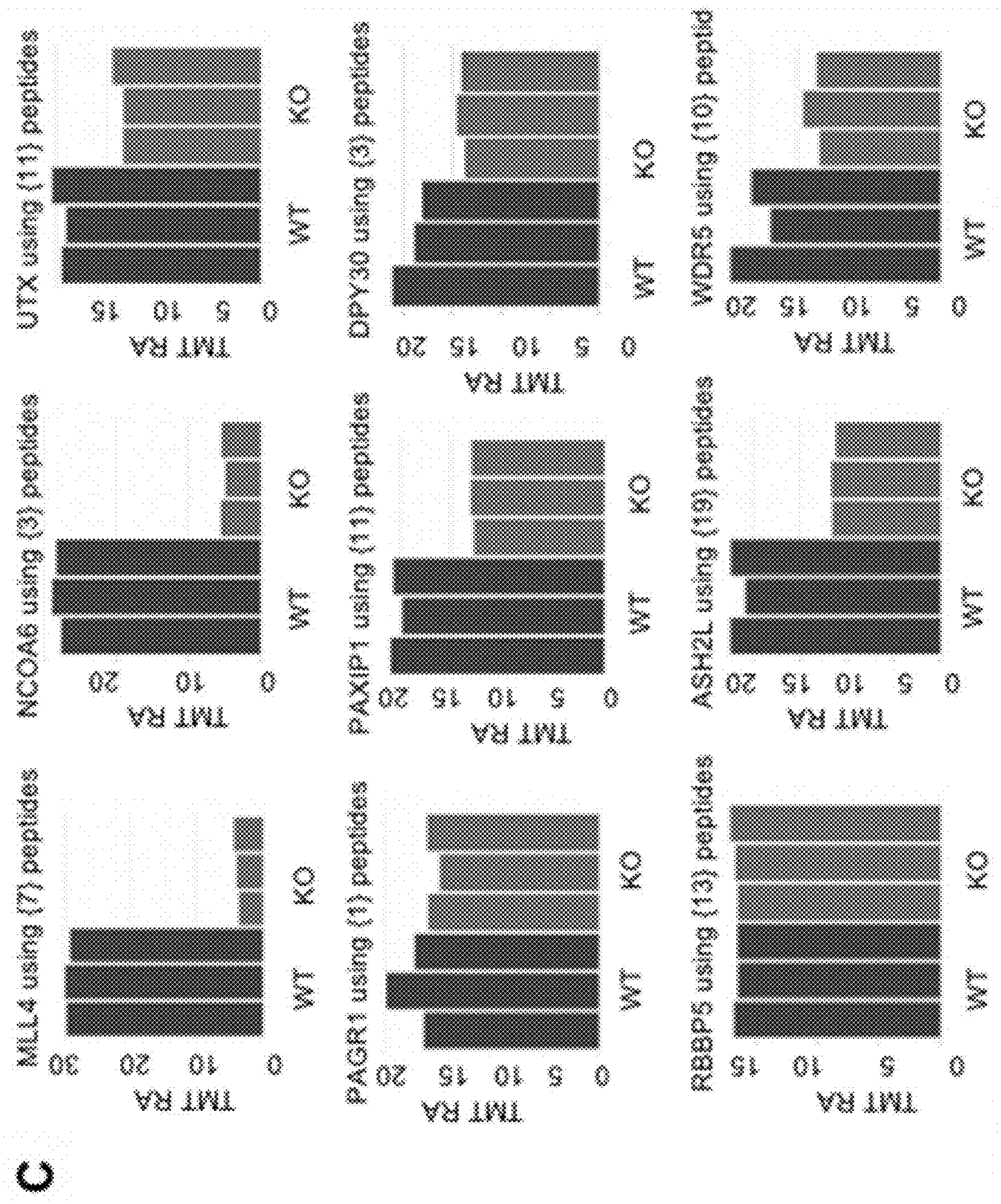
Figure 12:
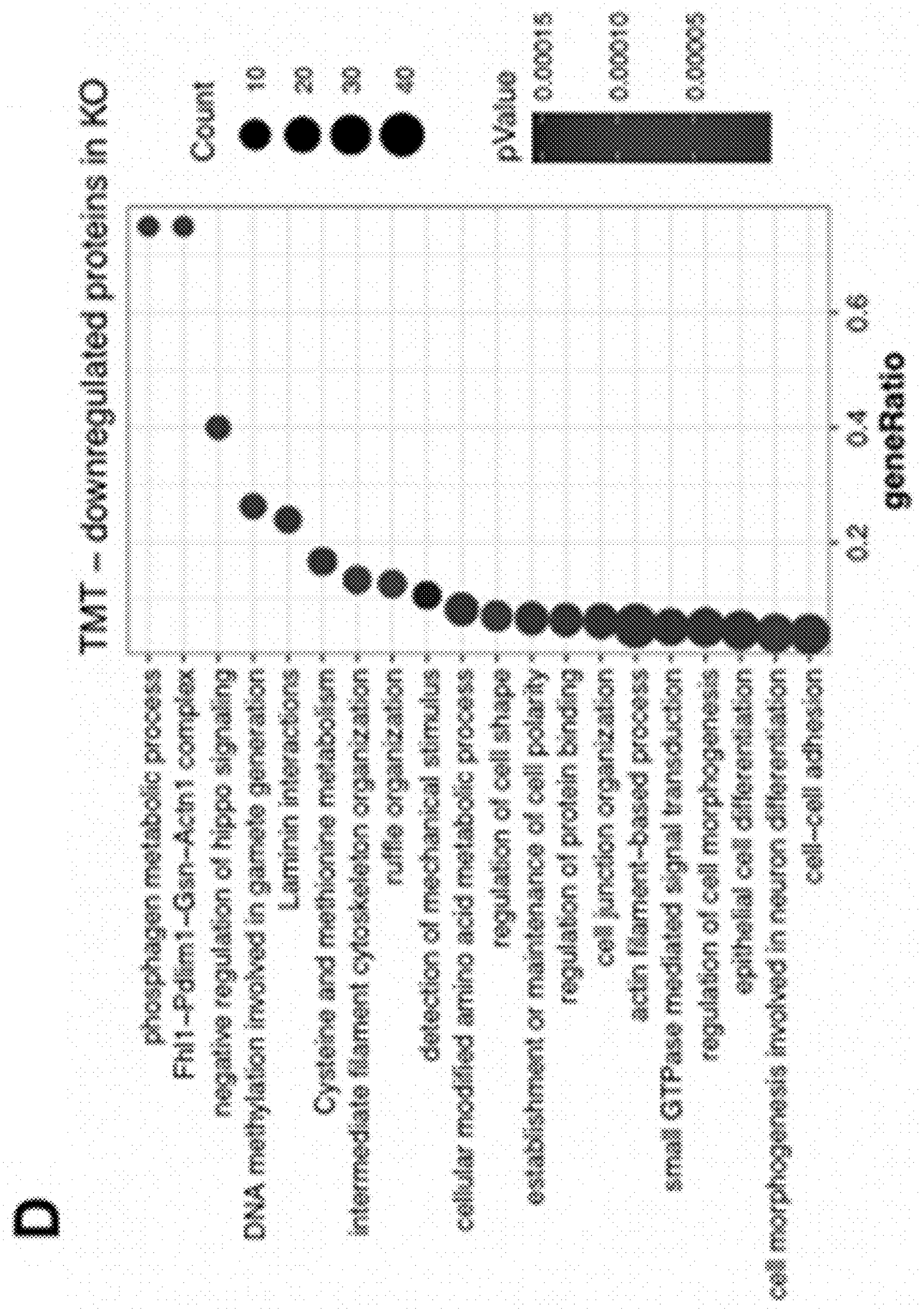
Figure 12:
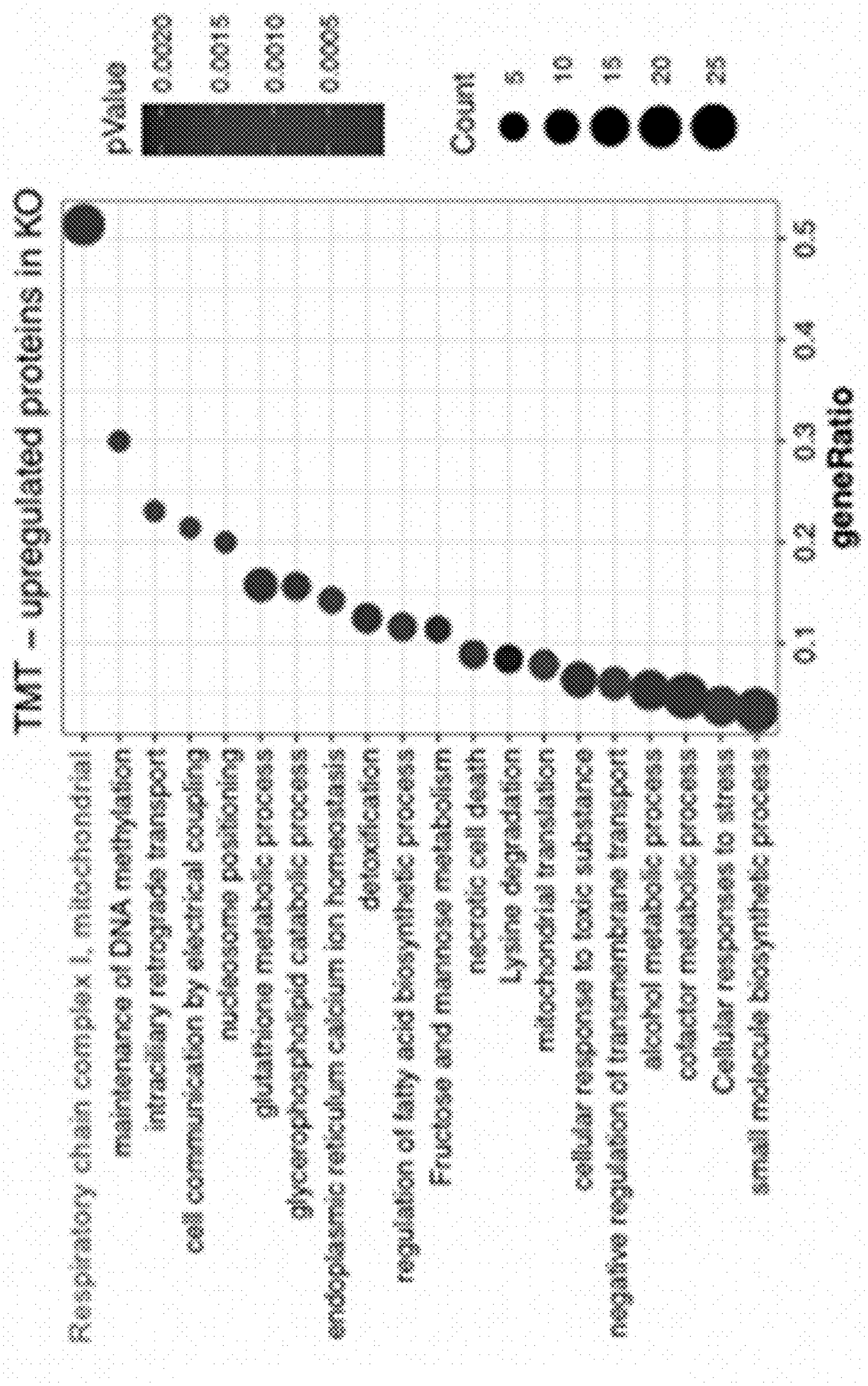
Figure 12:
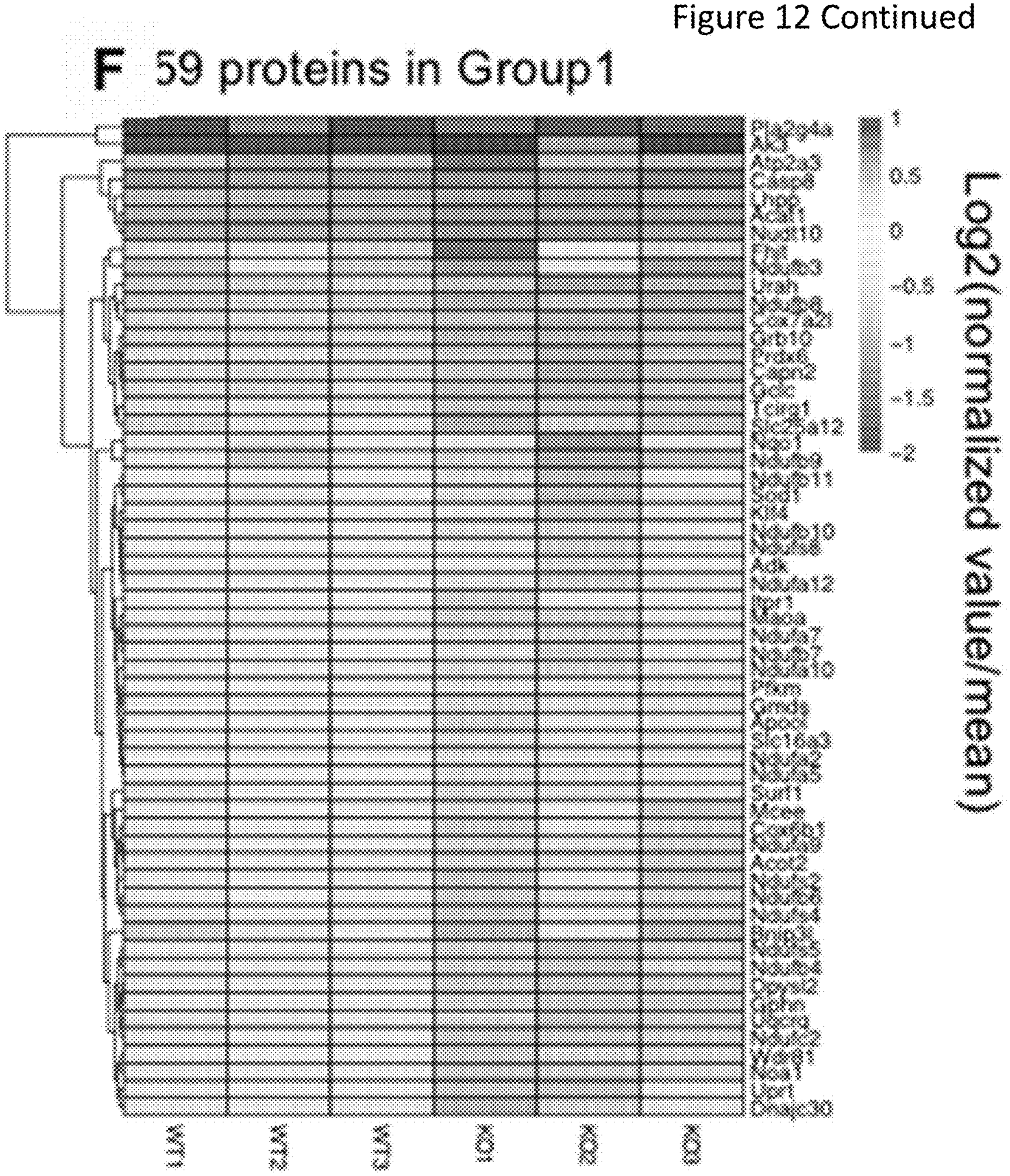

A Tandem Mass Tag (TMT) Proteomics Profiling Identifies Purine Metabolism Possessive Upregulation in Mll3/4 KO Cells Due to the profound change in gene expression in WT and KO cells (~4500 down- or upregulated genes with adj.p<0.01), it is difficult to dissect what are the most significant gene/protein signature changes that lead to the metabolic dependency shift and other cellular defects seen in Mll3/4 KO cells. As a complement of RNA-seq approach to identify the transcriptomics change, we took TMT proteomics approach to quantify the total protein level alteration between WT and Mll3/4 KO cells. In summary, we identified 7,379 total collapsed proteins, 7,096 quantified proteins, and 57,479 quantified peptides. PC analysis demonstrated the separation of genotype by PC1 using all 7096 proteins identified in TMT (FIG. 12A). A stringent cutoff (fold change >1.75, p.val<0.01) identified 343 proteins upregulated and 384 proteins downregulated in Ml13/4 KO cells (FIG. 12B). We further confirmed that protein levels of MLL3/4 COMPASS identified and quantified by TMT approach were consistent with our previous Western blot analysis with significant diminished levels of MLL4 (Kmt2d), NCOA6, UTX (Kdm6a), and PTIP (Paxip1) (FIG. 7B and FIG. 12C). Pathway enrichment analysis of the downregulated proteins in KO cells showed several processes related to cytoskeleton organization, cell shape regulation, cell junction organization, and cell-cell adhesion (FIG. 12D), and the terms were consistent with the MLL4 peak annotation with KEGG pathway enrichment analysis (FIG. 7E). Among the biological processes of annotated as upregulated genes in Mll3/4 KO cells, there was significant enrichment of the mitochondrial respiratory chain complex I pathway (FIG. 12E). The identity of sub-terms in this group (Group 1) were all related to nucleotide metabolic pathways (FIG. 4A), in accordance with the increased de novo purine synthesis and purine salvage upregulation in MLL3/4 KO cells (FIG. 3C, E). It is important to note that a major function of mitochondrial electron transport chain, which is also upregulated, is to support nucleotide metabolism (21). Further, the heatmap revealed 59 proteins in Group1 change between WT and KO cells related to purine nucleotide metabolic processes (FIG. 12F), suggesting Mll3/4 KO cells also exhibited elevated expression levels of purine metabolism genes. Collectively, we observed that loss of MLL3/4 functions rewired cells to require higher demand for purine and/or pyrimidine nucleotide synthesis for viability and survival.

Figure 13:
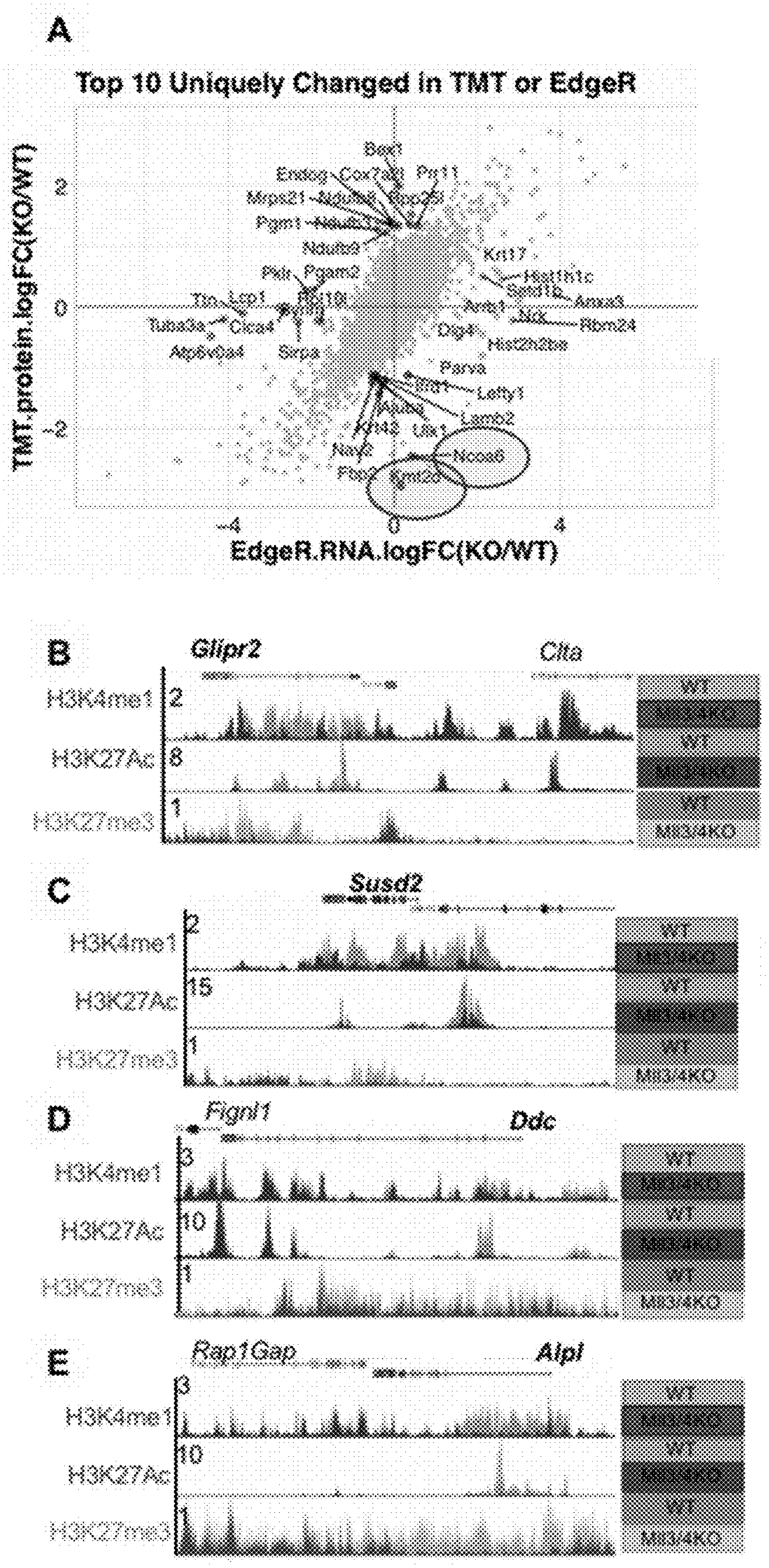
FIG. 13. RNA-seq and TMT proteomics profiling integration identified top Mll3/4 target genes. (A) The correlation analysis of TMT and EdgeR data identified factors that were only altered at protein levels but not RNA levels including NCOA6. (B-E) Browser tracks of H3K4me1, H3K27Ac, and H3K27me3 ChIP-seq selected for downregulated target genes with transparent view including Glipr2 (B), Susd2 (C), Ddc (D), and Alpl (E). (F) Knockdown efficiency of each specific target shown by the z-score heatmap. (G) Percentage of commonly regulated genes with Mll3/4 with respect to each target knockdown.
Figure 13:
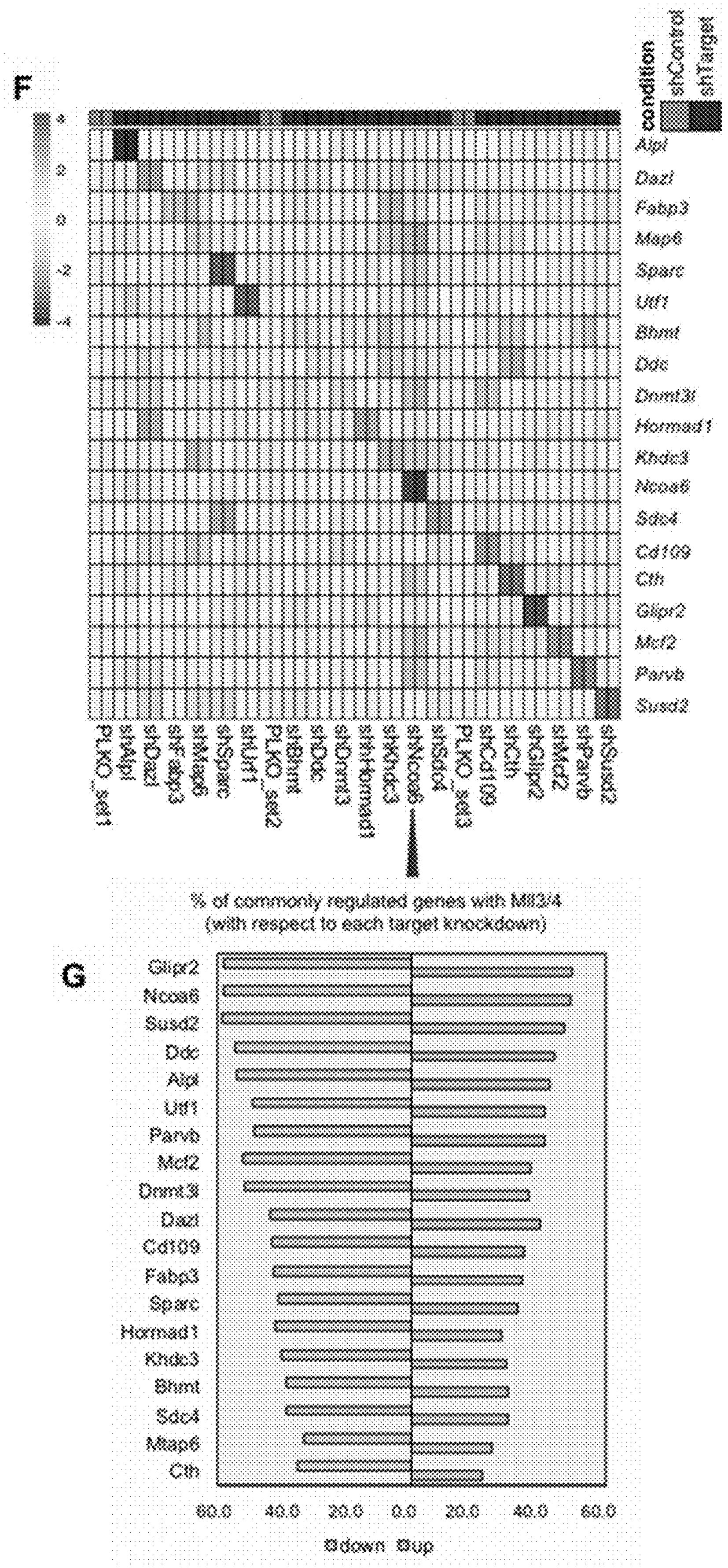

Identification of Suppression of Purine Metabolism Pathway with Integration Study of TMT, RNA-Seq and Hi-C We integrated RNA-seq transcriptomics and TMT proteomics study to seek the top target genes of MLL3/4 and determine the transcriptional clue for purine metabolism genes' regulation. An overall consistency of RNA and protein changes was shown with a correlation of 0.797 (FIG. 4B). Using the RNA and protein correlation plot, we also identified factors with protein level change but not RNA, including MLL4 and NCOA6 (FIG. 13A). The top 20 down-regulated targets with both RNA and protein levels were selected for further functional analyses (FIG. 4B). These genes were likely to be the direct transcriptional targets of MLL3/4; a significant reduction of H3K4me1 and H3K27Ac and an increase of H3K27me3 were found surrounding the enhancers of these genes (FIG. 13B-E). Next, we knocked down each of the 18 genes with shRNAs and analyzed the RNA-seq data after batch removal (except for Rnf213 and Dppa3, due to the unavailability of efficient shRNAs) (FIG. 13F). Ncoa6 was also included as a control since it was the most down-regulated COMPASS subunit when MLL3/4 were depleted (FIG. 7B, FIG. 12C and FIG. 13A). First, we confirmed the knockdown efficiency of individual shRNAs (FIG. 13F). Interestingly, Ncoa6 knockdown also led to the downregulation of most of these top MLL3/4 targets (FIG. 13F). A significant overlap of gene regulation was found with Ncoa6 knockdown and Mll3/4 depletion, reassuring the co-function of MLL3/4 and NCOA6 (FIG. 13G). Then, we analyzed the set of purine metabolism genes' expression, which were elevated after MLL3/4 depletion (FIG. 12F). A collection of genes knockdown showed partial upregulation of the purine metabolism gene set (including Map6, Khdc3, Ghpr2, Mcf2, Susd2, and Ncoa6) (FIG. 4C). A number of these MLL3/4 targets were involved in the spindle and cytoskeletal function, suggesting that the change of cell shape and cell state may ultimately drive the metabolic dependency change when the activity of MLL3/4-COMPASS is impaired.

Figure 14:
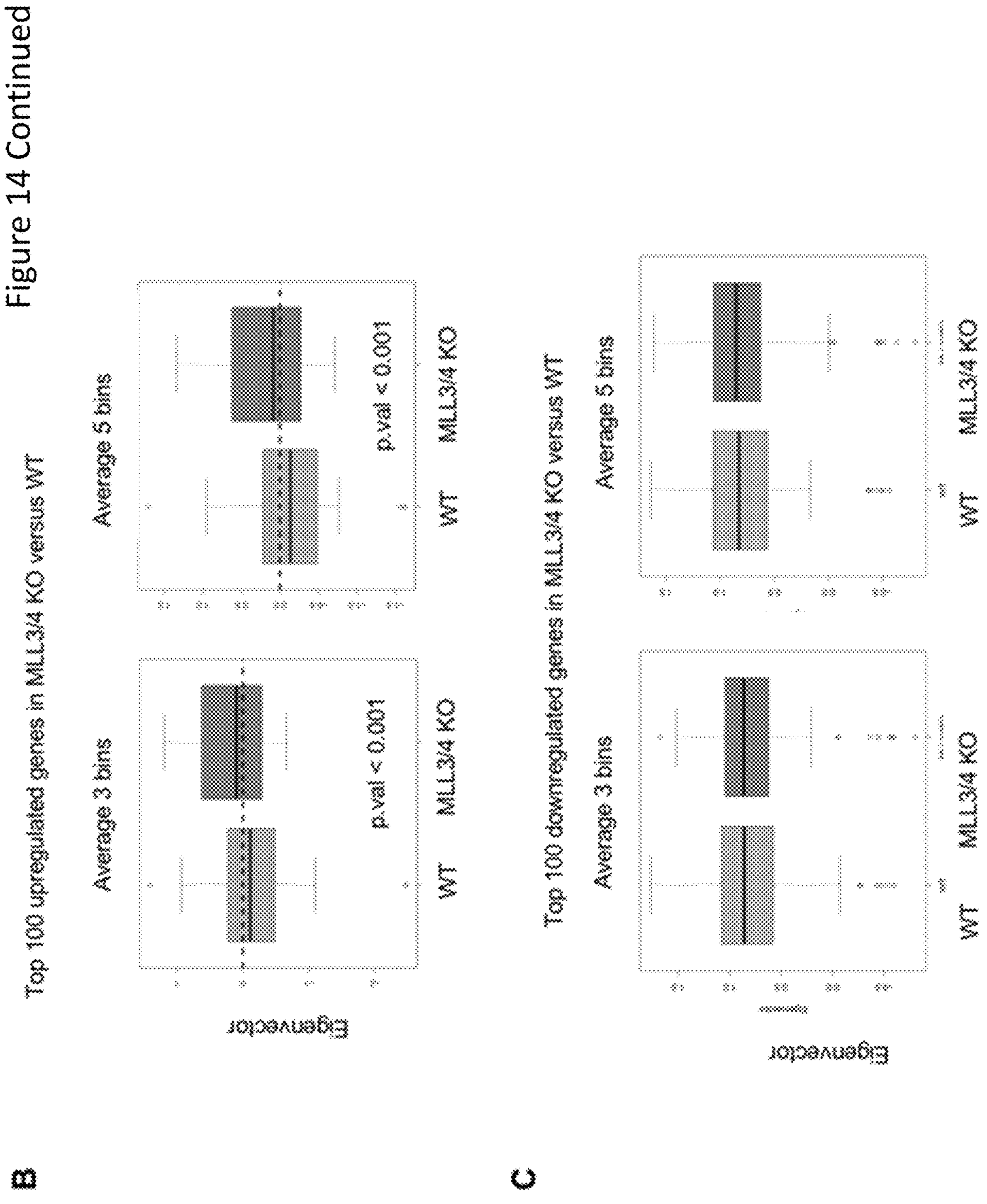
FIG. 14. Hi-C analysis in WT and Mll3/4 KO mESCs. (A) Loop number, TAD number, and AB compartment number in WT and Mll3/4 KO mESCs. (B-C) Eigenvector for top 100 up (B) or down (C) regulated genes. 3 bins average is the average of the 100 kb bin where the gene's TSS is located and the adjacent two bins; 5 bins average is the average of the 100 kb bin where the gene's TSS is located and the adjacent four bins.

Another bold assumption of the metabolism reprogramming in MLL3/4 deficient cells is the consequence of the higher order chromatin structural change due to MLL3/4 loss. To investigate this potential mechanism, we performed Hi-C in WT and MLL3/4 KO mESCs to explore the relationship between chromatin structure and epigenetic alterations in defining the metabolic rewiring. The loop number increased from 10,118 to 13695, when MLL3/4 are depleted, as well as the B to A compartment shifting (FIG. 14A). To quantitate and visualize compartment strength, we plotted interaction frequencies along the first eigenvector to generate compartmentalization saddle plots (FIG. 4D, E). The results revealed that the strength of A-A interactions was gained while the strength of B-B interactions was diminished in MLL3/4 KO cells (FIG. 4D, E). Majority of A and B genomic compartments are unaltered upon MLL3/4 depletion, but shifted regions primarily undergo decompaction and B to A compartment shifting (6.79% of B to A, and 2.01% of A to B) (FIG. 4F). To correlate the gene expression with the AB compartment shifting, we examined the gene expression change located at the B-A and A-B shifted compartments found in FIG. 4F. A significant upregulation of gene expression was observed in MLL3/4 KO cells when they are located within B-A shifted compartments, whereas gene expression was largely unaffected in stable and A-B shifted compartments (FIG. 4G). Consistently, the eigenvector of the top upregulated genes' TSS in MLL3/4 KO cells was significantly higher than WT cells (FIG. 14B). In contrast, the eigenvector of the top downregulated genes' TSS in MLL3/4 KO cells remained the same as WT cells (FIG. 14C). In summary, the higher order chromatin structure change due to MLL3/4 loss adds another layer of gene expression control and contributes to the metabolic conversion.

Figure 15:
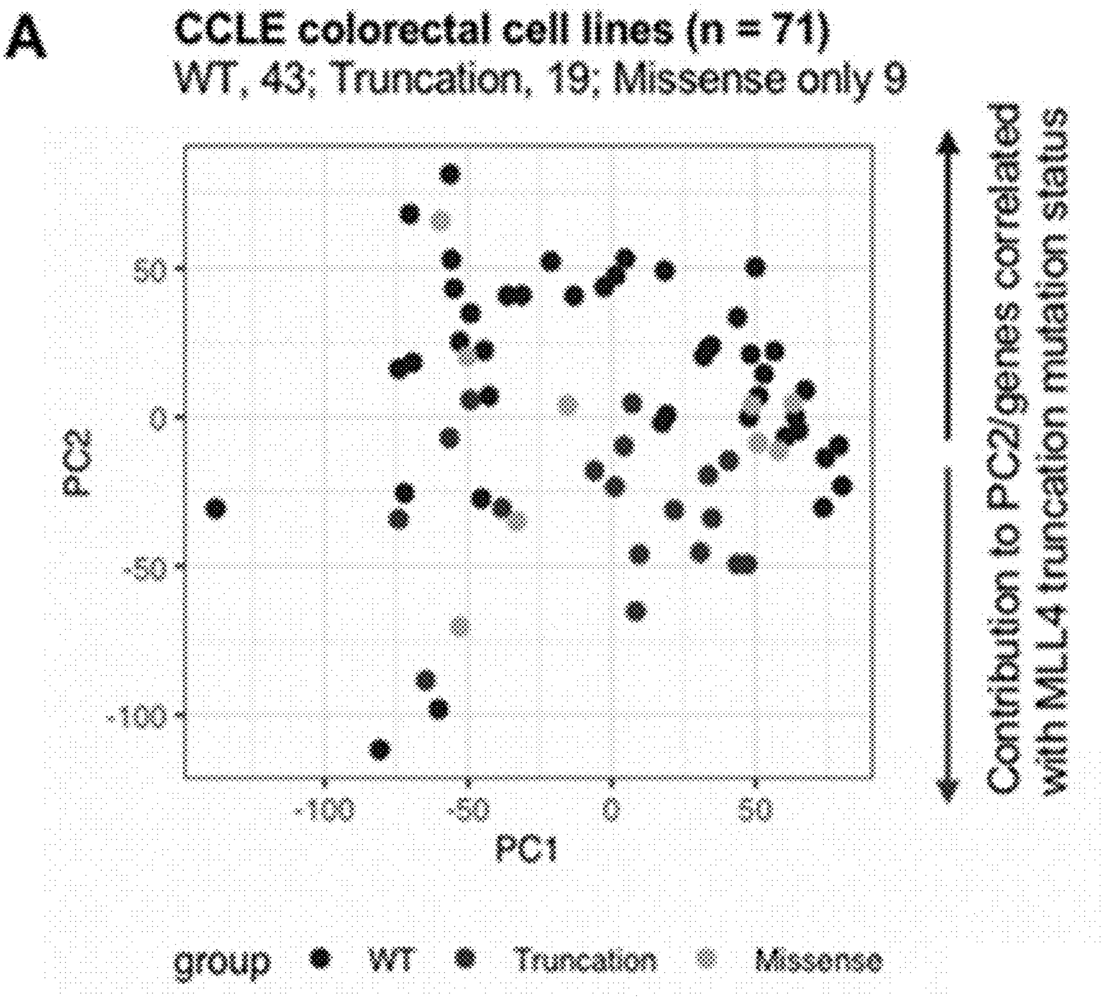
FIG. 15. Loss-of-function MLL4 mutation in colorectal cancer shares similar gene expression features with mESC depleted of MLL3/4. (A) PCA of 71 colorectal cancer cell lines of Cancer Cell Line Encyclopedia (CCLE) based on RNA-seq gene-expression data from DepMap. Cell lines were grouped based on the MLL4 mutation status: WT, n=43; Truncation, n=19; Missense only, n=9. If truncation mutation and missense mutation co-exist in one cell line, it is annotated as truncation. PC1, 24% variance; PC2, 11% variance. (B) Pathway analysis of downregulated genes of MLL4 truncation versus WT in CCLE colorectal cancer cell lines. (C) Pathway analysis of upregulated genes of MLL4 truncation versus WT in CCLE colorectal cancer cell lines. (D) Pathway analysis of downregulated genes of MLL4 truncation versus WT in patient samples from TCGA Pan-Cancer Atlas. (E) Pathway analysis of upregulated genes of MLL4 truncation versus WT in patient samples from TCGA PanCancer Atlas. (F) Pathway analysis of commonly downregulated genes of MLL4 truncation versus WT in both CCLE colorectal cancer cell lines and patient samples from TCGA PanCancer Atlas. Data were retrieved from cBioPortal with OQL (Onco Query language) to define MLL4 mutation status (https://www.cbioportal.org/).
Figure 15:
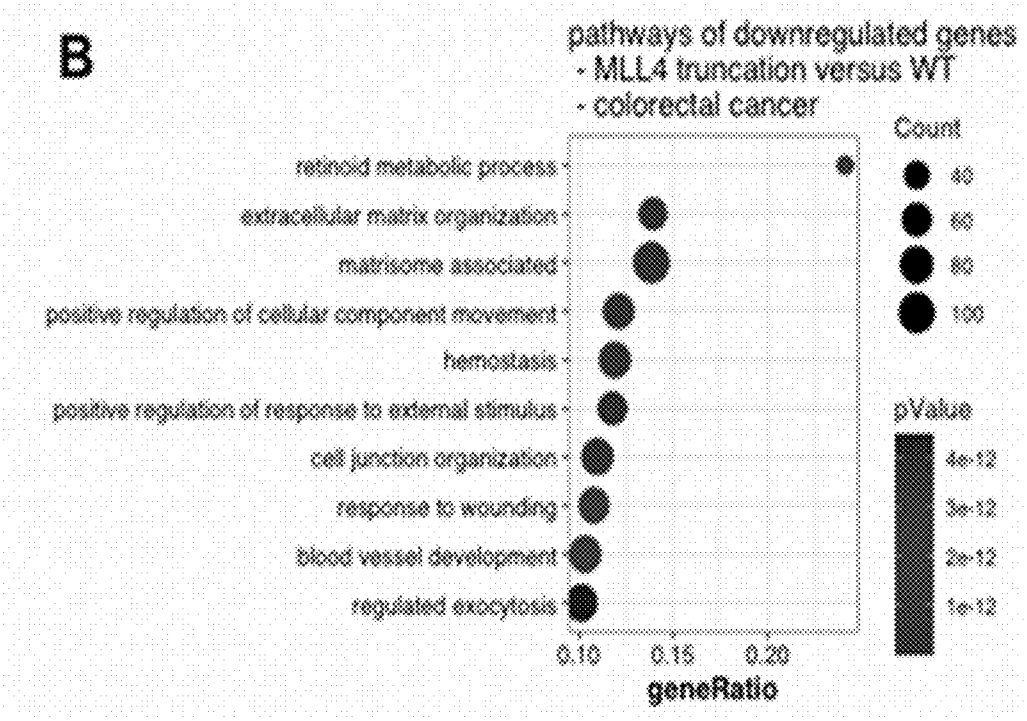
Figure 15:
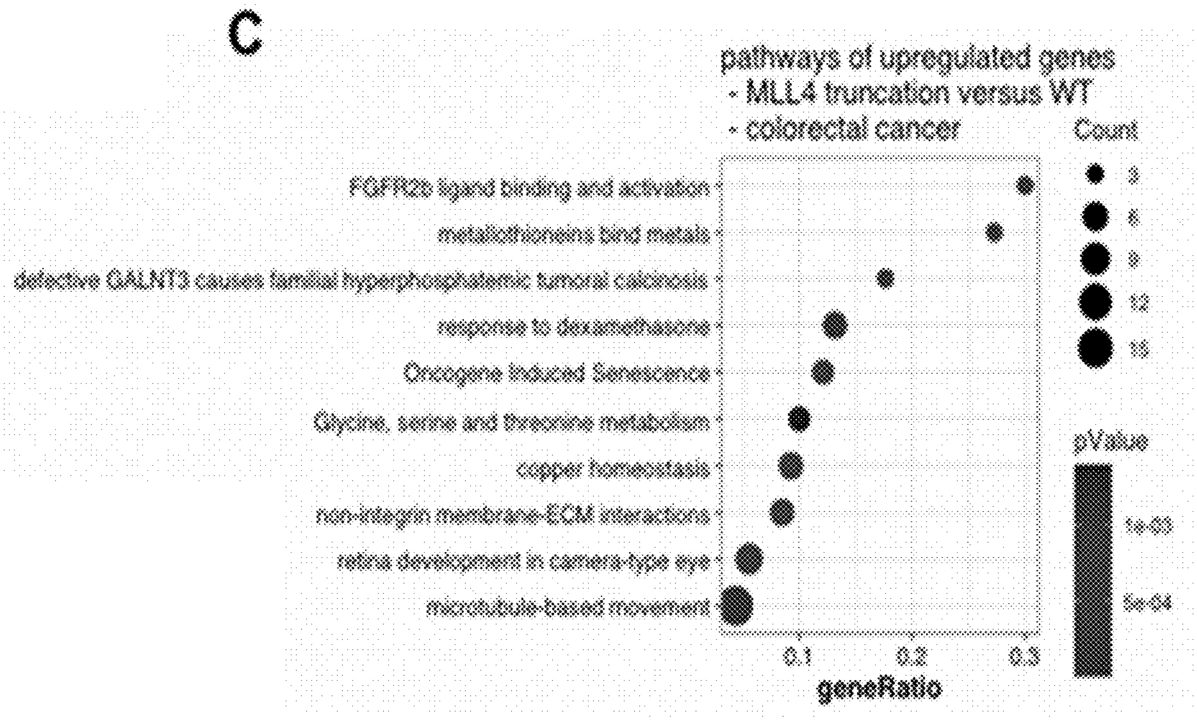
Figure 15:
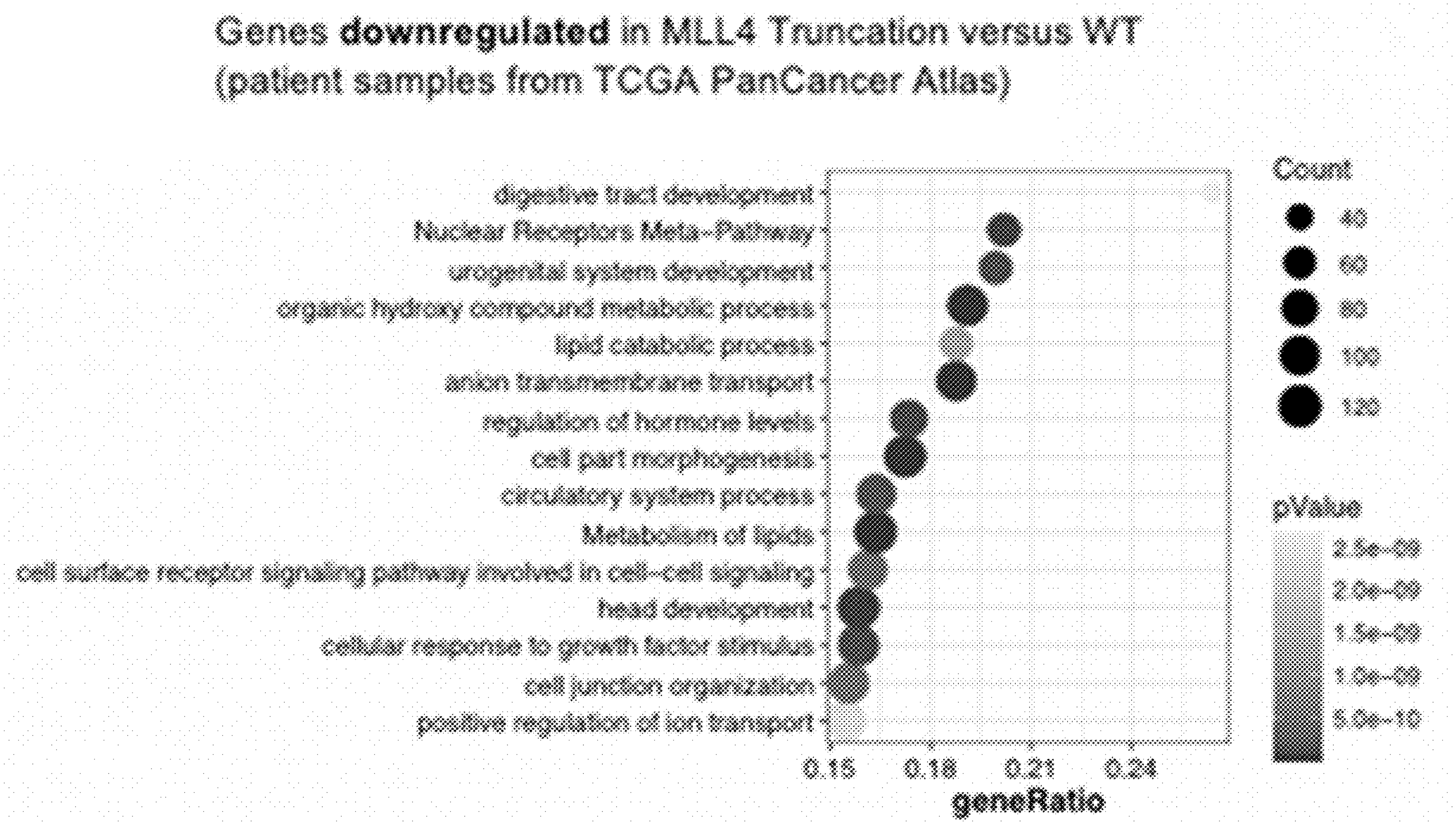
Figure 15:
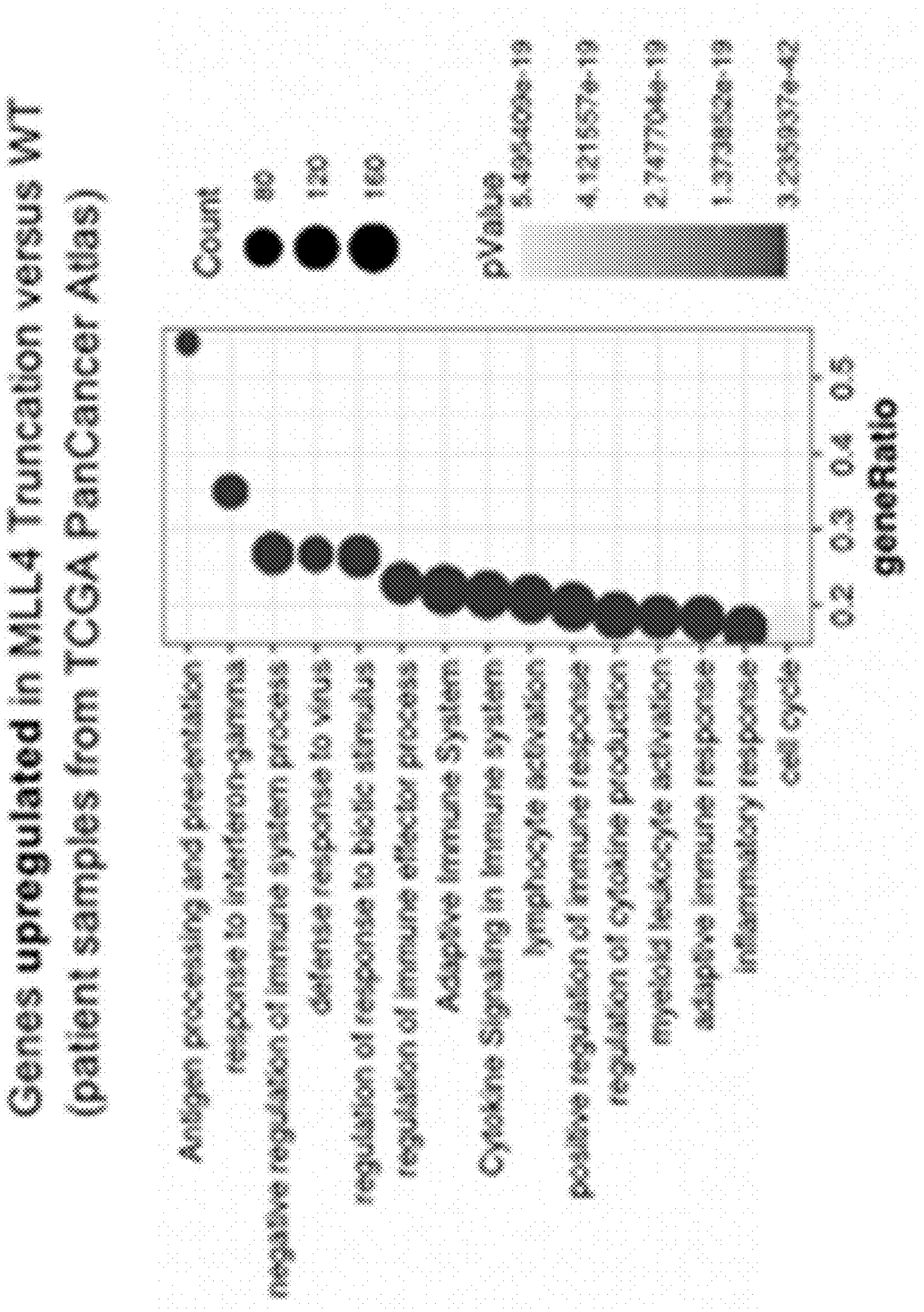
Figure 15:
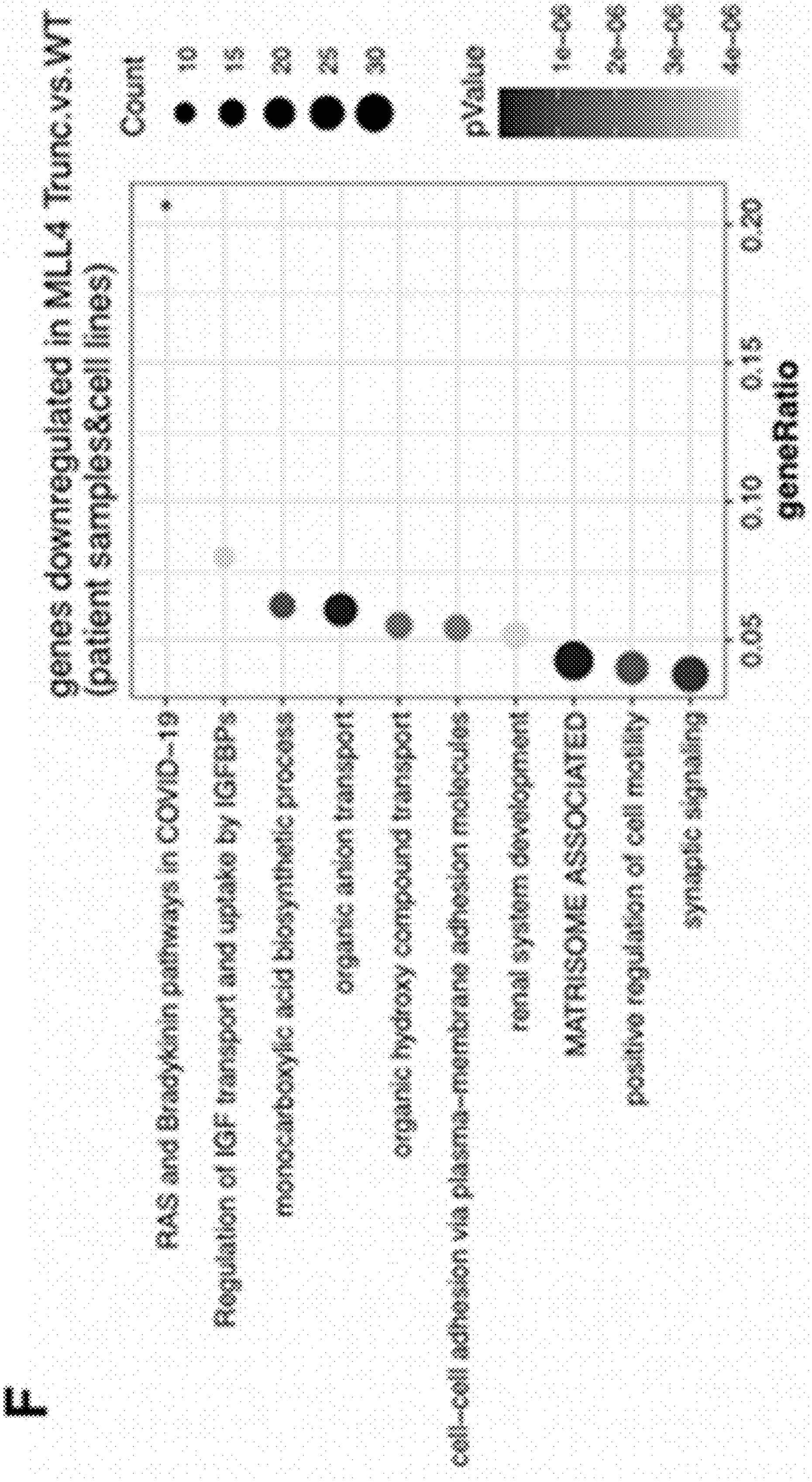

MLL4 Mutant Colorectal Cancer Cells are Selectively Sensitive to Lometrexol Treatment MLL4 is highly mutated in a variety of hematological malignancies and solid tumors. Some of the loss-of-function mutations are believed to function as driver mutations, conferring competitive advantages for clonal expansion (22). Given our studies in mESCs (FIG. 1-4), we sought to examine whether cancer cells bearing MLL4 loss-of-function mutations share similar gene expression profiles. We focused on colorectal cancer since MLL4 has a relatively high rate of mutation in this type of cancer. We first examined CCLE colorectal cancer cell line RNA-seq data. When we analyzed the contribution of all genes to the principal component (PC), truncation mutation of MLL4 tends to segregate the different cell lines along PC2, suggesting genes (anti)correlated with PC2 are those dysregulated as a result of MLL4 truncation mutation (FIG. 15A). The top genes anti-correlated with PC2 (or upregulated genes in MLL4 truncation versus WT) were found in intrinsic apoptotic signaling pathway by p53 class mediator, cell projection morphogenesis, and protein polyubiquitination such as BCL2, PIAS2, E2F2, etc. On the other hand, the top genes correlated with PC2 (or downregulated genes in MLL4 truncation versus WT) were found in matrisome associated, myeloid leukocyte activation, response to wounding, inflammatory response, extracellular matrix organization, and hemostasis such as MMP7, APOE, ACE2, etc (FIG. 15A). Similar GO terms were also found in downregulated genes of Mll3/4 KO versus WT mESCs (eg. cytoskeleton organization, matrisome associated, cell junction organization) (FIG. 15B, C, FIG. 7E, FIG. 12D), suggesting loss-of-function MLL4 mutation in colorectal cancer shares similar gene expression features with mESC depleted of MLL3/4. We further examined the differentially expressed genes in MLL4 Truncation and WT patient samples from TCGA PanCancer Atlas (FIG. 15D, E). Some of the key pathways of the downregulated genes were consistent between colorectal cancer cell lines and patient samples including cell junction organization and matrisome associated (FIG. 15D, F). One of the crucial consequences of MLL4 truncation mutation is the upregulation of immune response activation found in the patient samples (FIG. 15E), which was missing from in vitro cell line study. Our finding is consistent with a previous study showing MLL4 deficiency sensitizes tumors to immune checkpoint blockade (23), and the mutation status of MLL4 (especially truncation mutations) in cancer patients may predict response to immunotherapy and influence patient stratification and decision making.

Figure 16:
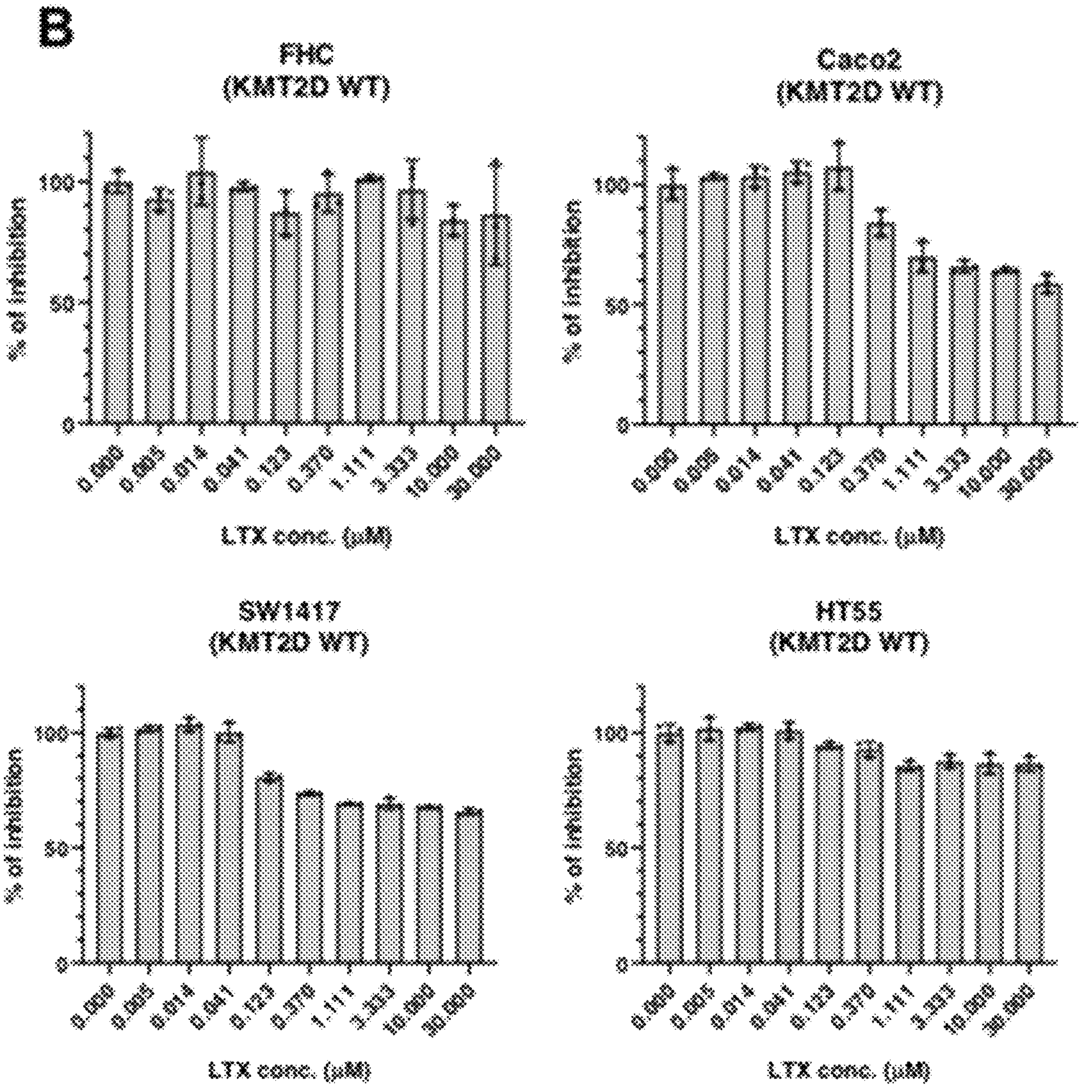
FIG. 16. MLL4 mutant colorectal cancer cells are selectively sensitive to lometrexol treatment. (A) MLL3/4 and UTX mutation status of the colorectal cell lines. (B-C) The bar charts showed MLL4 wild type (B) and MLL4 mutant (C) cells growth inhibition with LTX treatment. (D) The bar charts showed MLL4 wild type and MLL4 mutant cells growth inhibition with Piericidin A treatment (0-10 μM). (E) The bar charts showed MLL4 wild type and MLL4 mutant cells growth inhibition with Phenformin treatment (0-30 mM). CellTiter-Glo® luminescent cell viability assay was performed 72 hours after all the treatments to determine the percentage of inhibition under these conditions.
Figure 16:
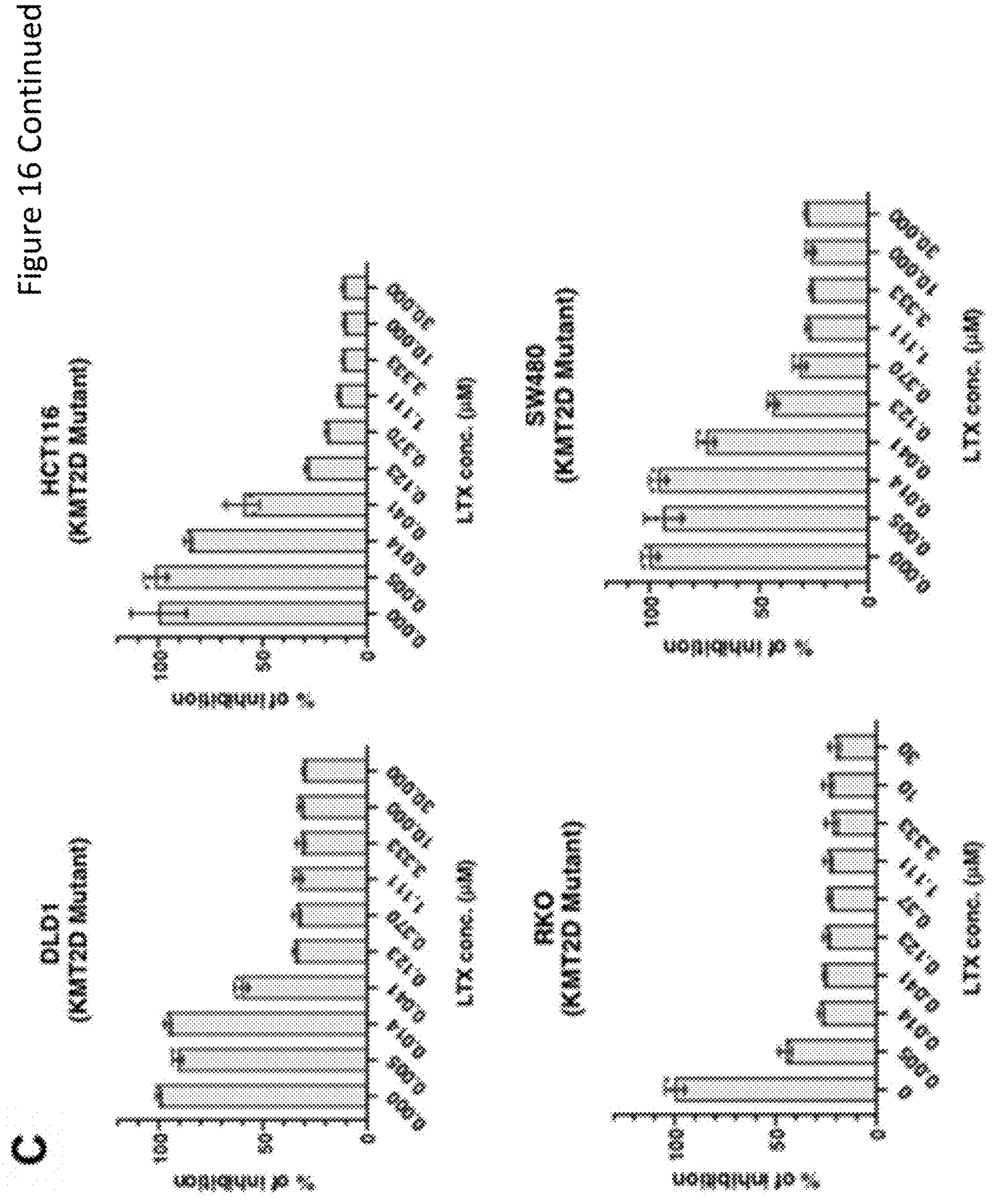
Figure 16:
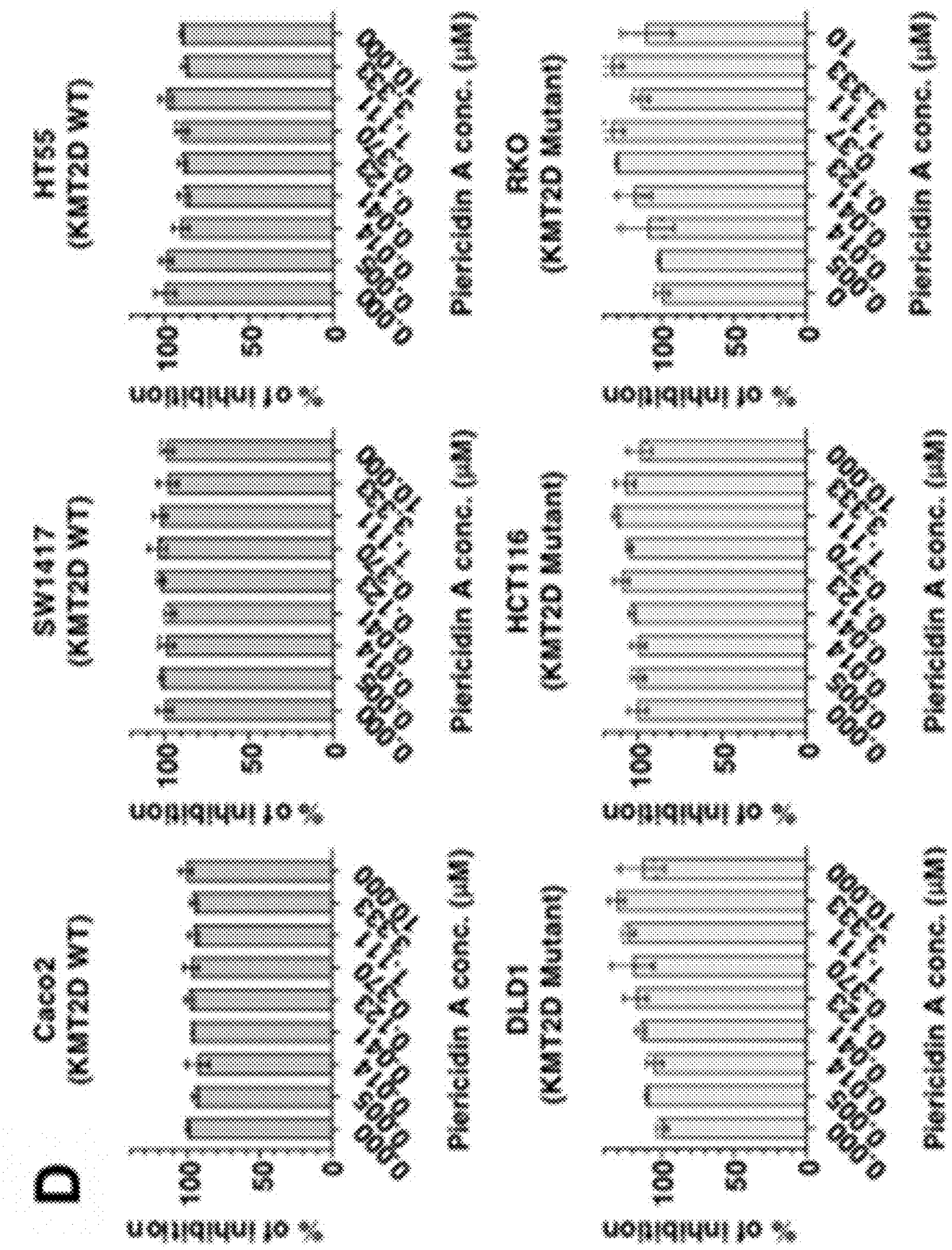
Figure 16:
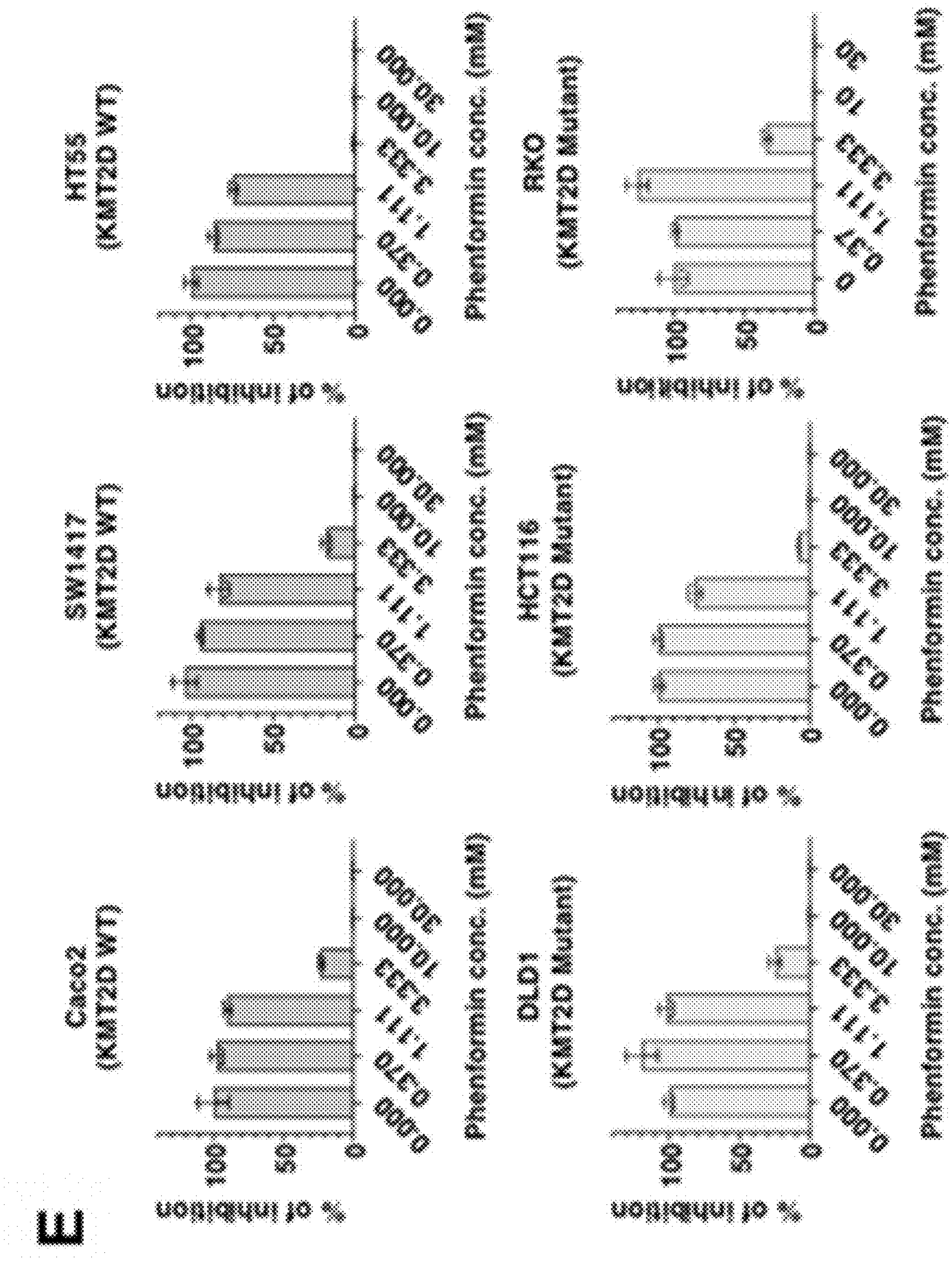

Next, we sought to examine whether colorectal cancer cells bearing MLL4 mutations exhibited elevated sensitivity to lometrexol treatment. Eight colorectal cell lines were selected for comparison including normal epithelial cells (FHC), MLL4 wild type cancer cells (Caco2, SW1417, HT55), and MLL4 mutant cancer cells (SW480, DLD1, HCT116, RKO) (FIG. S16A). It's worth noting that all cancer cell lines have mutations on MLL3 but not UTX (FIG. S16A). Our studies showed that cell lines that harbor MLL4 mutation (especially truncation mutations) were selectively more sensitive to lometrexol treatment than their MLL4 wild type counterpart cells (FIG. 5A and FIG. 16B, C), indicating purine nucleotide synthesis is a general synthetic lethal pathway in MLL3/4 COMPASS deficient cells. Due to the role of MLL4 in mitochondrial metabolism and the fact that upregulation of genes enriched in mitochondrial respiratory chain complex I pathway in MLL3/4 KO mESCs (FIG. 12E), we further treated colorectal cancer cells with Piericidin A or Phenformin—the mitochondrial complex I inhibitors. We observed no sensitivity difference between MLL4 WT and mutant cells (FIG. 16D, E).

Figure 17:
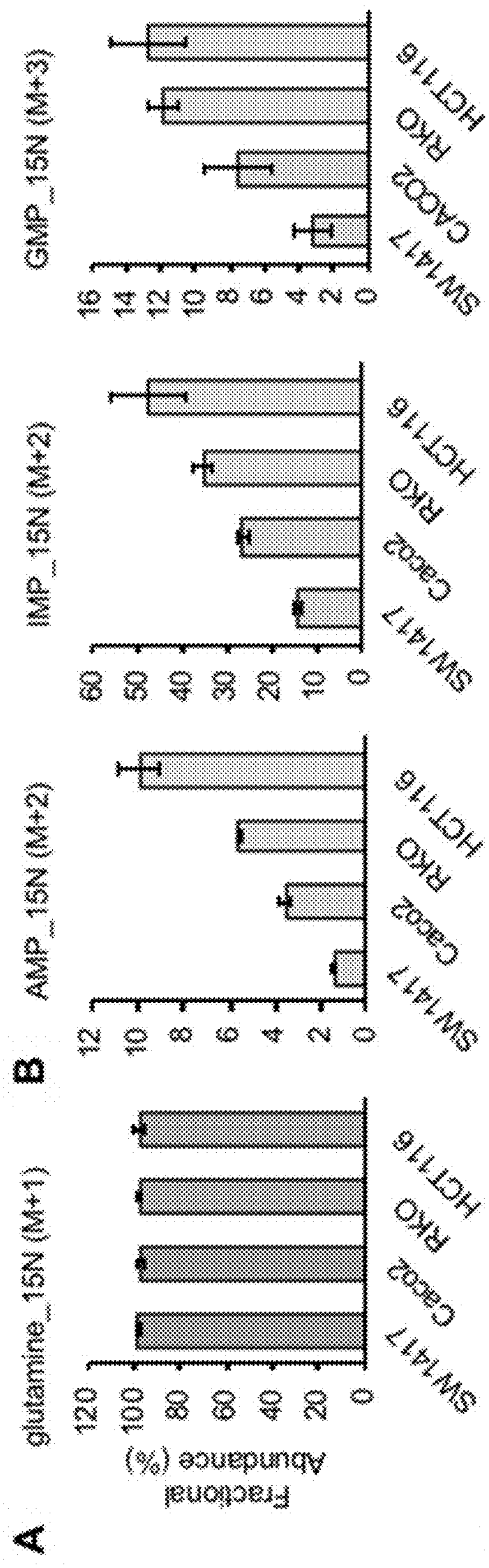
FIG. 17. Cells lacking of MLL4 function are selectively sensitive to de novo purine synthesis inhibition. (A) Tracer levels of glutamine (M+1) in SW1417, Caco2, RKO and HCT116 cells. (B) Labeled purine metabolite levels with $^{15}N$ glutamine tracing in SW1417, Caco2, RKO and HCT116 cells. MLL4 WT cells, blue; MLL4 mutant cells, red. (C) CellTiter-Glo® luminescent cell viability assay in CAL51 MLL4 WT, heterozygous truncation mutation (hNTD), and KO cells treated with MTX (0-1 μM). (D) CAL51 WT and MLL4KO cells were treated with 0.04, or 0.4 μM MTX in the presence of H2O, 50 μM thymidine or 50 μM inosine. CellTiter-Glo® luminescent cell viability assay was performed. (E-J) Cells were infected with lentiviruses expressing shCtrl, shGART or shPAICS. Two distinct shRNAs were included for GART and PAICS. Western blot showing the knockdown of GART and PAICS in RKO, HCT116, Caco2 and HT55 cells (E). Uncropped western blot images were shown in FIG. S15. The growth rates of HCT116 (F), RKO (G), Caco2 (H) and HT55 (I) cells with shCtrl, shGART or shPAICS were measured by cell counting, and the cell number was normalized with day 0. Colony formation of the four cell lines with GART or PAICS knockdown was performed by seeding 500 or 1000 cells in the 6 well plates and stained after 10-14 days of culture with media change every three days (J).
Figure 17:
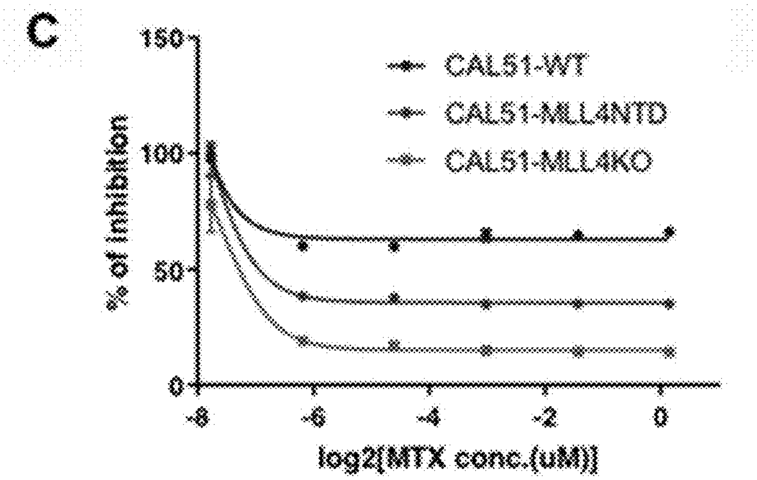
Figure 17:
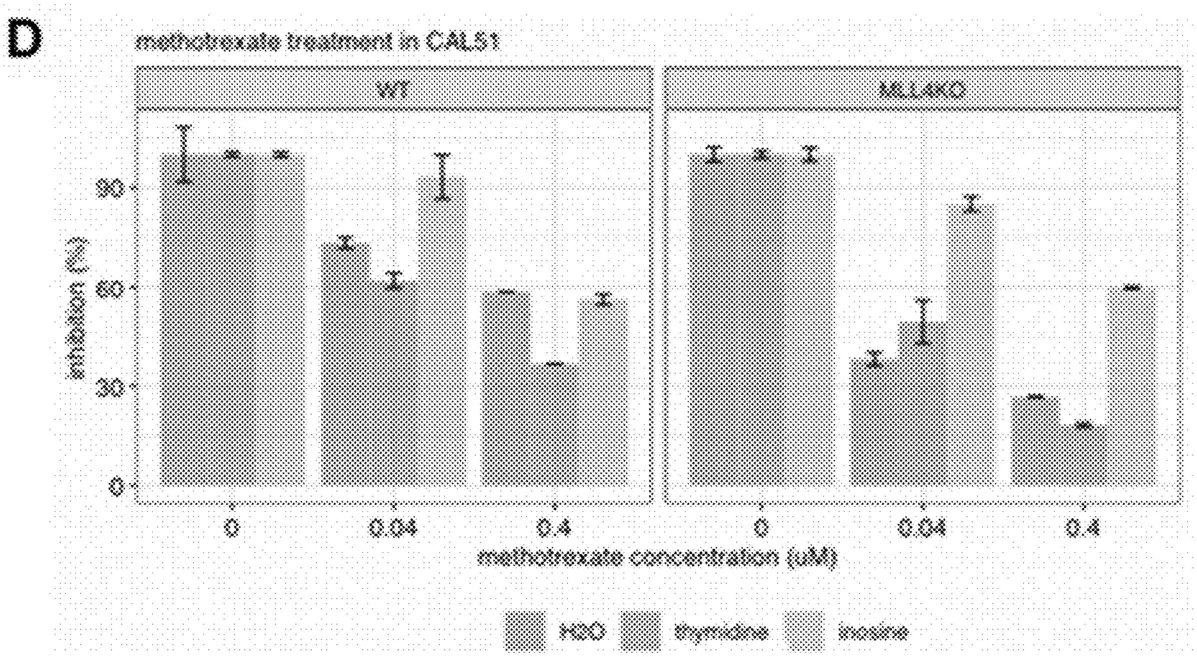
Figure 17:
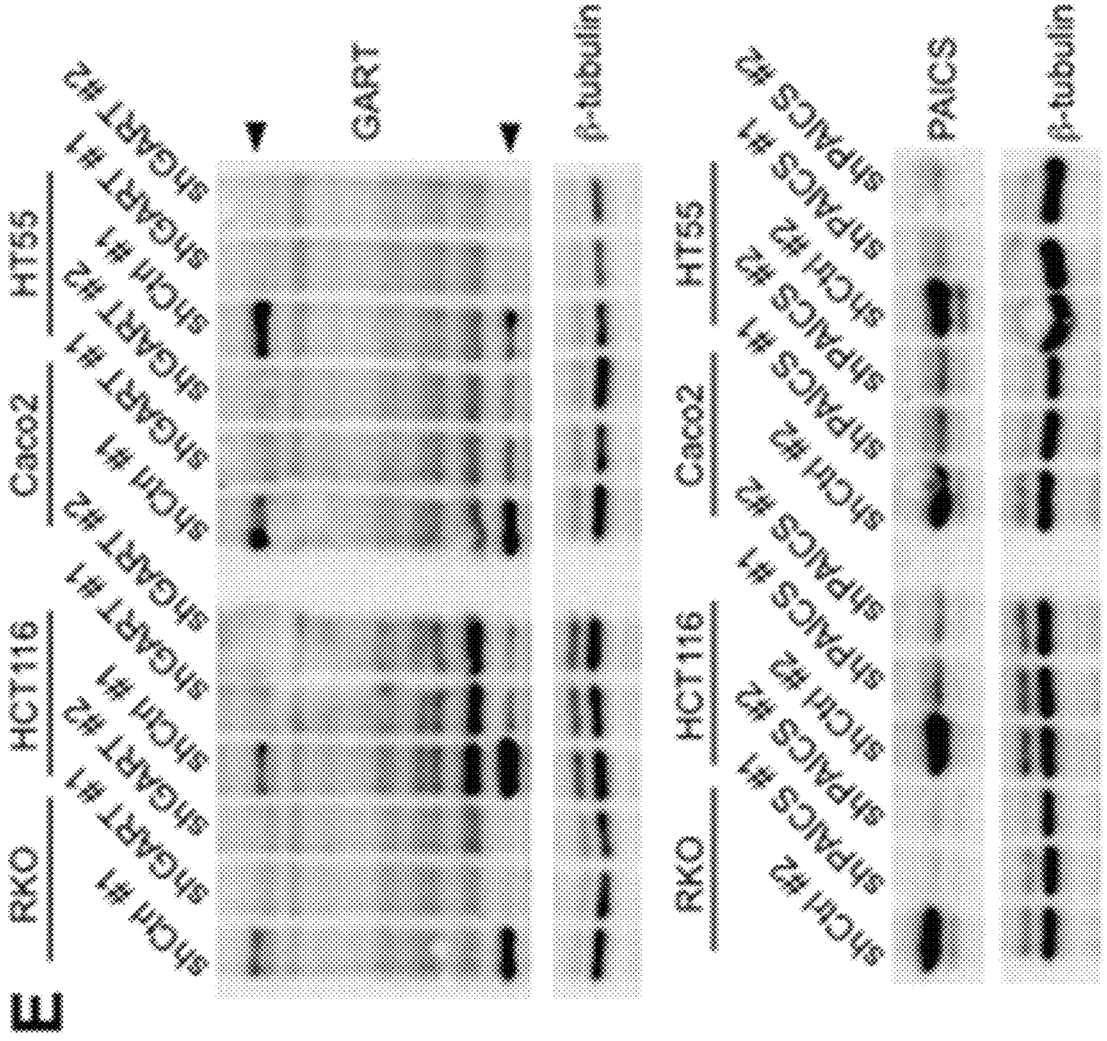
Figure 17:
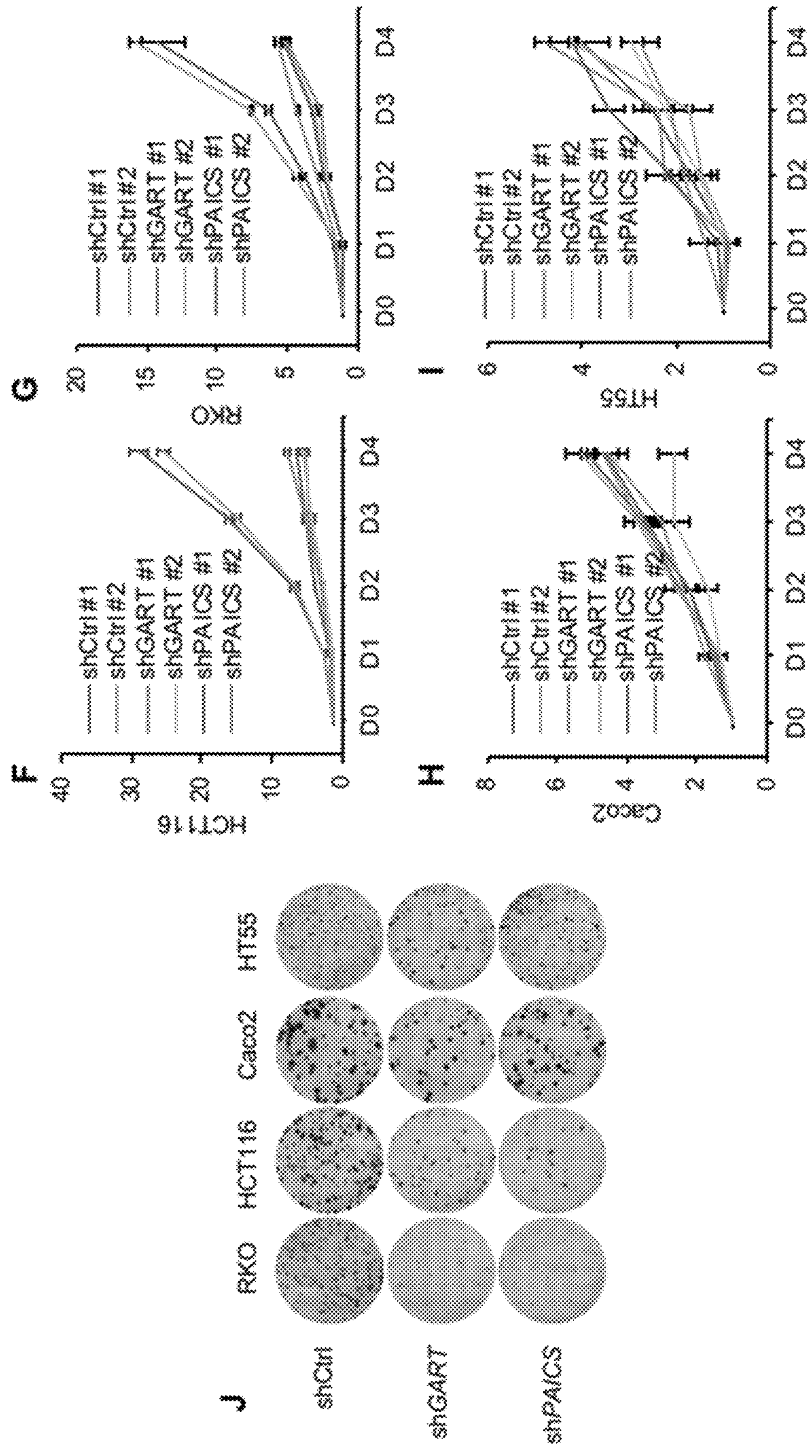

We further employed $^{15}$N-glutamine tracing in MLL4 WT (SW1417 and Caco2) and MLL4 truncation mutation (RKO and HCT116) colorectal cancer cells, and demonstrated that mutant cells exhibited increased flux through de novo purine synthesis (FIG. 17A, B). Next, we generated MLL4 truncation mutated (MLL4hNTD) or MLL4 complete knockout (MLL4KO) CAL51 breast cancer cells and measured sensitivity to methotrexate (MTX). CAL51 cells with compromised MLL4 functions gain elevated MTX sensitivity (FIG. 17C). The cytotoxic effect of MTX on MLL4KO cells was rescued by inosine not thymidine, further confirming the inhibitory effect via purine synthesis but not dTMP synthesis (FIG. 17D). We also knocked down GART and PAICS, two key enzymes for de novo purine synthesis in these colorectal cancer cells (FIG. 17E). Both cellular growth and colony formation were significantly decreased in MLL4 mutant cells (RKO and HCT116) but not MLL4 WT cells (Caco2 and HT55) (FIG. 17F-J). Our data demonstrated that cancer cells with reduced MLL4 functions have an elevated flux through purine synthesis and are more sensitive to inhibitors targeting de novo purine synthesis specifically.

Figure 5:
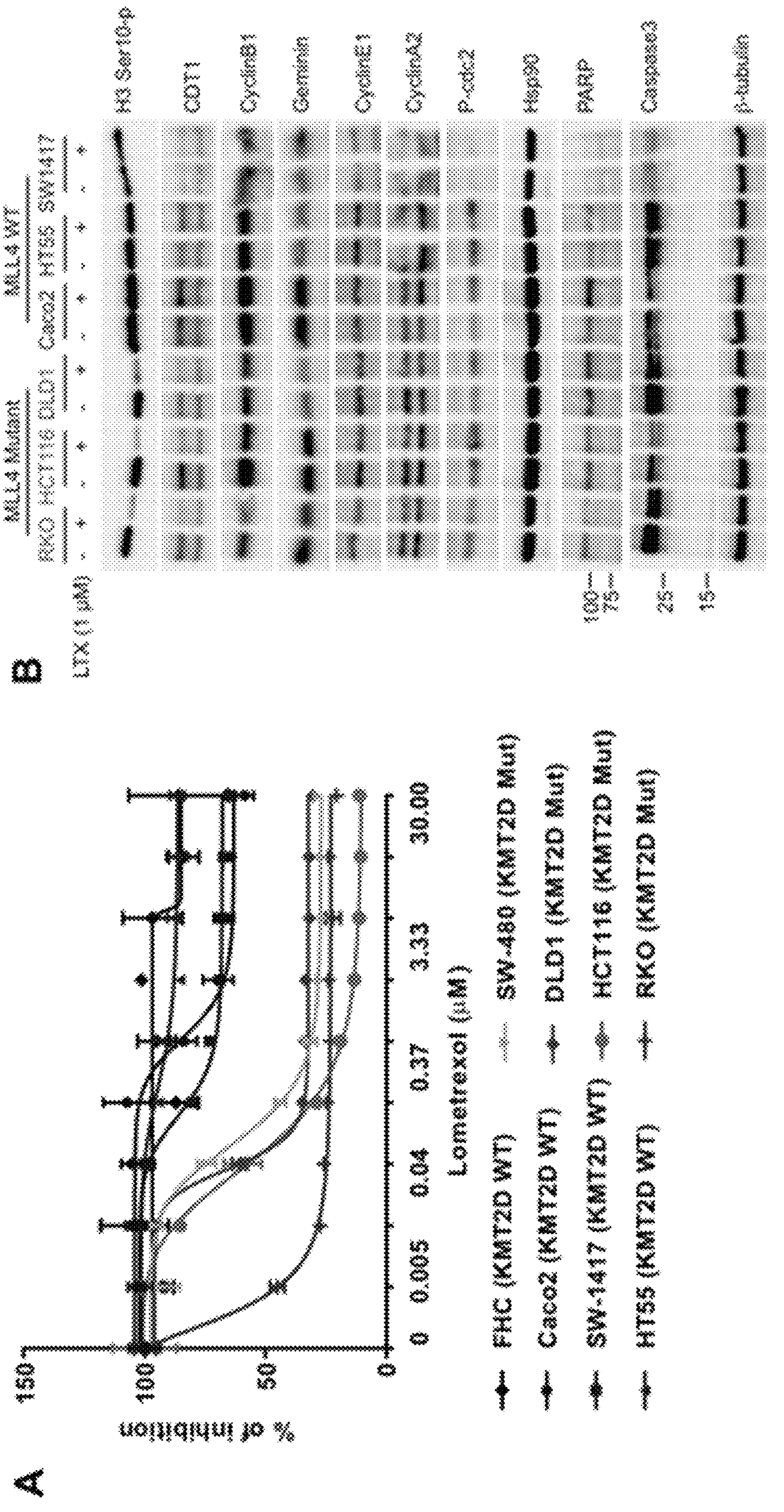
FIG. 5. MLL4 mutant colorectal cancer cells are selectively sensitive to lometrexol treatment. (A) 100 μL of $0.5\times10^5$ cells/mL cells were seeded in 96-well plates one day before treatment. Cells were treated with 0-30 μM lometrexol (LTX) with 3× fold dilution for 72 hours. CellTiter-Glo® luminescent cell viability assay was performed to determine the percentage of inhibition under these conditions. The line plot compares sensitivity difference of all cell lines tested. (B) RKO, HCT116, DLD1, Caco2, HT55 and SW1417 cells were treated with DMSO or 1 μM LTX for 24 hours and whole cell lysates were used for western blot against cell cycle (H3 Ser10-p, CDT1, CyclinB 1, Geminin, CyclinEl, CyclinA2, p-cdc2) and apoptosis (PARP, Caspase3) markers using Hsp90 and β-tubulin as loading control. Uncropped western blot images were shown in FIG. S15. (C) Venn diagram showing the overlap of downregulated genes in LTX treated versus control in RKO, HCT116, and DLD1. (D) Hierarchical clustering heatmap showing the commonly downregulated gene expression in LTX treated versus control in RKO, HCT116, and DLD1 (n=885). (E) Box plot showing the log FC of the 885 commonly downregulated genes in RKO, HCT116, and DLD1 with LTX treatment. (F) A subset of representative terms from the full cluster were selected and converted into a network layout. Each term is represented by a circle node, where its size is proportional to the number of input genes fall under that term, and its color represent its cluster identity. Terms with a similarity score>0.3 are linked by an edge (the thickness of the edge represents the similarity score). The network is visualized with Cytoscape with "force-directed" layout and with edge bundled for clarity. One term from each cluster is selected to have its term description shown as label.
Figure 5:
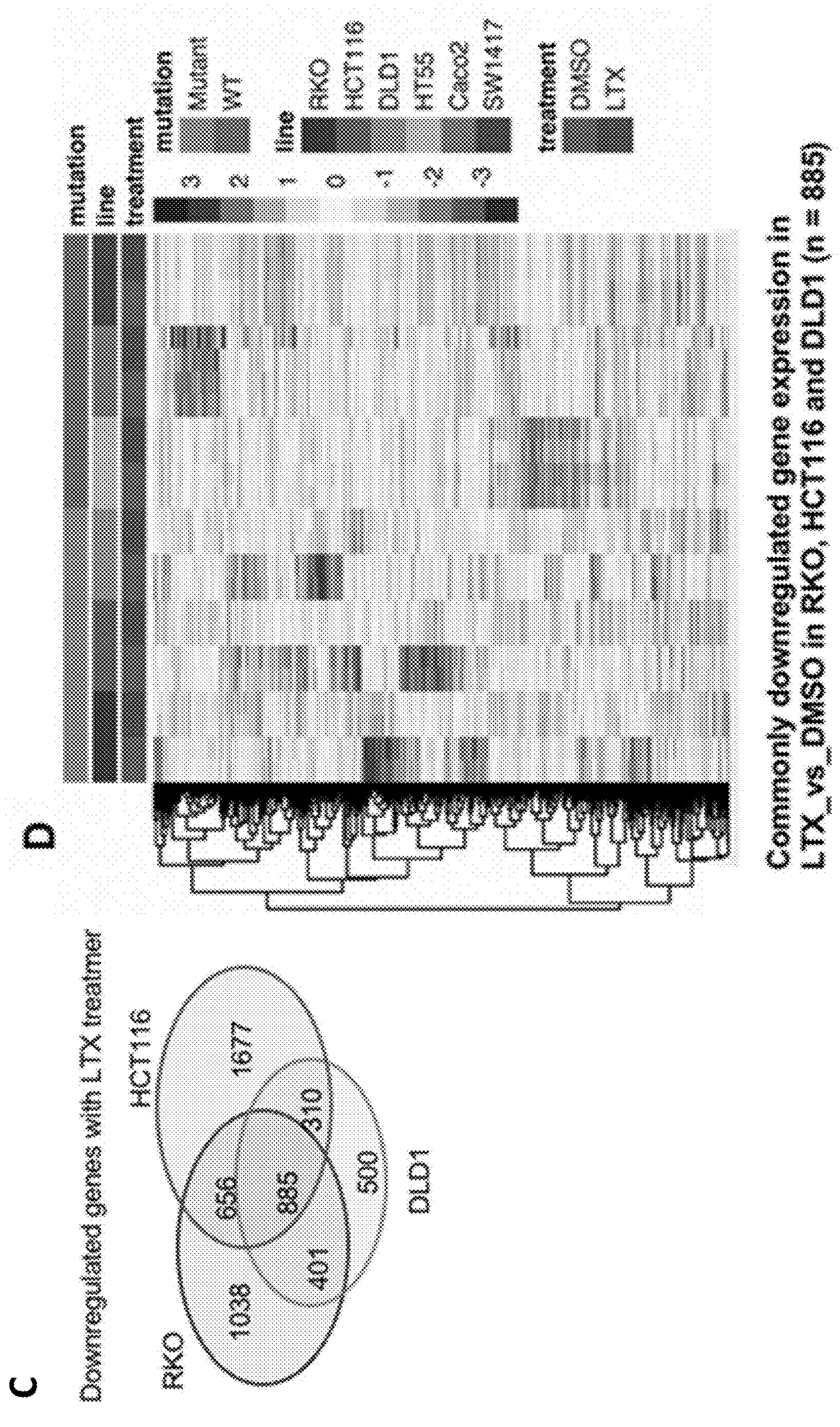
Figure 5:
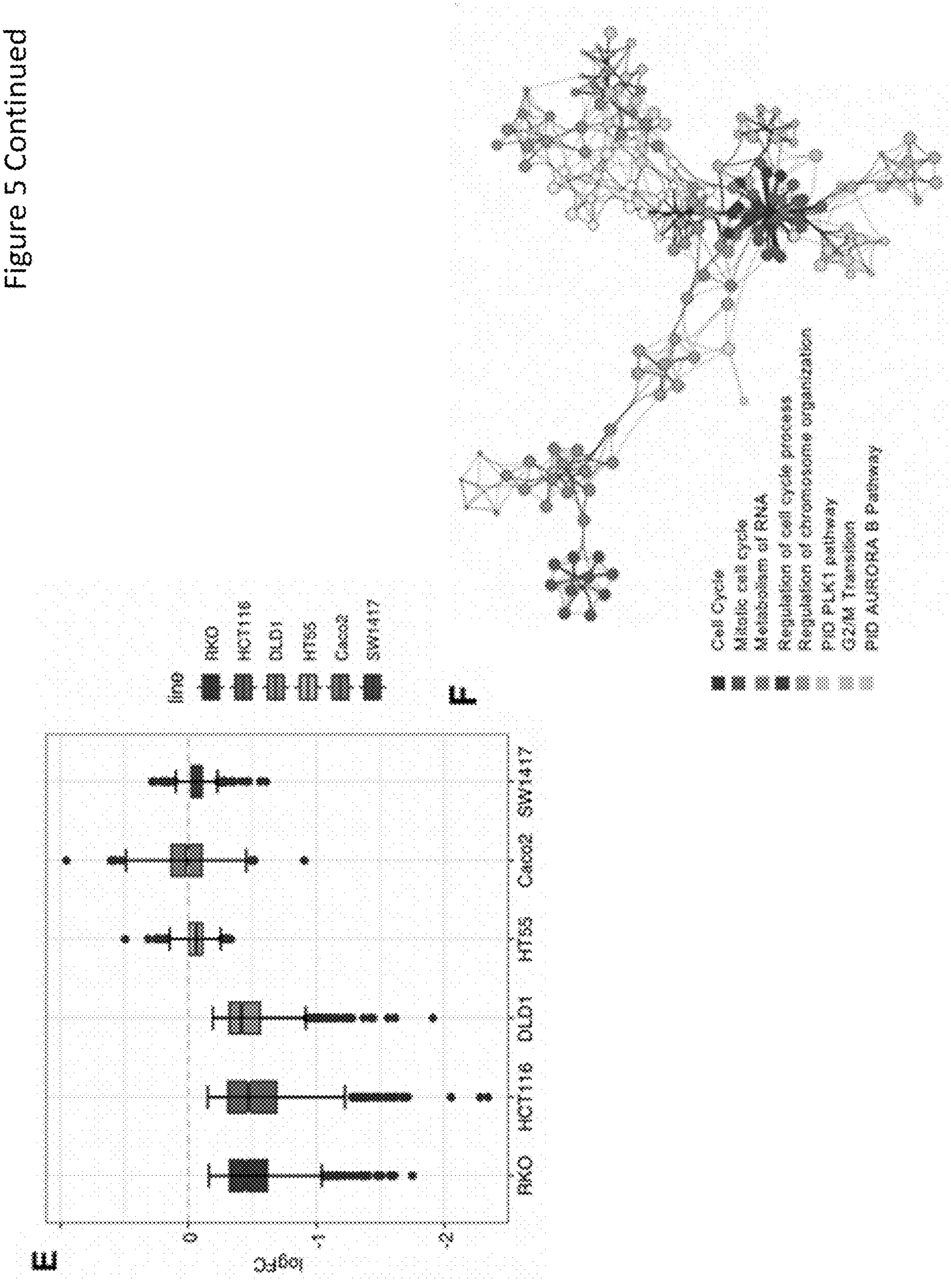
Figure 18:
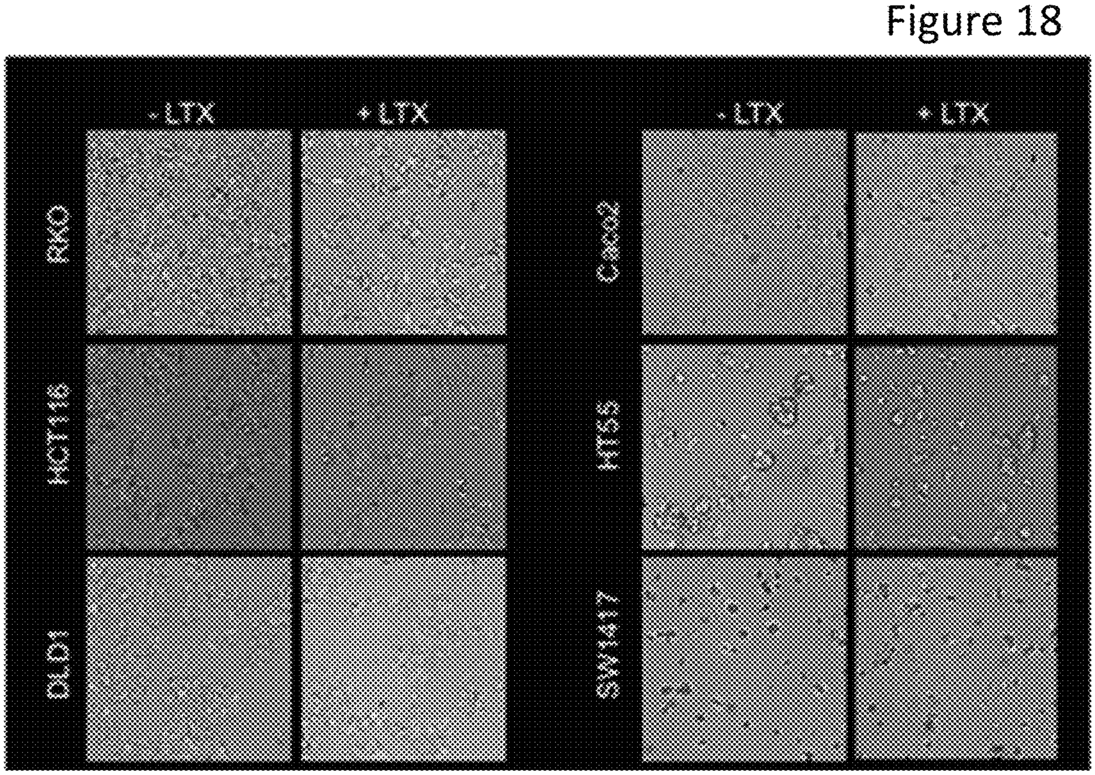
FIG. 18. RNA-seq data in colorectal cancer cells treated with LTX. (A) Cellular morphological change in different cells treated with LTX at 1 μM for 24 hours under bring field microscope. (B) summary of differentially expressed gene number in different cell lines. adj.p<0.01. (C) Venn diagram showing the overlap of upregulated genes in LTX treated versus control in RKO, HCT116, and DLD1. (D) Hierarchical clustering heatmap showing the commonly upregulated gene expression in LTX treated versus control in RKO, HCT116, and DLD1 (n=707). (E) Box plot showing the log FC of the 707 commonly upregulated genes in RKO, HCT116, and DLD1 with LTX treatment.
Figure 18:
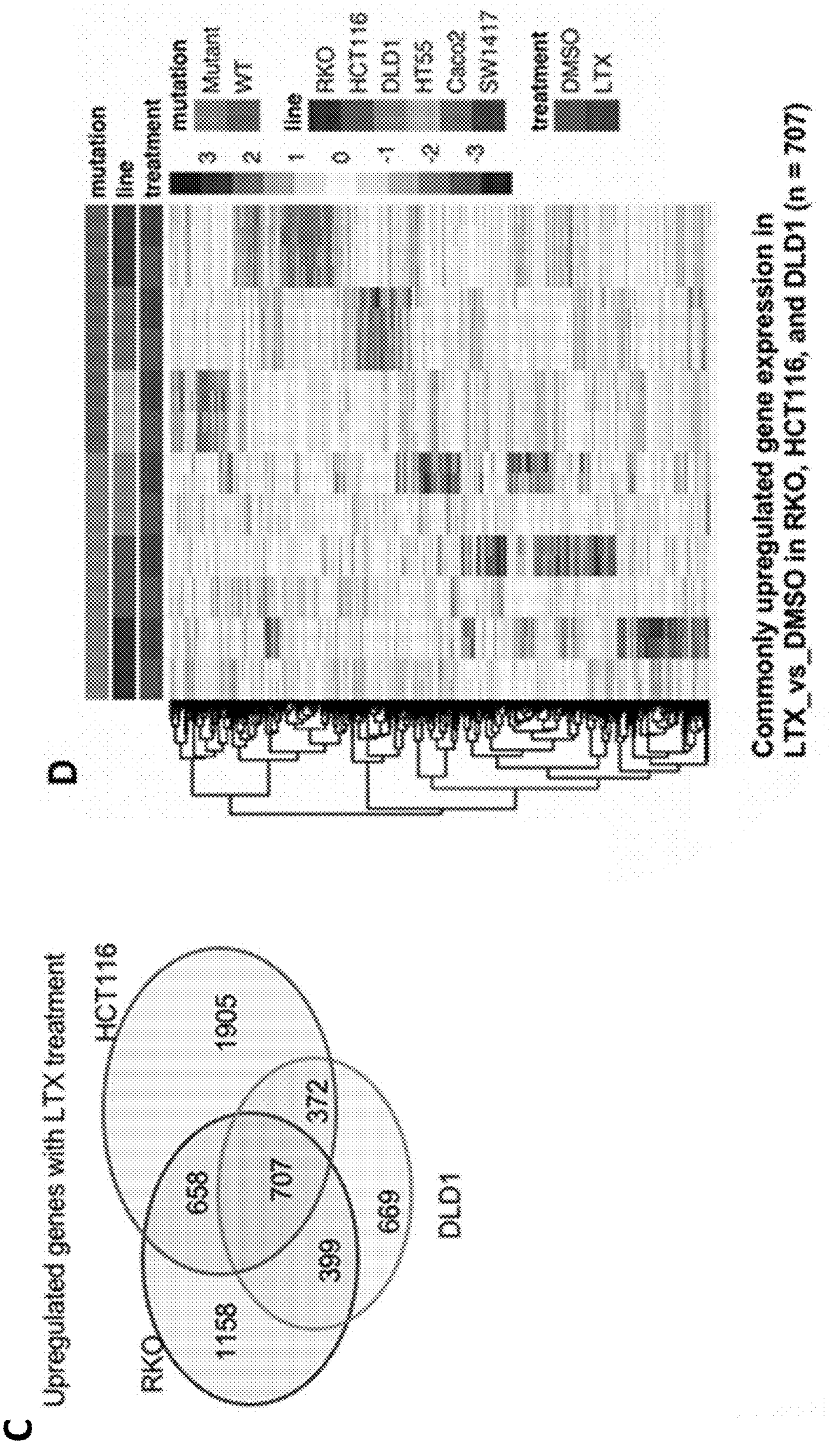
Figure 18:
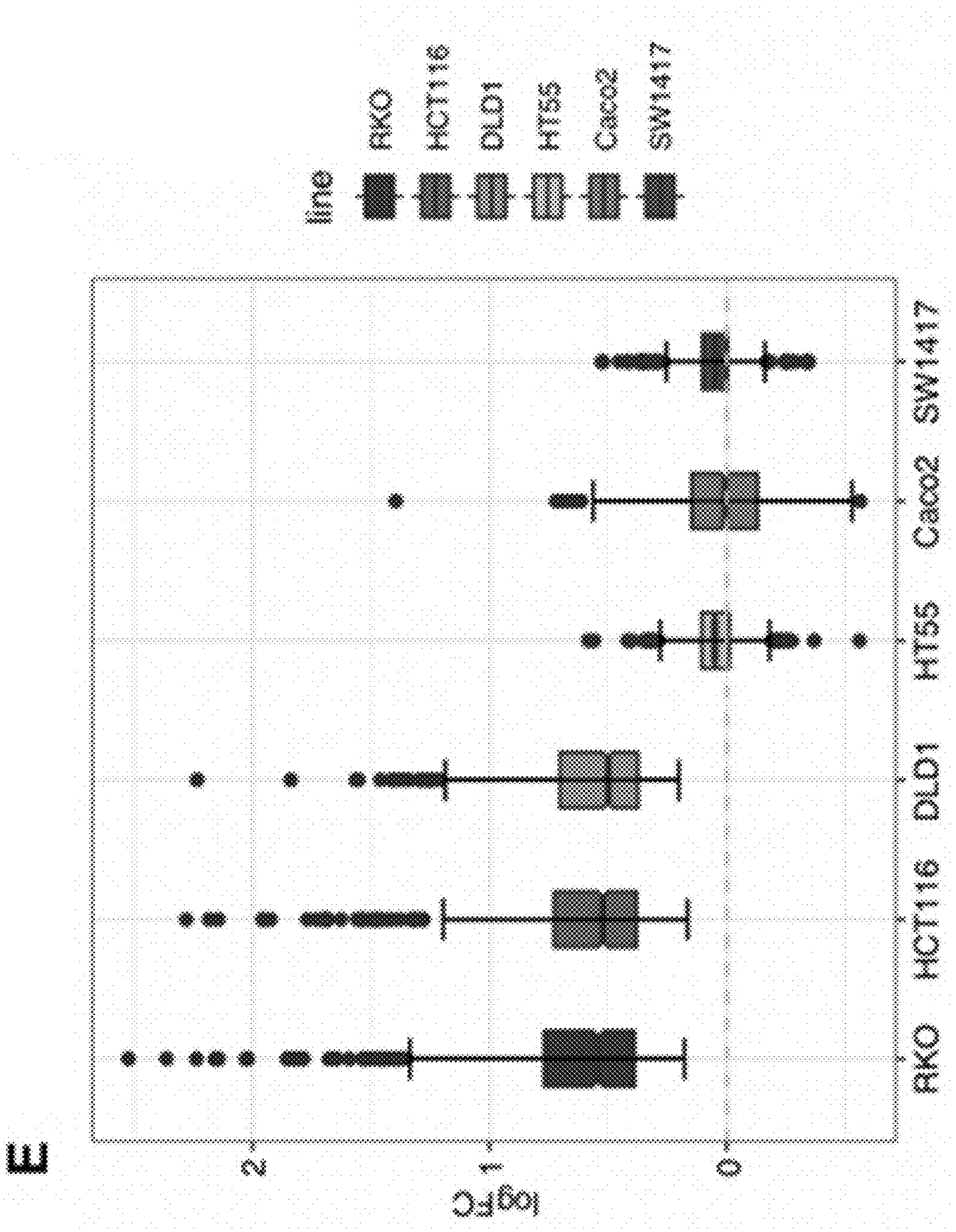
Figure 19:
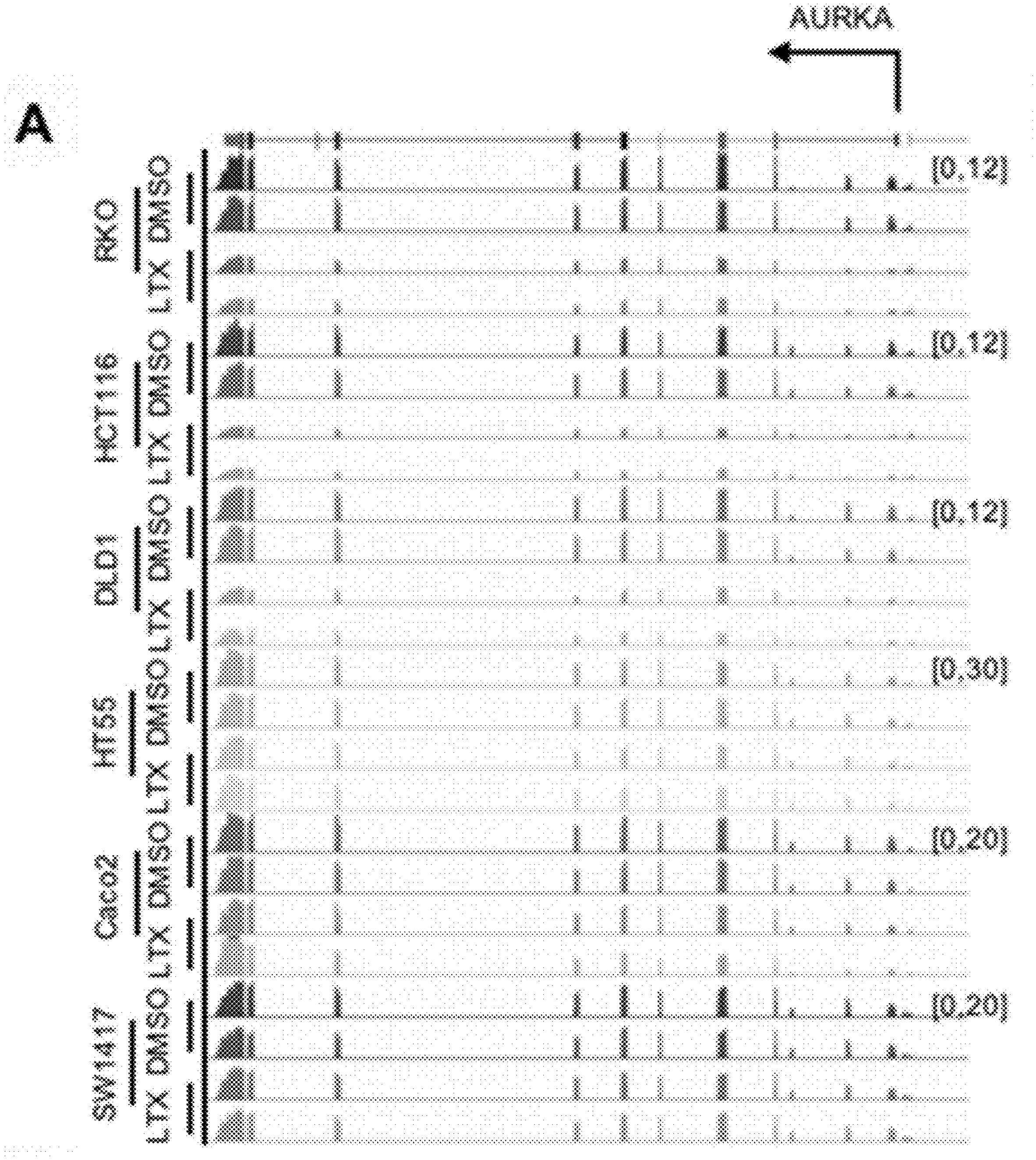
FIG. 19. The unique gene expression signature of MLL4 mutant cells in response to LTX treatment. (A-B) RNA-seq track examples showing the AURKA (A) and PLK1 (B) gene expression in different cell lines in response to LTX treatment. (C) A collection of 217 genes related to mitotic cell cycle pathways found in LTX commonly downregulated genes was selected. Volcano plots showing the top 20 downregulated genes involved in mitotic cell cycle pathways in each cell line including RKO, HCT116, and DLD1. The 10 common genes found in the plots were defined as "lometrexol responsive mitotic gene signature" including PLK1, AURKA, CDCA3, CDC20, SFPQ, POLA1, PSRC1, KIF20A, FAM83D, and DLGAP5. (D) Volcano plots showing the 10 genes in MLL4 WT cell lines including HT55, Caco2, and SW1417.
Figure 19:
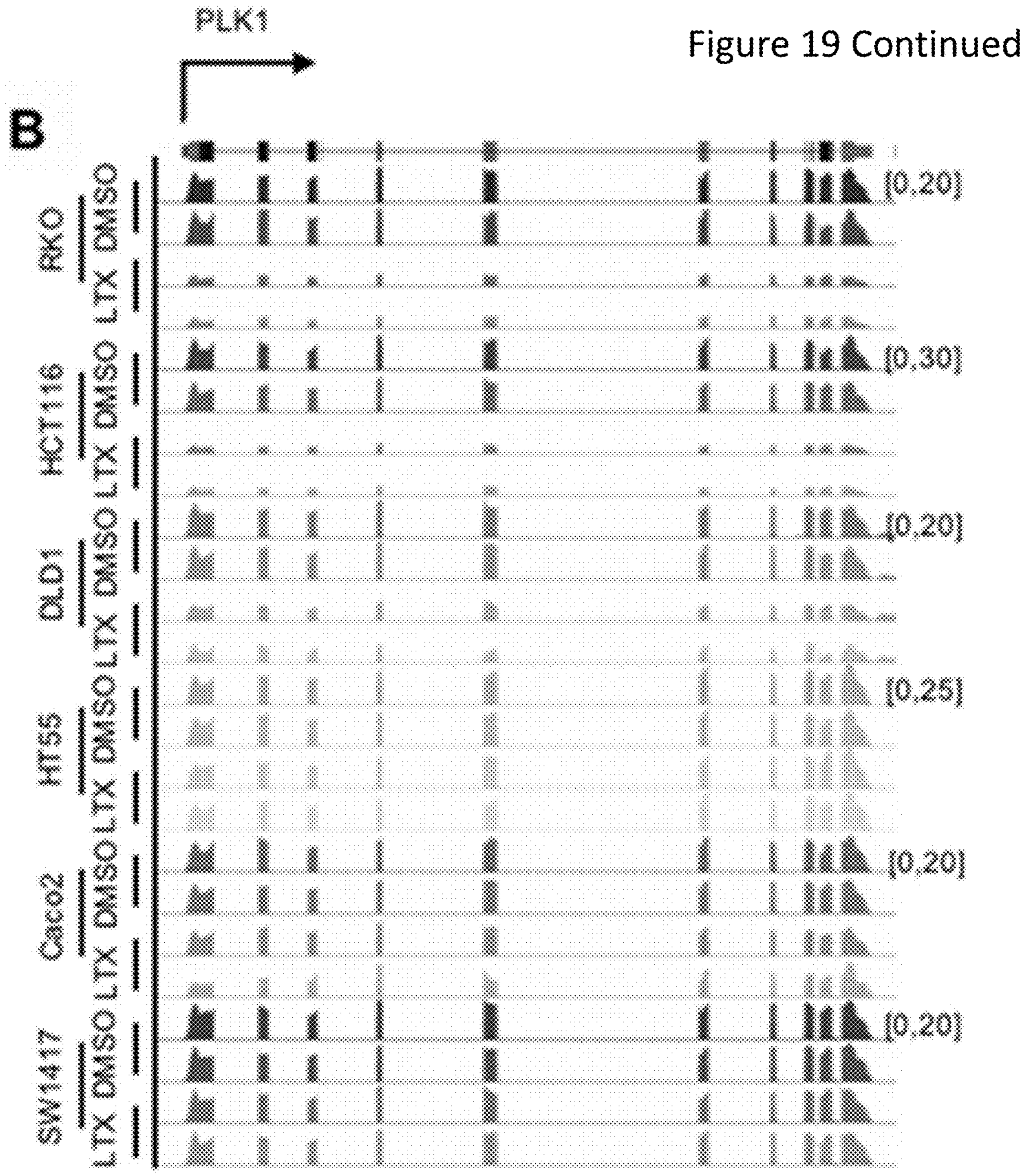
Figure 19:
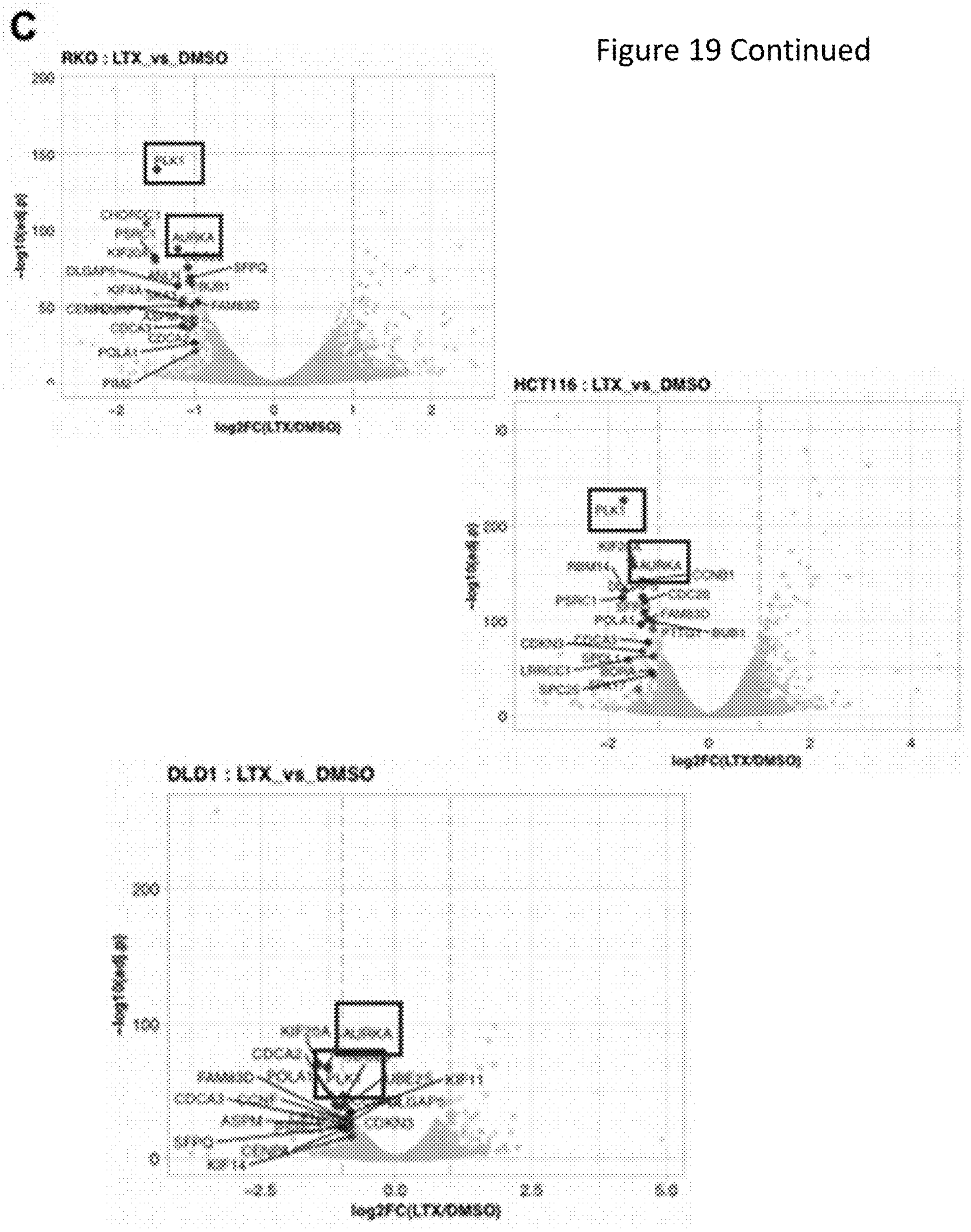
Figure 19:
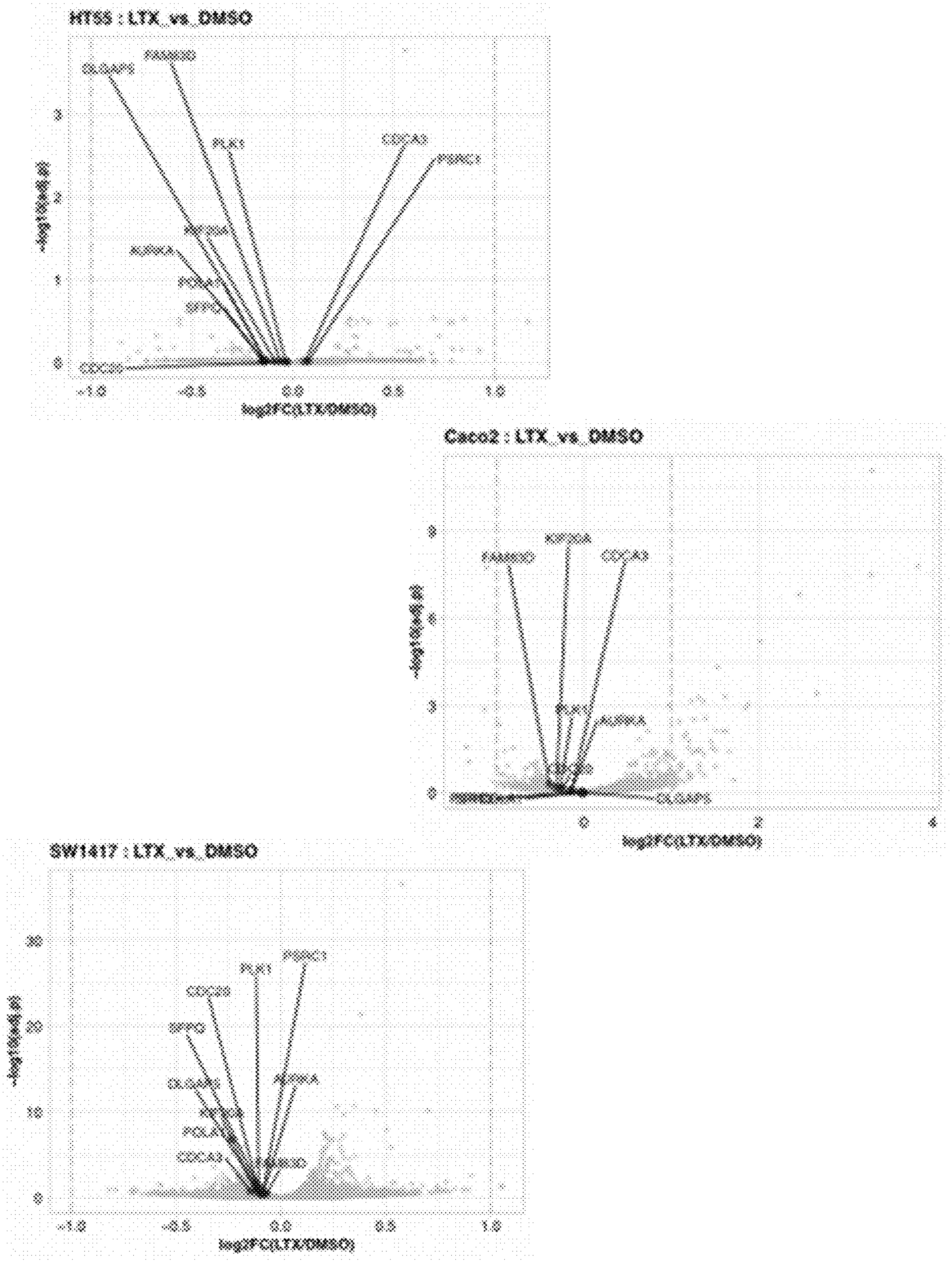

Lometrexol Elicited Downregulated Mitotic Cell Cycle Genes Expression in MLL4 Mutant Cancer Cells To investigate the potential mechanisms of LTX induced cytotoxic effects in MLL4 WT and mutant cells, we examined a panel of cell cycle and apoptosis markers (FIG. 5B, FIG. 18A). A significant downregulation of histone H3 Serine10 phosphorylation (H3 Ser10-p), CDT1 and CyclinB1 was observed only in MLL4 mutant cells but not WT cells, indicating LTX induced cell cycle arrest and mitotic defects (FIG. 5B). We further examined the gene expression change 24 hours after LTX treatment in order to define a unique gene expression signature associated with LTX. Consistent with the morphological change and cell cycle defect, LTX only induced significant differential gene expression change in MLL4 mutant cells (FIG. 18B). In total, there are 885 genes commonly downregulated by LTX treatment in all MLL4 mutant cells (FIG. 5C-E), and these genes were unaffected in MLL4 WT cells (FIG. 5D, E). Vice versa, 707 genes commonly upregulated by LTX treatment in MLL4 mutant cells were unaffected in MLL4 WT cells (FIG. 18C-E). LTX downregulated genes were involved in mitotic cell cycle, regulation of chromosome organization, PLK and AURORA kinase pathways, and G2/M transition (FIG. 5F). For example, PLK1 and AURKA gene expression were remarkably diminished in all MLL4 mutant cells in response to LTX while the gene expression remained the same in MLL4 WT cells (FIG. 19A, B). Out of the 885 commonly downregulated genes, we focused on a collection of 217 genes related to mitotic cell cycle pathways and examined their gene expression in MLL4 mutant cells. The top 20 downregulated genes involved in mitotic cell cycle pathways in each cell line were shown in the volcano plots (FIG. 19C). We next defined a "lometrexol responsive mitotic gene signature" including PLK1, AURKA, CDCA3, CDC20, SFPQ, POLA1, PSRC1, KIF20A, FAM83D, and DLGAP5, all of which were the top downregulated genes in each MLL4 mutant cell line, with no effect in MLL4 WT cells (FIG. 19D).

Figure 6:
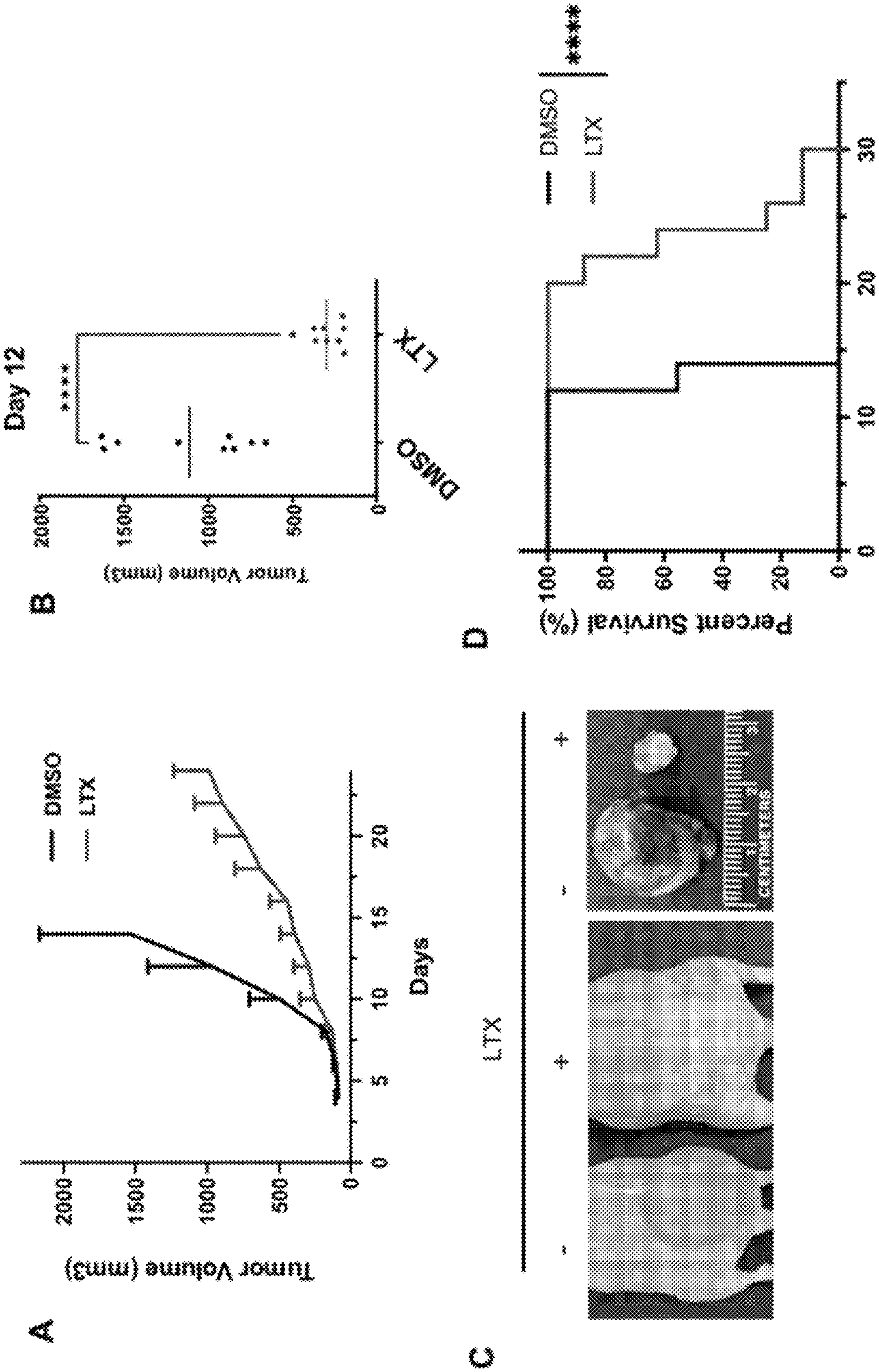
FIG. 6. Inhibition of de novo purine synthesis by lometrexol inhibits MLL4 mutant tumor growth. Tumor development after inoculation of 4×10 6 of HCT116 cells into the nude mice. Mice with HCT116 subcutaneous (sc) tumor were either treated with vehicle (DMSO, n=9) or LTX (25 mg/kg, n=9) daily for 7 days. (A) Growth plots for sc tumors in each treatment group were shown. Tumor volumes (mm3) show mean and upper SD. (B) Dot plot representation of sc tumor volume in mice at day 12 post-tumor cell injection. Unpaired t-test values for comparisons between DMSO and LTX treatment: **, P<0.0001. (C) Photographs of nude mice (left) and sc tumor taken from these mice (right) in which HCT116 cells were inoculated into the right flank. (D) Animal survival at the indicated days after inoculation. Log-rank test was used for comparisons between DMSO and LTX treatment: **, P<0.0001. (E) H&E staining and immunohistochemistry showing the proliferation and apoptosis in tumors with Ki-67 and TUNEL staining. The signals for Ki-67 and TUNEL are quantified and shown in the bar plots on the right.
Figure 6:
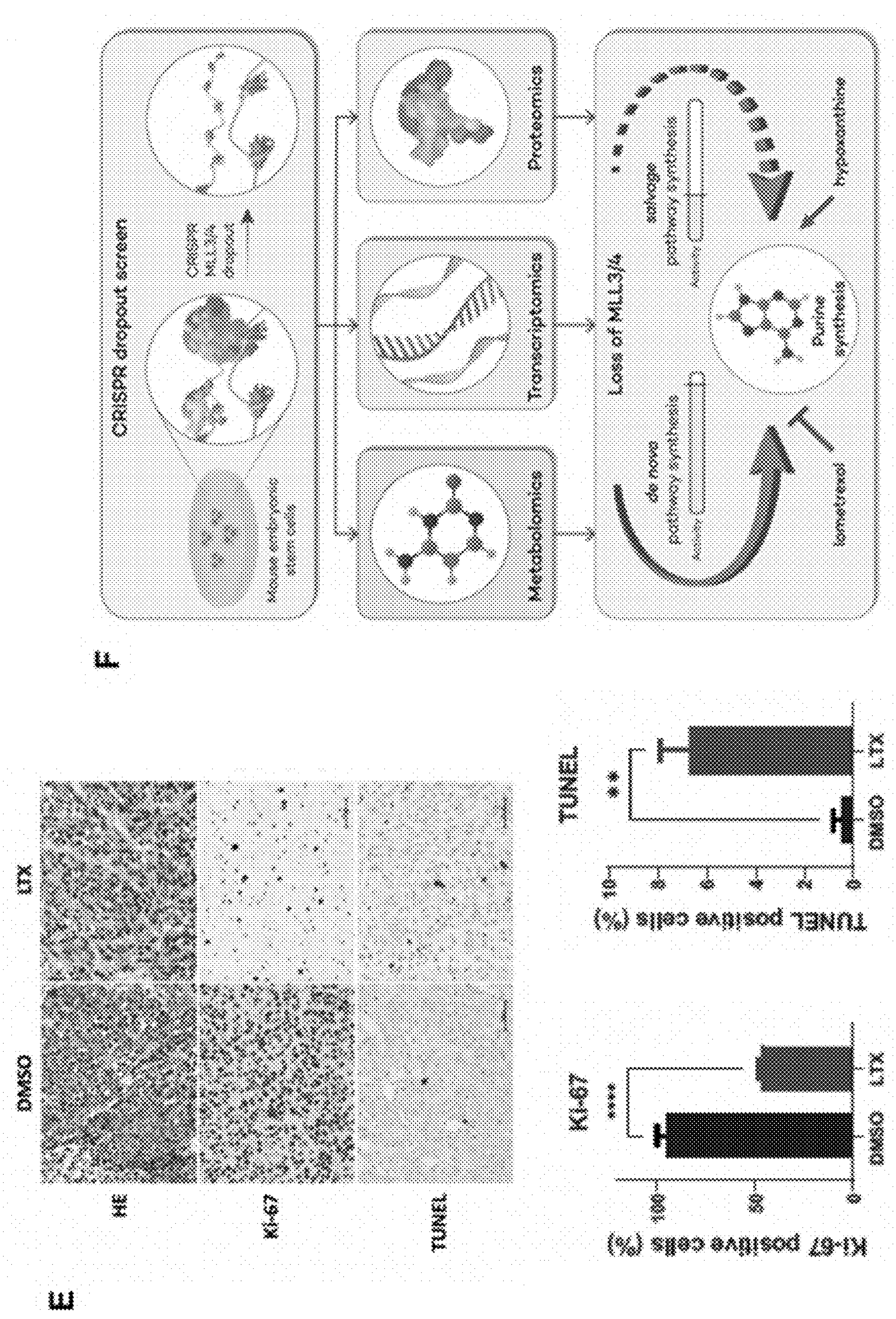
Figure 20:
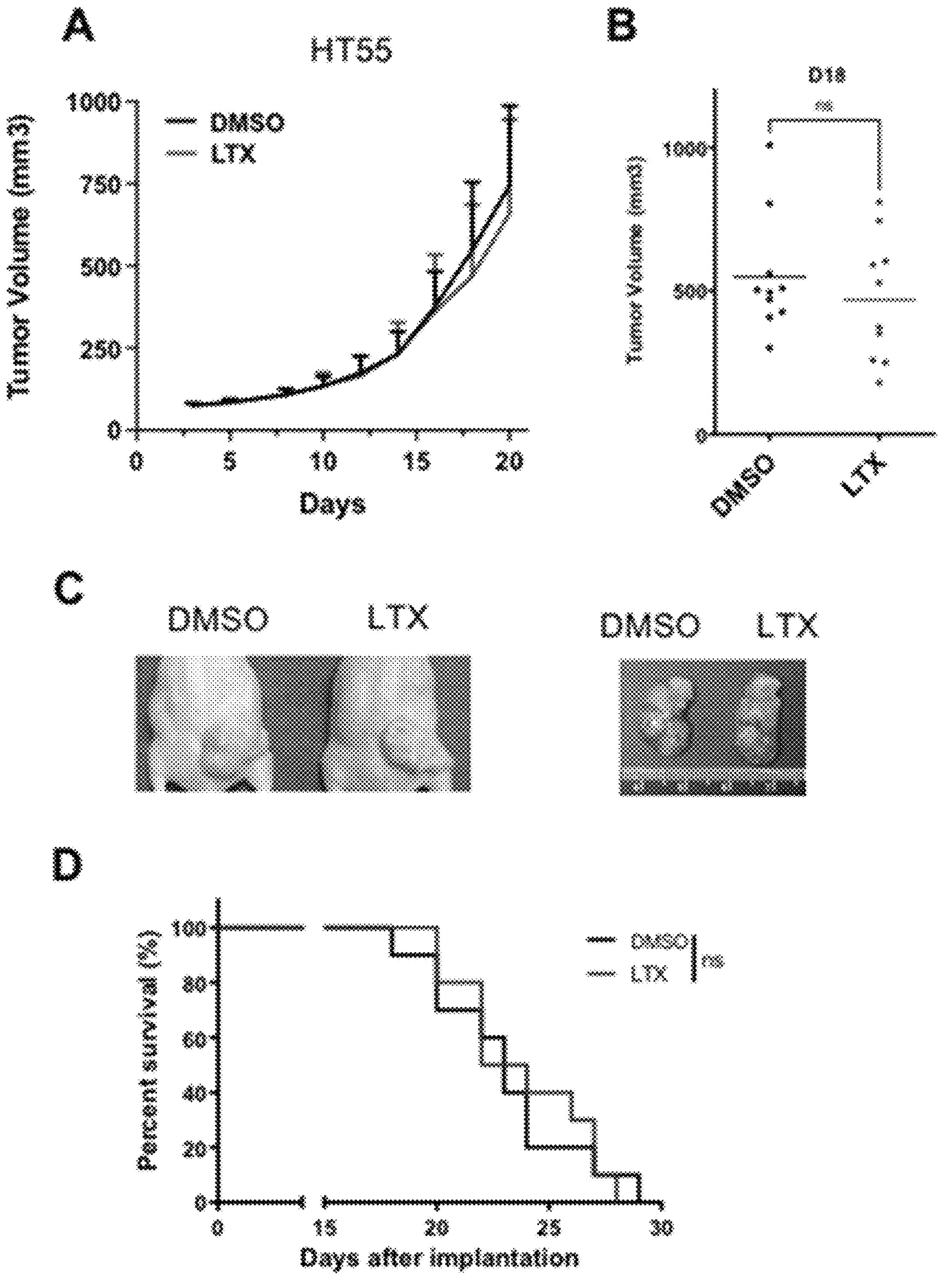
FIG. 20. Lometrexol application in MLL4 mutant tumors in the xenograft mouse models. (A-D) Tumor development after inoculation of $4\times10^6$ of HT55 cells into the nude mice. Mice with HT55 subcutaneous (sc) tumor were either treated with vehicle (DMSO, n=9) or LTX (15 mg/kg, n=9) daily for 7 days. (A) Growth plots for sc tumors in each treatment group were shown. Tumor volumes (mm3) show mean and upper SD. (B) Dot plot representation of sc tumor volume in mice at day 18 post-tumor cell injection. Unpaired t-test values for comparisons between DMSO and LTX treatment: ns, not statistically significant. (C) Photographs of nude mice (upper) and sc tumor taken from these mice (lower) in which HT55 cells were inoculated into the right flank. (D) Animal survival at the indicated days after inoculation. Log-rank test was used for comparisons between DMSO and LTX treatment. (E-H) Tumor development after inoculation of $4\times10^6$ of HCT116 cells into the nude mice. Mice with HCT116 subcutaneous (sc) tumor were either treated with vehicle (DMSO, n=9) or LTX (15 mg/kg, n=9) daily for 7 days. (E) Growth plots for sc tumors in each treatment group were shown. Tumor volumes (mm3) show mean and upper SD. (F) Dot plot representation of sc tumor volume in mice at day 12 post-tumor cell injection. Unpaired t-test values for comparisons between DMSO and LTX treatment: *, P<0.001. (G) Photographs of nude mice (upper) and sc tumor taken from these mice (lower) in which HCT116 cells were inoculated into the right flank. (H) Animal survival at the indicated days after inoculation. Log-rank test was used for comparisons between DMSO and LTX treatment: *, P<0.001.
Figure 20:
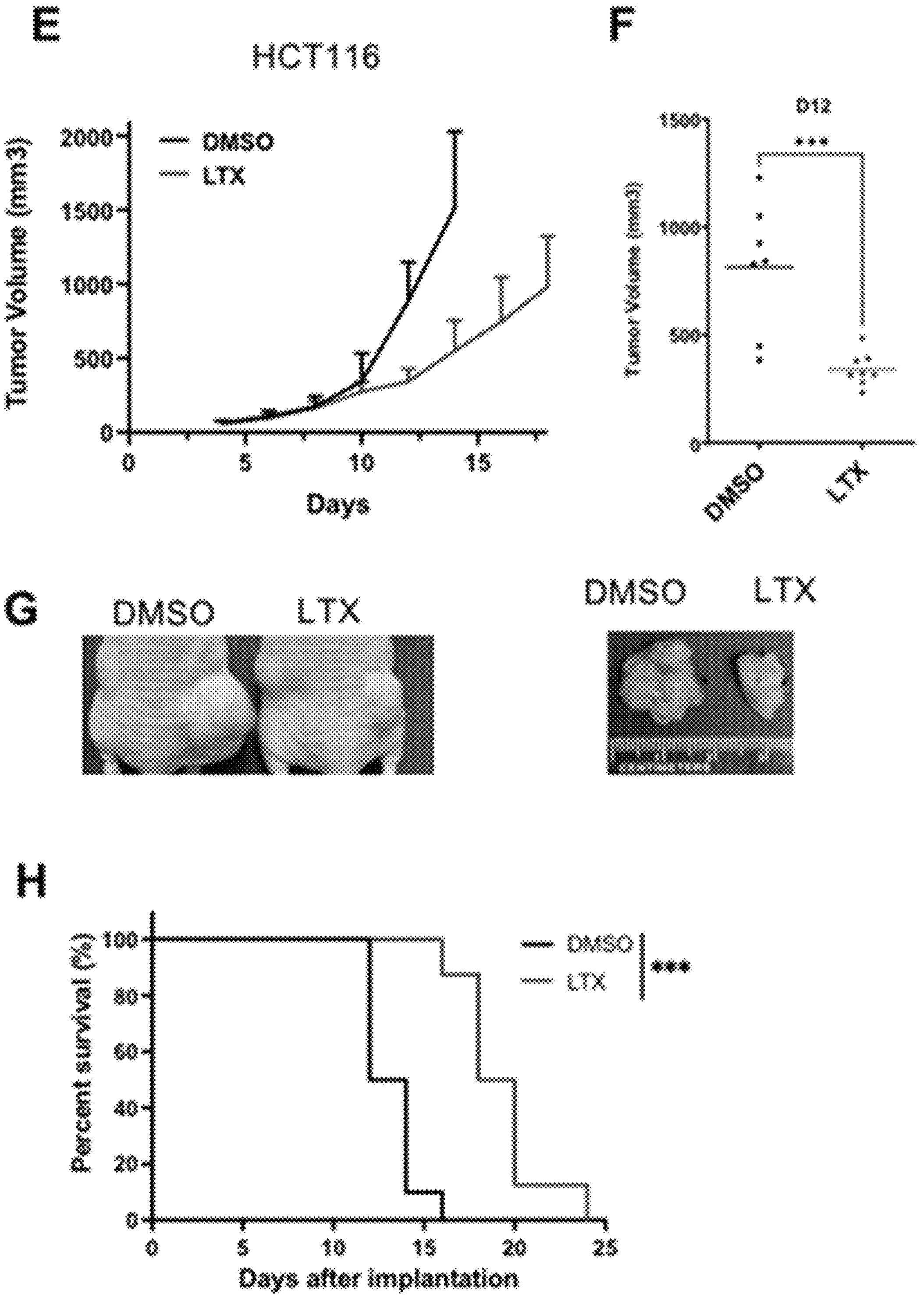

Inhibition of De Novo Purine Synthesis by Lometrexol Inhibits MLL4 Mutant Tumor Growth Based on the biological effects of LTX in vitro, we hypothesized that LTX treatment should suppress MLL4 mutant tumor growth in vivo in different xenograft models. To determine the anti-tumor activity of LTX in MLL4 mutant tumors, we subcutaneously implanted HCT116 cells into the right flank of mice and treated the mice with LTX (25 mg/kg) or vehicle control (DMSO) intraperitoneally when tumor size reached 100 $mm^3$ (day 6 after implantation). Mice were euthanized when the tumor size reached 1,000 $mm^3$. LTX treatment significantly inhibited the subcutaneous (sc) tumor growth ($P<0.0001$, FIG. 6A-C) and extend the survival of recipient mice with HCT116 sc xenografts compared to the control group ($P<0.0001$, FIG. 6D). Cell proliferation was significantly decreased accompanied with enhanced apoptosis (FIG. 6E). We next decreased the dosage of LTX to 15 mg/kg and compared the tumor growth of HT55 (MLL4 WT) and HCT116 (MLL4 mutant) (FIG. 20). HT55 colorectal was almost completely resistant to LTX (FIG. while HCT116 xenograft tumors maintained the sensitivity to LTX at a lower dose (FIG. 20E-H), indicating the mutation status of MLL4 may be useful for patient stratification and guide the treatment plan for cancer patients.

Discussion

Our study involving CRISPR dropout screen combined with metabolomics, transcriptomics, and proteomics approaches presented evidence of direct crosstalk between epigenetic alteration and metabolic dependency shift (FIG. 6F). We demonstrated that mESCs depleted of MLL3/4 acquired higher demand for purine nucleotide synthesis and elevated levels of purine metabolisms factors (FIG. 6F). De novo nucleotide synthesis is usually activated in proliferating cells in response to the enhanced demand for nucleotides to support RNA and DNA synthesis, and cancer cells tend to use de novo nucleotide synthesis (16). The observation that Mll3/4 knockout cells have elevated nucleotide synthesis flux implicates a cellular state alteration and further impairment during cell fate transition (9, 10).

Recurrent mutations in the genes encoding KMT2C (MLL3) and KMT2D (MLL4) are frequently found in a broad spectrum of cancers, and some of these mutations are believed to behave as driver mutations (7, 24-26). We and other groups have demonstrated that some of these mutations may act as major mediators in the pathogenesis of breast cancer (26), bladder cancer (22, 27, 28), prostate cancer (29), pediatric brain cancer medulloblastoma (30-32), and non-Hodgkin lymphoma (26, 33-36). In Kabuki syndrome, a multisystem disorder resulting in abnormalities during development caused by mutations in KMT2D and KDM6A genes, ~60% of KMT2D mutations result in protein truncation and loss of function (13-15). Although the occurrence of recurrent mutations in MLL4 has been well documented in these solid tumors, hematological malignancies, and Kabuki syndrome, the associated signaling pathways involved in how MLL4 mutation lesions drive oncogenesis and disease progression remain elusive. Recent exome sequencing and whole-genome sequencing studies revealed that MLL3/4 and UTX mutations are not only found in tumor tissues but also present in normal tissues such as esophagus (37, 38), endometrial epithelium (39), urothelium (22, 28), skin, and lung (40). This indicates the loss of function of MLL3/4 COMPASS mutations may lead to the macroscopic clonal expansion to further drive tumorigenesis when other key tumor suppressors are co-mutated. Our study showed a metabolic dependency shift caused by MLL3/4 loss. This provides insights into how clonal expansion may occur and how interventions of metabolism inhibition at early stages may prevent clonal expansion. It is worth investigating whether mutations of MLL3/4 and UTX elicited broad changes in gene expression that favor cell proliferation and activate proliferative signaling, further inducing metabolic programming. It is also worth elucidating whether these effects are dosage-dependent for MLL3 and MLL4 as most of the loss-of-function mutations are heterozygous in the patient tumor samples. We also noticed that the presence of multiple missense mutations may contribute to the abnormal protein functions such as the mutations in DLD1. MLL4 mutation occurs throughout the whole protein, and mutations may elicit different outcome depending on the different domains. Truncation mutations frequently result the loss of enzymatic activity since the SET/postSET domains are located on the very C-terminus of the protein. Other missense mutations occurring on the critical PHD fingers or other domains may also contribute to the abnormal protein functions, yet due to unknown mechanisms. One possibility is the compromised H4K16ac reader function since PHD6 finger of MLL4 (MLL4-PHD6) as a selective reader of the epigenetic modification H4K16ac shown in a previous study (41).

MLL4 has also been shown to suppress glycolytic genes in lung tissue, and deficiency of MLL4 confers glycolytic vulnerabilities in lung cancer (42) and melanoma (43). However, another study using MEFs and skin fibroblasts showed that MLL4 knockout cells display features of reduced mitochondrial oxygen consumption rate and glycolytic flux (44). The disparity may have arisen since MLL4 may regulate distinct sets of genes in different tissues based on their origin and depending on their differential enhancer activation. Nevertheless, our study and previous studies all address that MLL4 has an influential impact on function for multiple aspects of metabolism including nucleotide metabolism, glycolysis, and mitochondrial metabolism, and the use of metabolism inhibitors such as lometrexol to suppress MLL4 mutant cancer cell growth. Interestingly, we have noticed a consistent downregulation of mitotic genes such as PLK1 and AURKA after lometrexol treatment, so we defined the gene set as “lometrexol responsive mitotic gene signature”. Indeed, our RNA-seq results also echoed a previous study to propose the use of aurora kinase inhibitors for MLL4 mutant cancer (45).

Figure 3:
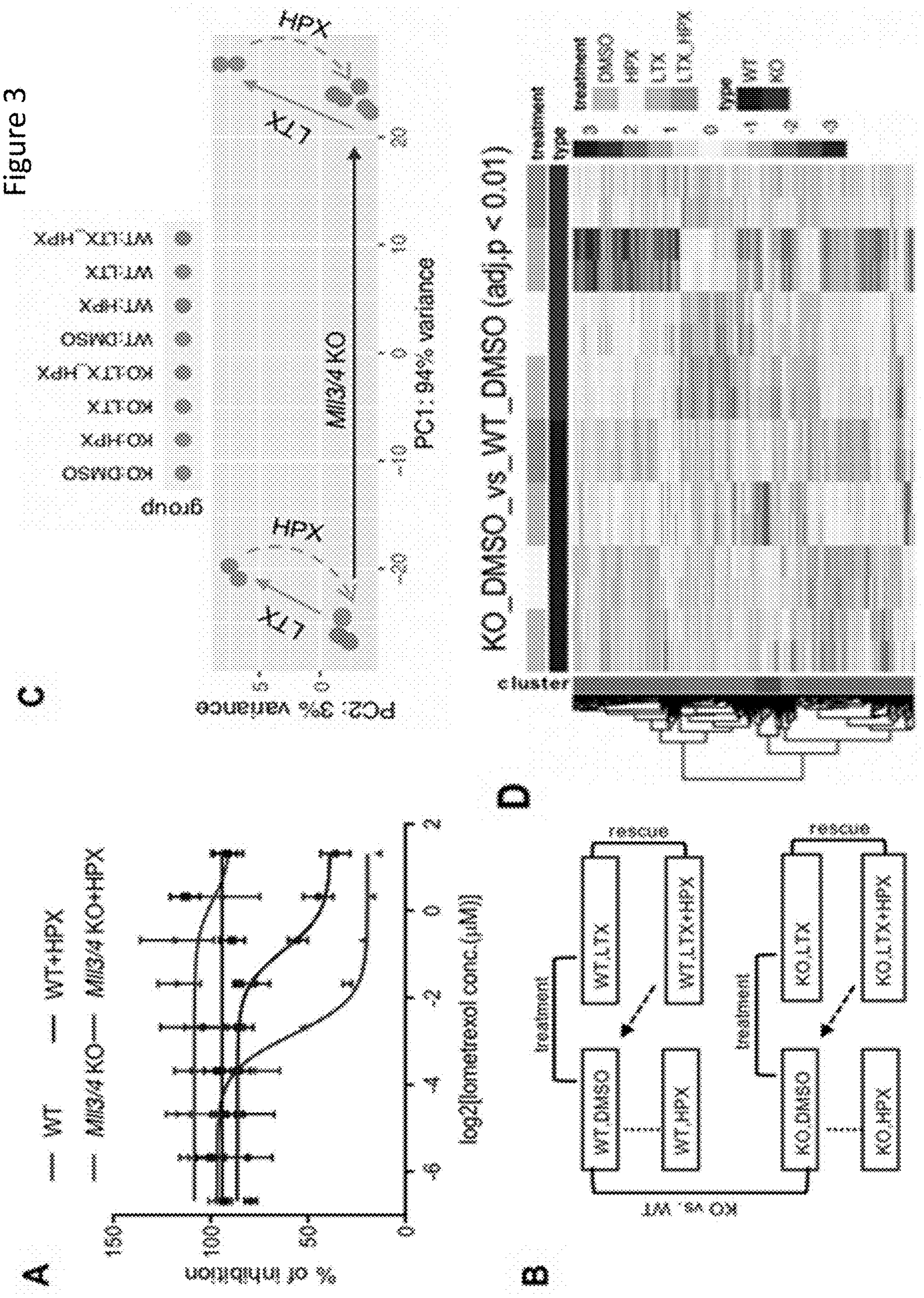
FIG. 3. Mll3/4 KO mESCs Confer Enhanced Sensitivity to Purine Synthesis Inhibition. (A) WT and Mll3/4 KO cells were treated with 0-2.5 μM lometrexol (LTX)−/+50 hypoxanthine (HPX) for 48 hours. CellTiter-Glo® luminescent cell viability assay was performed to determine the percentage of inhibition under these conditions. (B) WT and KO cells were treated with 0.3 μM LTX−/+50 μM HPX for 48 hours, and cells were harvested for RNA-seq. Differential gene expression analyses were performed with indicated comparisons. (C) Principal component analysis of RNA-seq in (B). (D) Hierarchical clustering heatmap showing differentially expressed genes in KO cells in comparison with WT cells. (E) Venn diagram showing the overlapped downregulated genes with LTX treatment in WT and KO cells. (F) Pathway enrichment analysis of the commonly downregulated genes in WT and KO cells with LTX treatment. (G) Pathway enrichment analysis of uniquely downregulated genes in WT cells with LTX treatment. (H) Pathway enrichment analysis of uniquely downregulated genes in Mll3/4 KO cells with LTX treatment.
Figure 3:
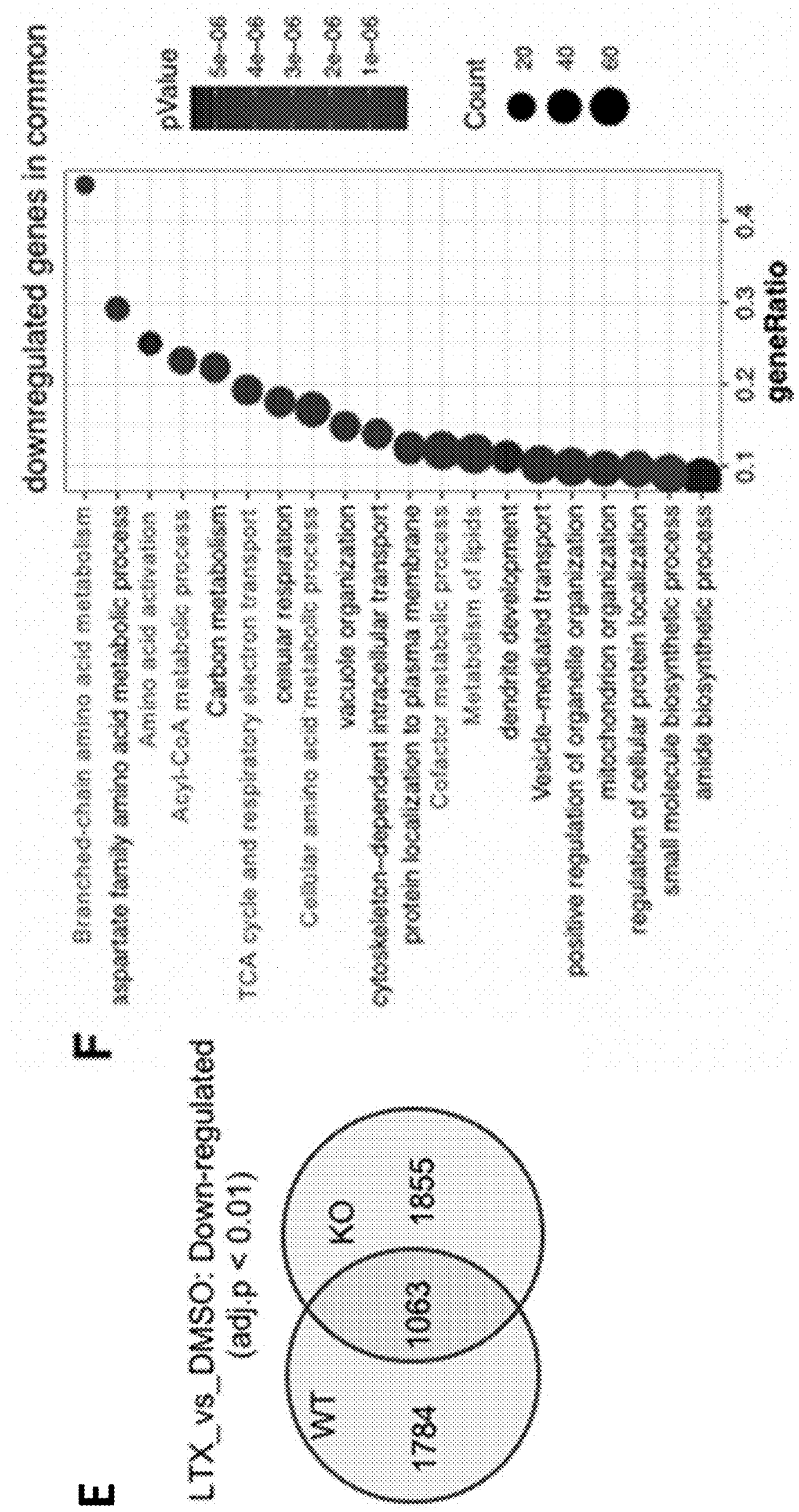
Figure 3:
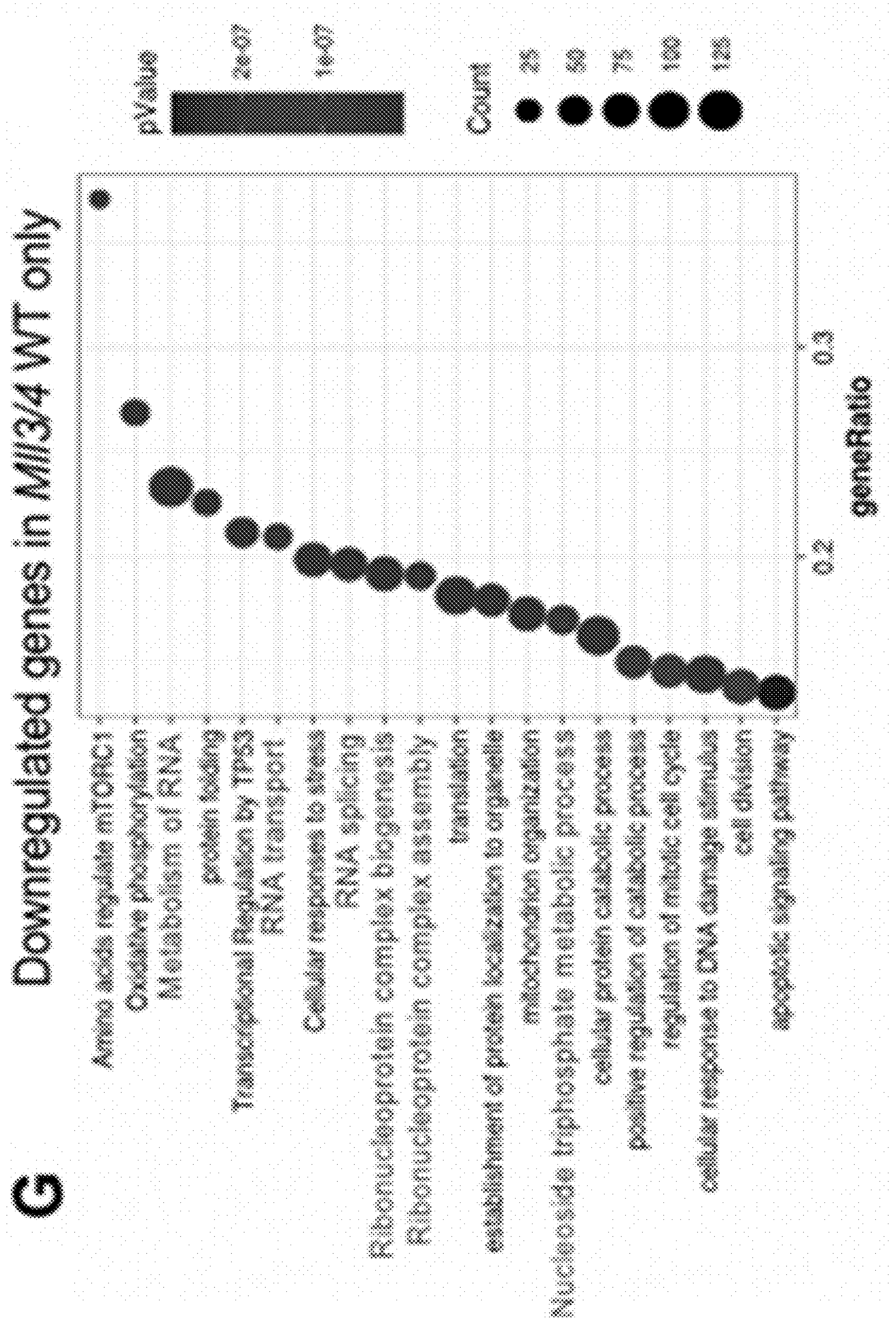
Figure 3:
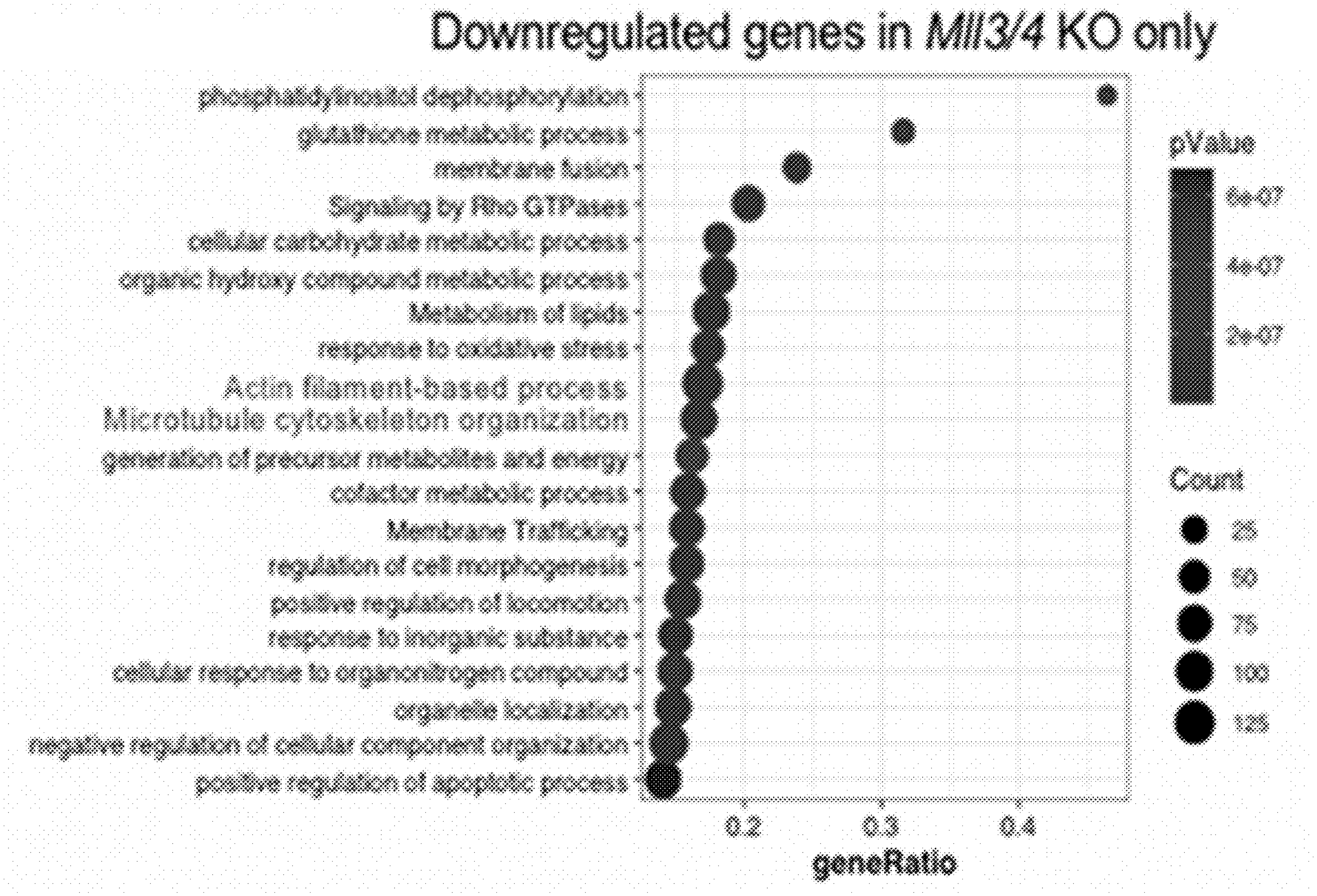
Figure 4:
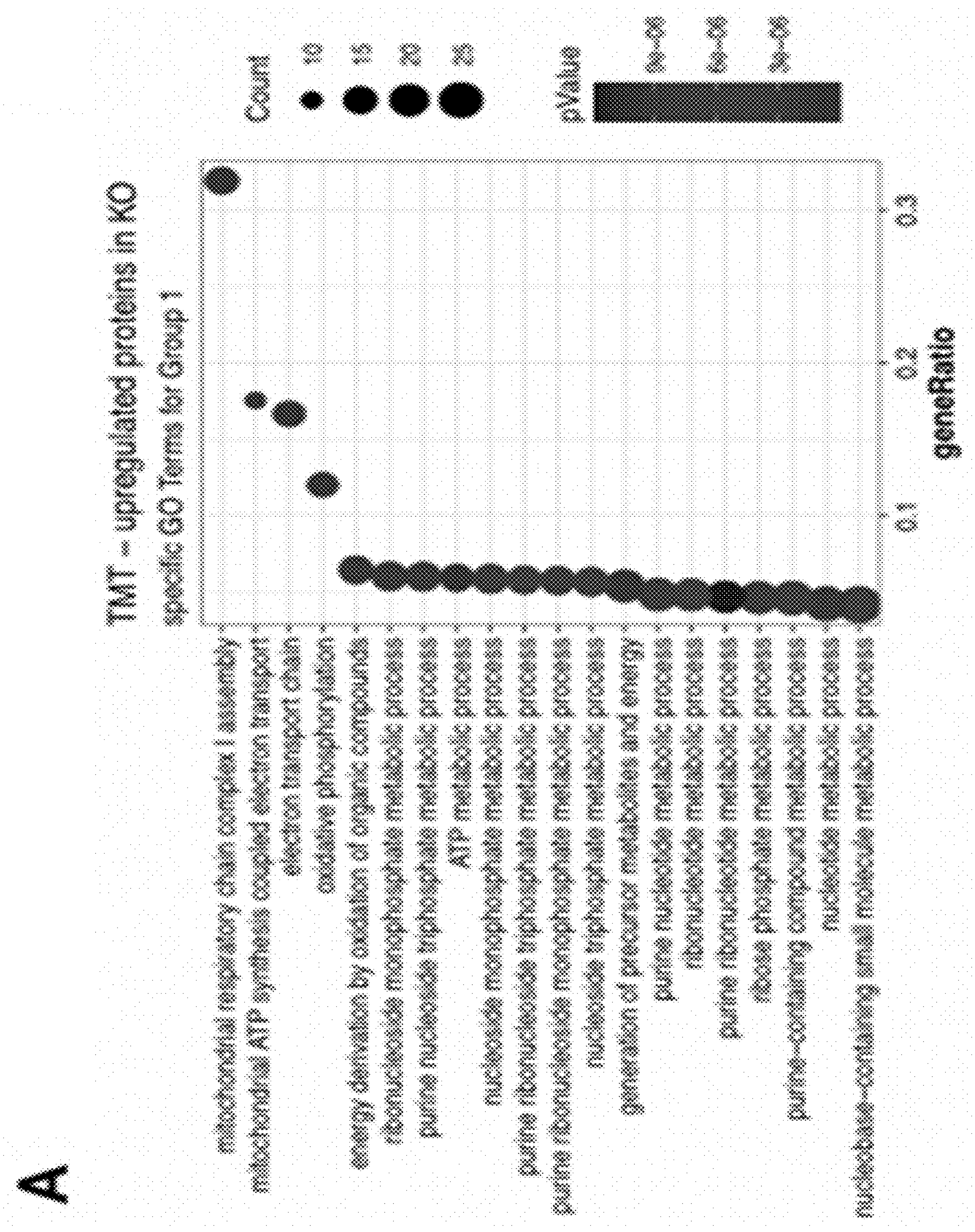
FIG. 4. Purine metabolism possessive upregulation in Mll3/4 KO cells with integration study of a tandem mass tag (TMT) Proteomics Profiling, RNA-seq and Hi-C. (A) The subgroups' identity of the biological process terms within the top upregulated gene ontology term. (B) The correlation plot showing the log 2 fold change of all the common targets detected in TMT and RNA-seq, n=6700. Top 20 up- or down-regulated genes were highlighted that were changed both at RNA and protein levels. (C) Z-score hierarchical heatmap showing the change of purine metabolism genes in group 1 with each target knockdown compared with PLKO control. The log 2FC of Mll3/4 KO versus WT RNA-seq values were plotted with the same gene cluster order. (D) Hi-C was performed in WT and Mll3/4 KO mESCs. Compartmentalization saddle plots of Hi-C data for WT and Mll3/4 KO ES cells. Saddle plots were calculated using cooltools (66). Average intra-chromosomal interaction frequencies were normalized by expected interaction frequency and distance. Bins were sorted by eigenvector PC1 values. B-B interactions are located in the upper-left corner of saddle plots and A-A interactions are located in the lower-right corner. (E) Saddle plot of Log 2FC of Mll3/4 KO versus WT. (F) The C-score was calculated for each 100-kb genomic bin to define A and B compartments. Compartment switching, decompaction and compaction upon Mll3/4 loss is shown in the scatter plot. Lengths of genomic regions (no. of bins×100 kb) and percentage of compartment shifts are shown. (G) Genes located in B-to-A shifts, stable compartments and A-to-B shifts were selected (>=1/2 gene length located within the compartments). 1301 and 229 genes were found in B-A and A-B group, respectively. Genes with detectable expression levels were further selected (361 for B-A and 91 for A-B) for the log FC gene expression of KO versus WT in the box plot.
Figure 4:
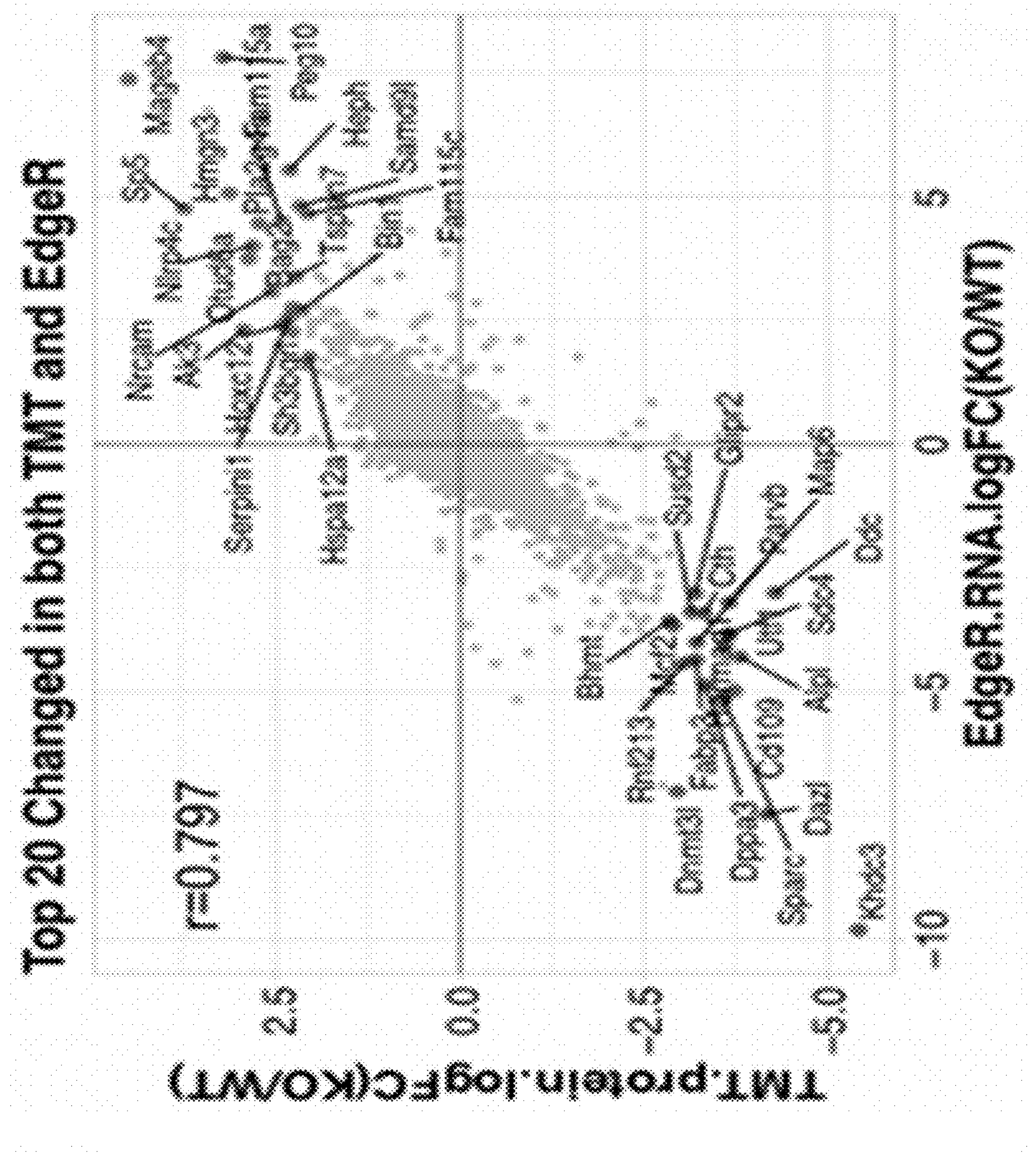
Figure 4:
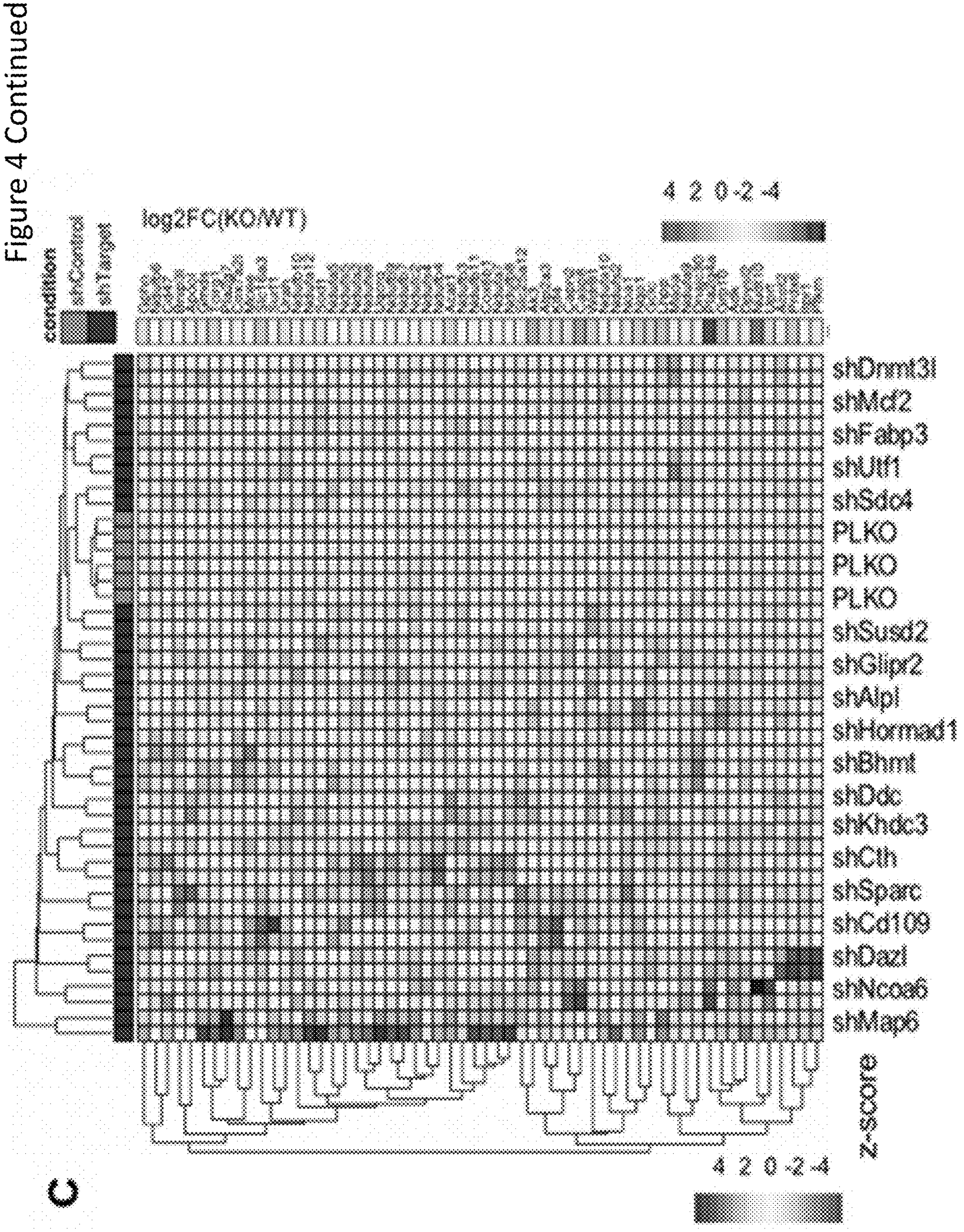
Figure 4:
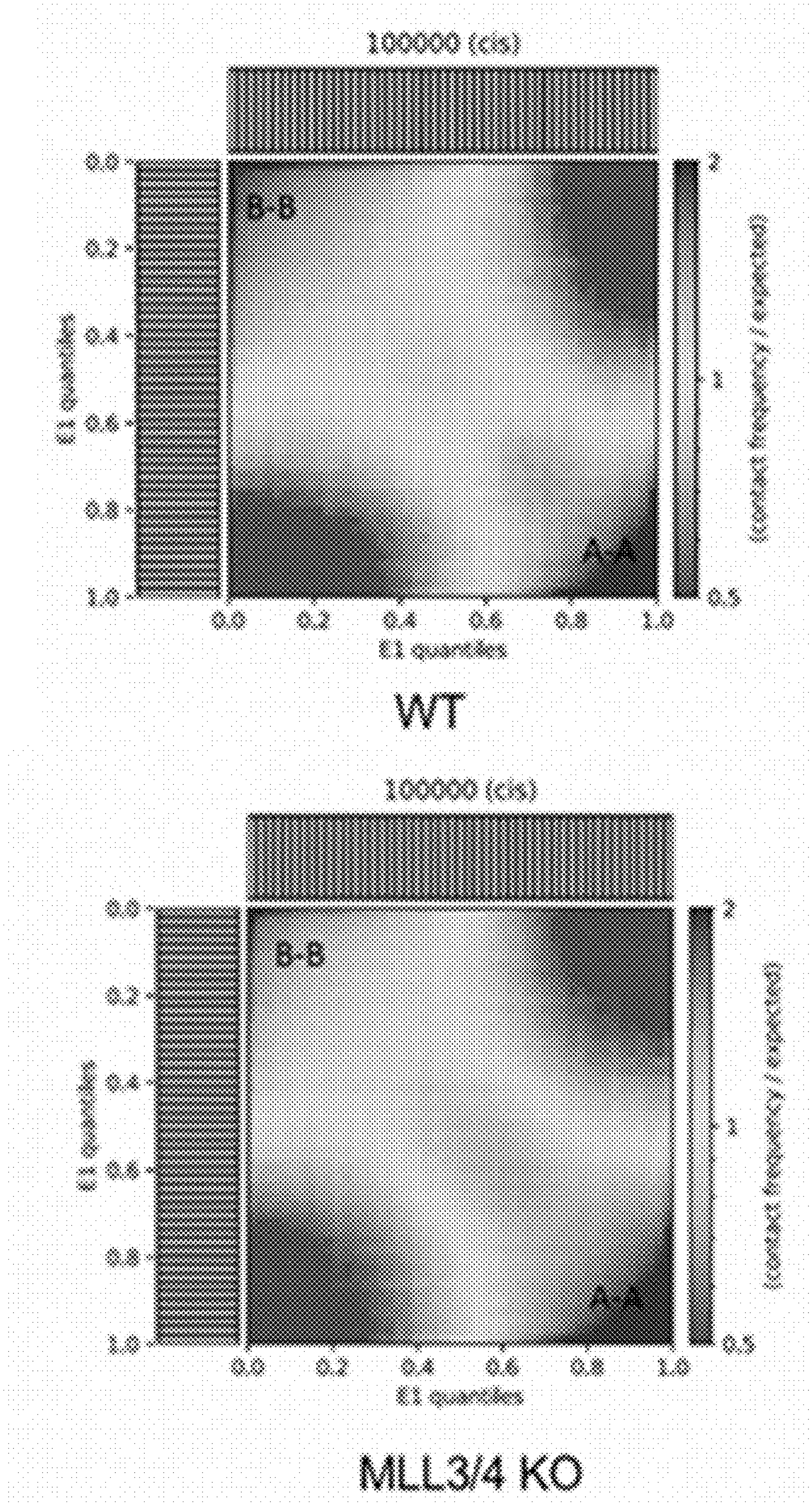
Figure 4:
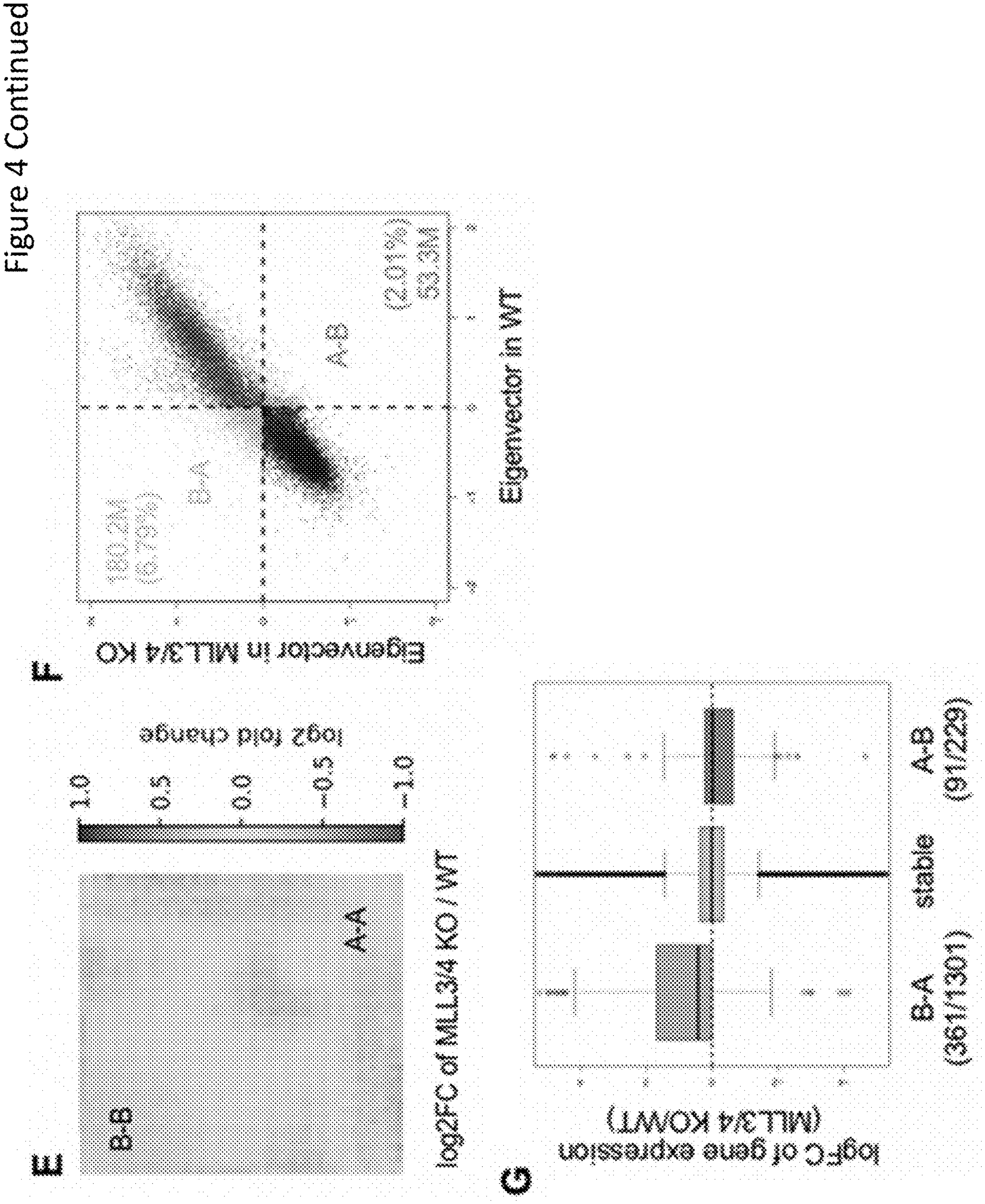

The enhanced purine synthesis flux in MLL3/4 knockout cells displayed increased sensitivity to nucleotide synthesis inhibition upon lometrexol treatment (FIG. 3). Metabolic therapies against nucleotide metabolism and amino acid metabolism have been widely tested and used for a variety of cancers (46). We demonstrated that MLL4 mutant colorectal cancer cells are selectively sensitive to lometrexol treatment. There are multiple nucleotide synthesis inhibitors that have been used in clinical trials (47). Further investigating if mutations of MLL3/4 COMPASS predict a higher sensitivity and response to these nucleotide synthesis inhibitors in human cancers and developmental diseases will be critical for enhancing patient treatments. Overall, our study provides insights into the identification of novel therapeutic targets and approaches to exploiting the reprogrammed regulation of metabolic pathways in human cancer for future clinical translation.

Methods

ESC Culture, shRNA Knockdown, and CRISPR/Cas9-Guided Gene Editing

FHC, CACO2, SW1417, HT55, SW480, DLD1, HCT116 and RKO cells were purchased from ATCC. FHC cells were cultured with DMEM/F12 with 25 mM HEPES, 10 ng/mL choleratoxin, 0.005 mg/mL insulin, 0.005 mg/mL transferrin, 100 ng/mL hydrocortisone, 20 ng/mL hEGF, and 10% FBS. Caco2 and HT55 were grown in DMEM with 20% FBS. SW1417, SW480, HCT116, and RKO were grown in DMEM with 10% FBS. DLD1 was grown in RPMI-1640 with 10% FBS. V6.5 ESCs were grown in N2B27 medium supplemented with two inhibitors (2i) and LIF as described previously (3). The lentiviral constructs containing shRNA against all targets was purchased from Millipore Sigma. shRNA sequences are listed in Table 1. Lentiviruses were packaged with psPAX2 and CMV-VSVG in 293T cells. After 24 hours and 48 hours post transfection, culture media was collected, passed through 0.45 μm filters, concentrated with lenti-X concentrator (Takara Bio) and resuspended in mouse ESC media. ESCs were infected with lentiviruses and selected with puromycin (2 μg/ml) for 6 days before collecting for RNA extraction.

For CRISPR knockout of Mll3 and Mll4, mESCs were electroporated with plasmids containing sgRNAs in px459 backbone, selected with puromycin (2 μg/ml) for 48 hours, and grown in 2i/LIF medium without puromycin until the cell clones were ready to be picked. gRNA sequences used in this study are listed as follows: Mll4 KO, TGGGGATGGACAGCCCGACG (left) SEQ ID NO: 1, GGTATAATCAATCCGTCCTT (right) SEQ ID NO: 2; Mll3 KO, CATATGCTGTAGGAACCGTA (left) SEQ ID NO: 3; TTGGGACAGGTACGAAAATA (right) SEQ ID NO: 4.

| Mouse shRNA | | | | | | |
|---|---|---|---|---|---|---|
| Clone ID | Oligo Seq | Symbol | RefSeq ID | Gene ID | Gene Description | SEQ ID NO: |
| TRCN 0000081503 | CCGGGCAGGAA CAGAAGTTCGC TATCTCGAGATA GCGAACTTCTGT TCCTGCTTTTTG | Alpl | NM_007431 | 11647 | alkaline phosphatase 2, liver | 5 |
| TRCN 0000080349 | CCGGCCTAGAC AACGACAAGTA CATCTCGAGAT GTACTTGTCGTT GTCTAGGTTTTT G | Sparc | NM_009242 | 20692 | secreted acidic cysteine rich glycoprotein | 6 |
| TRCN 0000081712 | CCGGCTTCGACC AAACCGTTTCTC TCTCGAGAGAG AAACGGTTTGG TCGAAGTTTTTG | Utf1 | NM_009482 | 22286 | un-differentiated embryonic cell transcription factor 1 | 7 |
| TRCN 0000102500 | CCGGGCCTTGTT GATCTATCTTGT ACTCGAGTACA AGATAGATCAA CAAGGCTTTTTG | Dazl | NM_010021 | 13164 | deleted in azoospermia-like | 8 |
| TRCN 0000105190 | CCGGGCCTACT ACCATCATCGA GAACTCGAGTT CTCGATGATGGT AGTAGGCTTTTT G | Fabp3 | NM_010174 | 14077 | fatty acid binding protein 3, muscle and heart | 9 |
| TRCN 0000340859 | CCGGAGCAAGC ACTAAGGATCA AAGCTCGAGCT TTGATCCTTAGT GCTTGCTTTTTT G | Map6 | NM_010837 | 17760 | microtubule-associated protein 6 | 10 |
| TRCN 0000331554 | CCGGGATTCGA GAGACAGAGGT CATCTCGAGAT GACCTCTGTCTC TCGAATCTTTTT G | Sdc4 | NM_011521 | 20971 | syndecan 4 | 11 |
| TRCN 0000097583 | CCGGCGCTTAA ATGCCGGAGAA GTTCTCGAGAA CTTCTCCGGCAT TTAAGCGTTTTT G | Bhmt | NM_016668 | 12116 | betaine-homocysteine methyl-transferase | 12 |
| TRCN 0000108475 | CCGGGCCTTTAA TATGGACCCTGT TCTCGAGAACA GGGTCCATATTA AAGGCTTTTTG | Ddc | NM_016672 | 13195 | dopa decarboxylase | 13 |
| TRCN 0000039105 | CCGGCTTCTGGA TATTCATGGACA ACTCGAGTTGTC CATGAATATCC AGAAGTTTTTG | Dnmt31 | NM_019448 | 54427 | DNA (cytosine-5-)-methyl-transferase 3-like | 14 |
| TRCN 0000173430 | CCGGCCTAGAG TACAGGGTGAA CATCTCGAGAT GTTCACCCTGTA CTCTAGGTTTTT TG | Ncoa6 | NM_019825 | 56406 | nuclear receptor coactivator 6 | 15 |

-continued

| | | | | | | |
|---|---|---|---|---|---|---|
| TRCN 0000446257 | CCGGGGCGAGCTGAGATTTGGATATCTCGAGATATCCAAATCTCAGCTCGCCTTTTTTG | Khdc3 | NM_025890 | 66991 | RIKEN CDNA 2410004A20 gene | 16 |
| TRCN 0000200876 | CCGGGAAGAGAAGTCTTCGTCAATTCTCGAGAATTGACGAAGACTTCTCTTCTTTTTTG | Hormad1 | NM_026489 | 67981 | HORMA domain containing 1 | 17 |
| TRCN 0000110910 | CCGGCGCTAATTTGATCCTGTGTTTCTCGAGAAACACAGGATCAAATTAGCGTTTTTG | Glipr2 | NM_027450 | 384009 | GLI pathogenesis-related 2 | 18 |
| TRCN 0000126003 | CCGGCGAGACCCATTGGCAATACTACTCGAGTAGTATTGCCAATGGGTCTCGTTTTTG | Susd2 | NM_027890 | 71733 | sushi domain containing 2 | 19 |
| TRCN 0000112644 | CCGGCGGGACGCCTTCGATACTCTTCTCGAGAAGAGTATCGAAGGCGTCCCGTTTTTG | Parvb | NM_133167 | 170736 | parvin, beta | 20 |
| TRCN 0000042657 | CCGGGCTGACATACATTGATGACAACTCGAGTTGTCATCAATGTATGTCAGCTTTTTG | Mcf2 | NM_133197 | 109904 | mcf.2 transforming sequence | 21 |
| TRCN 0000420527 | CCGGCACCTTCATGTCTGCATATTTCTCGAGAAATATGCAGACATGAAGGTGTTTTTG | Cth | NM_145953 | 107869 | cystathionase (cystathionine gamma-lyase) | 22 |
| TRCN 0000080513 | CCGGCCAGTGATGCTGTAAGTCATTCTCGAGAATGACTTACAGCATCACTGGTTTTTG | Cd109 | NM_153098 | 235505 | CD109 antigen | 23 |

Human shRNA

| Clone ID | Target Sequence | Symbol | RefSeq ID | Gene ID | Gene Description | SEQ ID NO: |
|---|---|---|---|---|---|---|
| TRCN 0000289428 | CCCTAACTGTTGTCATGGCAA | GART #1 | NM_000819 | 2618 | AIRS, GARS, GARTF, PAIS, PGFT, PRGS | 24 |
| TRCN 0000289431 | GCACAGTCTCATCATGTCAAA | GART #2 | NM_000819 | 2618 | AIRS, GARS, GARTF, PAIS, PGFT, PRGS | 25 |
| TRCN 0000045774 | CGCAGTGTGAAATGATTCCAA | PAICS #1 | NM_006452 | 10606 | ADE2, ADE2H1, AIRC, PAIS | 26 |

-continued

| | | | | | | |
|---|---|---|---|---|---|---|
| TRCN 0000045775 | GCTGCTCAGAT ATTTGGGTTA | PAICS #2 | NM_006452 | 10606 | ADE2, ADE2H1, AIRC, PAIS | 27 |
| | | | qRT-PCR primers | | | |
| Ak3-QF | GCCTGAAGGGA TGTGGTATTAG | | | | | 28 |
| Ak3-QR | CCTGTTAAGGTA GCAGTGAGTT | | | | | 29 |
| Nqo1-QF | GAGAAGAGCCC TGATTGTACTG | | | | | 30 |
| Nqo1-QR | ACCTCCCATCCT CTCTTCTT | | | | | 31 |
| Gapdh-QF | AACAGCAACTC CCACTCTTC | | | | | 32 |
| Gapdh-QR | CCTGTTGCTGTA GCCGTATT | | | | | 33 |

Antibodies and Western Blot

The following antibodies are used in this study: anti-H3K4me1 (Cell Signaling Technology (CST), #5326), anti-H3K4me2 (generated in-house), anti-H3K4me3 (CST, #9751), anti-H3K27ac (CST, #8173), H3K27me3 (CST, #9733), anti-MLL3 NT (generated in-house), anti-MLL3 MT (generated in-house), anti-MLL4 NT (generated in-house), anti-MLL4 CT (generated in-house), anti-MLL1C (CST, #14197), anti-RBBP5 (Bethyl Laboratories, A300-109A), anti-NCOA6 (Bethyl Laboratories, A300-410A), anti-UTX (CST, #33510), anti-PTIP (Bethyl Laboratories, A300-370A), ASH2L (CST, #5019), H3 Ser10-p (CST #53348), CDT1 (CST, #8064), Cyclin B1 (CST, #12231), Geminin (CST, #52508), Cyclin E1 (CST, #20808), Cyclin A2 (CST, #91500), p-cdc2 (CST, #4539), PARP (CST, #9542) Caspase3 (CST, #9662), anti-GART (Santa Cruz Biotechnology, sc-166447), anti-PAICS (Proteintech, 12967-1-AP), Hsp90 (Santa Cruz Biotechnology, sc-13119), and anti-β-tubulin (Developmental Studies Hybridoma Bank, E7). Western blot analysis was performed as previously described (48).

Genome-Scale CRISPR-Cas9 Knockout (GeCKO) Screening

Mouse Brie CRISPR knockout pooled library was a gift from David Root and John Doench (Addgene #73633) (49). A total of $6.3\times10^7$ WT or Mll3/4 KO cells were infected with the library at an MOI of 0.5 to ensure most cells receive only one genetic perturbation, and the sgRNA library is well represented in the pool of cells for infection. WT and Mll3/4 knockout mouse ES cells were harvested at day 3 as baseline and selected with puromycin (2 μg/mL) for 15 or 21 days before harvesting. Genomic DNA was extracted, and the library was constructed. After sequencing the library, data analyses were performed with MAGeCK RRA algorithm or MLE module (17). Data visualization was performed with MAGeCKFlute (50).

NGS Data Processing

RNA-seq and ChIP-seq samples were sequenced with Illumina NextSeq technology, and output data were processed with bcl2fastq. Sequence quality was assessed using FastQC v 0.11.2 (51), and quality trimming was done using Trimmomatic (52). RNA-seq and ChIP-seq reads were aligned to the mm9 genome using TopHat v2.0.9 (53) and Bowtie v0.12.9 (54), and only uniquely mapped reads with a two-mismatch threshold were considered for downstream analysis. Gene annotations from Ensembl 67 were used. Output bam files were converted into bigwig track files to display coverage throughout the genome (in RPM) using the GenomicRanges package (55) as well as other standard Bioconductor R packages.

RNA-Seq Analysis

Gene count tables were constructed using HTseq (56) with Ensembl gene annotations and used as input for edgeR 3.0.8 (57). Genes with Benjamini-Hochburg adjusted p-values less than were differentially expressed. Batch effects were removed using ComB at-seq on the raw read counts (58). Pathway analysis was performed with Metascape (59).

ChIP-Seq Analysis $5\times10^7$ cells were used for each ChIP assay and performed as previously described (60). Peaks were called with MACS v1.4.2 using default parameters (61). Peak annotation, pathway analysis, and visualization were performed with ChIP-seeker (62). Metaplots were generated using ngsplot (63). Bedtools was used to determine the raw counts at the merged peaks (64). Using in-house perl scripts, raw counts at each peak were converted to RPKM values with total library counts, and log 2 fold change values between conditions were computed with these normalized values. Nearest genes were identified using in-house perl scripts based on distances between peak centers and TSSs.

Hi-C and Data Processing

Hi-C samples were prepared with Arima Hi-C kit according to the manufacture's instruction. The adapters of the Hi-C raw FASTQ files were trimmed and then the trimmed files were mapped against mm9 mouse reference genome using runHi-C pipeline. Specifically, Burrows-Wheeler Aligner was used for the FASTQ file alignment and aligned reads with low quality, and PCR duplicates were filtered. Aligned reads were then paired on the basis of read pairs and filtered for fragments that contain ligations of at least two different restriction fragments. These reads were then binned at 5-kb resolution.

Metabolomics Study

Metabolomics study was performed by BIDMC Mass Spectrometry Facility at Beth Israel Deaconess Medical Center. For global steady state metabolomics, cells were grown to ~80% confluency and washed with respective medium. Fresh medium was added 2 hours prior to metabolite collection. For tracing studies, cells were washed with metabolite free medium and medium containing 4 mM $^{15}$N-glutamine or 100 μM $^{13}$C-hypoxanthine 1 hour prior to metabolite collection. To collect metabolites, cells were fixed in 80% HPLC grade methanol in LC-MS water and kept at −80° C. for 15 minutes. Next, cells were scraped off the plates on dry ice and transferred to 10 ml conical tubes. This was repeated twice, and all extractions were collected and completed dried with Nitrogen gas N-EVAP. Cell pellets were resuspended in 8M urea. Protein concentration of cell lysates were quantified with Bradford assay for normalization purposes.

Tandem Mass Tag (TMT) Proteomics Study

TMT study was performed by Thermo Fisher Scientific Center for Multiplexed Proteomics at Harvard Medical School. Samples were prepared in 0.5 ml lysis buffer (8M Urea, 200 mM EPPS, pH 8.5, Protease & phosphatase inhibitors). Protein Quantification using the micro-BCA assay by Pierce. After, protein quantification lysates were immediately reduced with TCEP and alkylated with iodoacetamide. ~300 μg of each sample was precipitated using methanol/chloroform. Digestion was performed using LysCand trypsin. ~100 μg of each sample was labeled with six TMT10-plex reagents. A small aliquot of each sample was combined and analyzed by LC-MS2 to evaluate labeling efficiency and mixing ratios. Peptide N terminal ends were labeled >99% by TMT reagents. Samples were combined in full, desalted, and fractionated by HPLC bRP. The sample was fractionated into two sets: Set 1 consists of 12 fractions, each fraction in this set is made up of the orange numbers for an entire column, e.g., 1, 25, 49, 73; Set 2 consists of 12 fractions from the black numbers for an entire column. One complete set (12 fractions) from HPRP was analyzed on an OrbitrapEclipse mass spectrometer using a real time search method. Peptides were separated using a gradient from 5% to 30% acetonitrile, in 0.125% formic acid, for over 90 minutes. Peptides were detected (MS1) and quantified (MS3) in the Orbitrap. Peptides were sequenced (MS2) in the ion trap. Peptides are selected for sequencing in MS1 scans. MS2 spectra are used for identifying peptides, and MS3 spectra are used for quantification via TMT reporter ions. mMS2 spectra were searched using the SEQUEST algorithm against a Uniprotcomposite database derived from the mouse proteome, known contaminants, and reverse compliment sequences. Peptide spectral matches were filtered to a 1% false discovery rate (FDR) using the target-decoy strategy combined with linear discriminant analysis. Proteins were quantified only from peptides with a summed SN threshold of >=100. Quantified protein and peptide numbers do not include contaminant or reverse sequence identifications.

Xenograft Studies

Six-week-old female athymic mice (nu/nu genotype, BALB/c background) were purchased from Envigo (Indianapolis, IN, USA) and housed under aseptic conditions. HT55 or HCT116 cells were implanted into the flank of athymic mice as previously described (65). Briefly, 4×10$^{6}$ cells, in 0.4 ml of cell culture media with matrigel (BD Bioscience) at 1:1 ratio, were injected in the right flank of mice under anesthetization by isoflurane. Mice were randomly assigned to vehicle (DMSO, n=9) and LTX treatment (25 mg/kg for 7 days, n=9) groups when the size of tumor reached at 100 mm3 (day 6 after implantation). The tumor sizes were measured on alternate days and the mice were euthanized when the tumor size reached 1000 mm$^{3}$. All protocols, described below, were approved by the Northwestern University Institutional Animal Care and Use Committee.

Statistical Analysis

For in vivo study, the Kaplan-Meier estimator and Prism software were used to generate and analyze survival plots. Differences between survival plots were calculated using a log-rank test. A 2-tailed unpaired t-test was used (GraphPad Software, San Diego, CA, USA) for comparison the tumor size between each treatment group.

REFERENCES

1. D. Hu et al., The MLL3/MLL4 branches of the COMPASS family function as major histone H3K4 monomethylases at enhancers. *Mol Cell Biol* 33, 4745-4754 (2013).
2. H. M. Herz et al., Enhancer-associated H3K4 monomethylation by Trithorax-related, the *Drosophila* homolog of mammalian M113/M114. *Genes Dev* 26, 2604-2620 (2012).
3. K. Cao et al., SET1A/COMPASS and shadow enhancers in the regulation of homeotic gene expression. *Genes Dev* 31, 787-801 (2017).
4. R. Rickels et al., A small UTX stabilization domain of Trr is conserved within mammalian MLL3-4/COMPASS and is sufficient to rescue loss of viability in null animals. *Genes Dev,* (2020).
5. J. H. Kim et al., UTX and MLL4 coordinately regulate transcriptional programs for cell proliferation and invasiveness in breast cancer cells. *Cancer Res* 74, 1705-1717 (2014).
6. S. P. Wang et al., A UTX-MLL4-p300 Transcriptional Regulatory Network Coordinately Shapes Active Enhancer Landscapes for Eliciting Transcription. *Mol Cell* 67, 308-321 e306 (2017).
7. C. C. Sze, A. Shilatifard, MLL3/MLL4/COMPASS Family on Epigenetic Regulation of Enhancer Function and Cancer. *Cold Spring Harb Perspect Med* 6, (2016).
8. D. Ashokkumar et al., MLL4 is required after implantation, whereas MLL3 becomes essential during late gestation. *Development* 147, (2020).
9. K. Cao et al., An M114/COMPASS-Lsdl epigenetic axis governs enhancer function and pluripotency transition in embryonic stem cells. *Sci Adv* 4, eaap8747 (2018).
10. C. Wang et al., Enhancer priming by H3K4 methyltransferase MLL4 controls cell fate transition. *Proc Natl Acad Sci USA* 113, 11871-11876 (2016).
11. H. M. Herz, D. Hu, A. Shilatifard, Enhancer malfunction in cancer. *Mol Cell* 53, 859-866 (2014).
12. M. A. Morgan, A. Shilatifard, Chromatin signatures of cancer. *Genes Dev* 29, 238-249 (2015).
13. S. B. Ng et al., Exome sequencing identifies the cause of a mendelian disorder. *Nat Genet* 42, 30-35 (2010).
14. C. K. Cheon et al., Identification of KMT2D and KDM6A mutations by exome sequencing in Korean patients with Kabuki syndrome. *Journal of human genetics* 59, 321-325 (2014).
15. D. Cocciadiferro et al., Dissecting KMT2D missense mutations in Kabuki syndrome patients. *Hum Mol Genet* 27, 3651-3668 (2018).
16. E. Villa, E. S. Ali, U. Sahu, I. Ben-Sahra, Cancer Cells Tune the Signaling Pathways to Empower de Novo Synthesis of Nucleotides. *Cancers* (*Basel*) 11, (2019).
17. W. Li et al., MAGeCK enables robust identification of essential genes from genome-scale CRISPR/Cas9 knockout screens. *Genome Biol* 15, 554 (2014).

18. W. Li et al., Quality control, modeling, and visualization of CRISPR screens with MAGeCK-VISPR. *Genome Biol* 16, 281 (2015).
19. C. Jang, L. Chen, J. D. Rabinowitz, Metabolomics and Isotope Tracing. *Cell* 173, 822-837 (2018).
20. R. Rickels et al., Histone H3K4 monomethylation catalyzed by Trr and mammalian COMPASS-like proteins at enhancers is dispensable for development and viability. *Nat Genet* 49, 1647-1653 (2017).
21. R. J. DeBerardinis, N. S. Chandel, We need to talk about the Warburg effect. *Nat Metab* 2, 127-129 (2020).
22. A. R. J. Lawson et al., Extensive heterogeneity in somatic mutation and selection in the human bladder. *Science* 370, 75-82 (2020).
23. G. Wang et al., CRISPR-GEMM Pooled Mutagenic Screening Identifies KMT2D as a Major Modulator of Immune Checkpoint Blockade. *Cancer Discov* 10, 1912-1933 (2020).
24. D. Fantini et al., A Carcinogen-induced mouse model recapitulates the molecular alterations of human muscle invasive bladder cancer. *Oncogene* 37, 1911-1925 (2018).
25. M. A. Morgan, A. Shilatifard, Chromatin signatures of cancer. *Gene Dev* 29, 238-249 (2015).
26. L. Wang et al., Resetting the epigenetic balance of Polycomb and COMPASS function at enhancers for cancer therapy. *Nat Med* 24, 758-769 (2018).
27. Y. Gui et al., Frequent mutations of chromatin remodeling genes in transitional cell carcinoma of the bladder. *Nat Genet* 43, 875-878 (2011).
28. R. Li et al., Macroscopic somatic clonal expansion in morphologically normal human urothelium. *Science* 370, 82-89 (2020).
29. C. S. Grasso et al., The mutational landscape of lethal castration-resistant prostate cancer. *Nature* 487, 239-243 (2012).
30. D. W. Parsons et al., The genetic landscape of the childhood cancer medulloblastoma. *Science* 331, 435-439 (2011).
31. D. T. Jones et al., Dissecting the genomic complexity underlying medulloblastoma. *Nature* 488, 100-105 (2012).
32. T. J. Pugh et al., Medulloblastoma exome sequencing uncovers subtype-specific somatic mutations. *Nature* 488, 106-110 (2012).
33. J. Zhang et al., Disruption of KMT2D perturbs germinal center B cell development and promotes lymphomagenesis. *Nat Med* 21, 1190-1198 (2015).
34. R. D. Morin et al., Frequent mutation of histone-modifying genes in non-Hodgkin lymphoma. *Nature* 476, 298-303 (2011).
35. L. Pasqualucci et al., Analysis of the coding genome of diffuse large B-cell lymphoma. *Nat Genet* 43, 830-837 (2011).
36. J. G. Lohr et al., Discovery and prioritization of somatic mutations in diffuse large B-cell lymphoma (DLBCL) by whole-exome sequencing. *Proc Natl Acad Sci USA* 109, 3879-3884 (2012).
37. I. Martincorena et al., Somatic mutant clones colonize the human esophagus with age. *Science* 362, 911-917 (2018).
38. A. Yokoyama et al., Age-related remodelling of oesophageal epithelia by mutated cancer drivers. *Nature* 565, 312-317 (2019).
39. L. Moore et al., The mutational landscape of normal human endometrial epithelium. *Nature* 580, 640-646 (2020).
K. Yizhak et al., RNA sequence analysis reveals macroscopic somatic clonal expansion across normal tissues. *Science* 364, (2019).
41. Y. L. Liu et al., Structural insights into trans-histone regulation of H3K4 methylation by unique histone H4 binding of MLL3/4. *Nature Communications* 10, (2019).
42. H. Alam et al., KMT2D Deficiency Impairs Super-Enhancers to Confer a Glycolytic Vulnerability in Lung Cancer. *Cancer Cell* 37, 599-617 e597 (2020).
43. M. Maitituoheti et al., Enhancer Reprogramming Confers Dependence on Glycolysis and IGF Signaling in KMT2D Mutant Melanoma. *Cell Rep* 33, 108293 (2020).
44. C. Pacelli et al., Loss of Function of the Gene Encoding the Histone Methyltransferase KMT2D Leads to Deregulation of Mitochondrial Respiration. *Cells* 9, (2020).
45. N. N. Kalu et al., Comprehensive pharmacogenomic profiling of human papillomavirus-positive and -negative squamous cell carcinoma identifies sensitivity to aurora kinase inhibition in KMT2D mutants. *Cancer Lett* 431, 64-72 (2018).
46. M. G. Vander Heiden, R. J. DeBerardinis, Understanding the Intersections between Metabolism and Cancer Biology. *Cell* 168, 657-669 (2017).
47. Z. E. Stine, Z. T. Schug, J. M. Salvino, C. V. Dang, Targeting cancer metabolism in the era of precision oncology. *Nat Rev Drug Discov* 21, 141-162 (2022).
48. Z. Zhao et al., Systematic analyses of the cytotoxic effects of compound 11a, a putative synthetic agonist of photoreceptor-specific nuclear receptor (PNR), in cancer cell lines. *PloS one* 8, e75198 (2013).
49. J. G. Doench et al., Optimized sgRNA design to maximize activity and minimize off-target effects of CRISPR-Cas9. *Nat Biotechnol* 34, 184-191 (2016).
50. B. Wang et al., Integrative analysis of pooled CRISPR genetic screens using MAGeCKFlute. *Nat Protoc* 14, 756-780 (2019).
51. S. Andrews, FastQC: a quality control tool for high throughput sequence data. Available online. (2010).
52. A. M. Bolger, M. Lohse, B. Usadel, Trimmomatic: a flexible trimmer for Illumina sequence data. *Bioinformatics* 30, 2114-2120 (2014).
53. D. Kim et al., TopHat2: accurate alignment of transcriptomes in the presence of insertions, deletions and gene fusions. *Genome biology* 14, R36 (2013).
54. B. Langmead, C. Trapnell, M. Pop, S. L. Salzberg, Ultrafast and memory-efficient alignment of short DNA sequences to the human genome. *Genome biology* 10, R25 (2009).
55. M. Lawrence et al., Software for computing and annotating genomic ranges. *PLoS computational biology* 9, e1003118 (2013).
56. S. Anders, P. T. Pyl, W. Huber, HTSeq—a Python framework to work with high-throughput sequencing data. *Bioinformatics* 31, 166-169 (2015).
57. M. D. Robinson, D. J. McCarthy, G. K. Smyth, edgeR: a Bioconductor package for differential expression analysis of digital gene expression data. *Bioinformatics* 26, 139-140 (2010).
58. Y. Zhang, G. Parmigiani, W. E. Johnson, ComBat-seq: batch effect adjustment for RNA-seq count data. *NAR Genom Bioinform* 2, 1qaa078 (2020).
59. Y. Zhou et al., Metascape provides a biologist-oriented resource for the analysis of systems-level datasets. *Nat Commun* 10, 1523 (2019).
60. A. P. Szczepanski et al., ASXL3 bridges BRD4 to BAP1 complex and governs enhancer activity in small cell lung cancer. *Genome Med* 12, 63 (2020).

61. Y. Zhang et al., Model-based analysis of ChIP-Seq (MACS). *Genome Biol* 9, R137 (2008).
62. G. Yu, L. G. Wang, Q. Y. He, ChIPseeker: an R/Bioconductor package for ChIP peak annotation, comparison and visualization. *Bioinformatics* 31, 2382-2383 (2015).
63. L. Shen, N. Shao, X. Liu, E. Nestler, ngs.plot: Quick mining and visualization of next-generation sequencing data by integrating genomic databases. *BMC Genomics* 15, 284 (2014).
64. A. R. Quinlan, I. M. Hall, BEDTools: a flexible suite of utilities for comparing genomic features. *Bioinformatics* 26, 841-842 (2010).
65. R. Hashizume et al., Pharmacologic inhibition of histone demethylation as a therapy for pediatric brainstem glioma. *Nat Med* 20, 1394-1396 (2014).
66. J. H. Gibcus et al., A pathway for mitotic chromosome formation. *Science* 359, (2018).

Example 2: The Application of Lometrexol for MLL4 Mutated Cancers Using BBN Bladder Cancer Mouse Model Background: In our previous study, we aimed to explore the sensitivity of tumor cells with MLL3/MLL4/UTX-COMPASS mutations to lometrexol, an inhibitor targeting de novo purine synthesis. To achieve this, we used a variety of cell line-based systems, including wild type and MLL3/4 knockout isogenic mouse embryonic stem cells, multiple cancer cell lines with MLL4 wild type or mutant genotypes, and CRISPR correction knock-in isogenic human cancer cell lines. Our results showed that MLL4 mutant tumor cells are highly sensitive to lometrexol. We also observed the same phenomenon in xenograft mouse models of colorectal cancer, using MLL4 wild type and mutant cell lines. Overall, our findings suggest that lometrexol could be an effective treatment for tumors with MLL3/MLL4/UTX-COMPASS mutations.

N-butyl-N-(4-hydroxybutyl)-nitrosamine (BBN) is a carcinogen, that mimics the tobacco use in human. When administered to C57/B6 male mice in drinking water for at least 20 weeks, causes muscle invasive bladder tumors (MIBC) (1). Besides, 70% of Kmt2d/MLL4 is mutated in BBN mouse model, mimicking high MLL4 mutation rate (and low UTX mutation rate) found in colorectal cancer (1, 2). Thus, we believe that this is a valuable system where we could examine the effect of lometrexol in bladder cancer based on the MLL4 mutation stratification.

Hypothesis: Our hypothesis is that tumors with MLL4 mutations may be more responsive to treatment with lometrexol in BBN induced bladder cancer mouse model.

Experiment design: Thirty 7-week-old C57BL/6J male mice were used in our study to induce bladder cancer by feeding them with 0.1% BBN containing water for 6 weeks. The mice were then randomized into two groups: DMSO (n=15) or lometrexol treatment (n=15) and were given intraperitoneal injections of the respective treatments twice a week at a dose of 15 mg/kg for 12 weeks. At the end of the treatment period, the bladder tissues of the mice were harvested for H&E staining and RNA isolation. Each mouse's tumor grade was assessed, and RNA samples were analyzed for mutations in the kmt2d/MLL4 gene through mRNA-seq. Finally, we compared the MLL4 genotype and treatment to the tumor stage to assess the effectiveness of the treatment.

Figure 21:
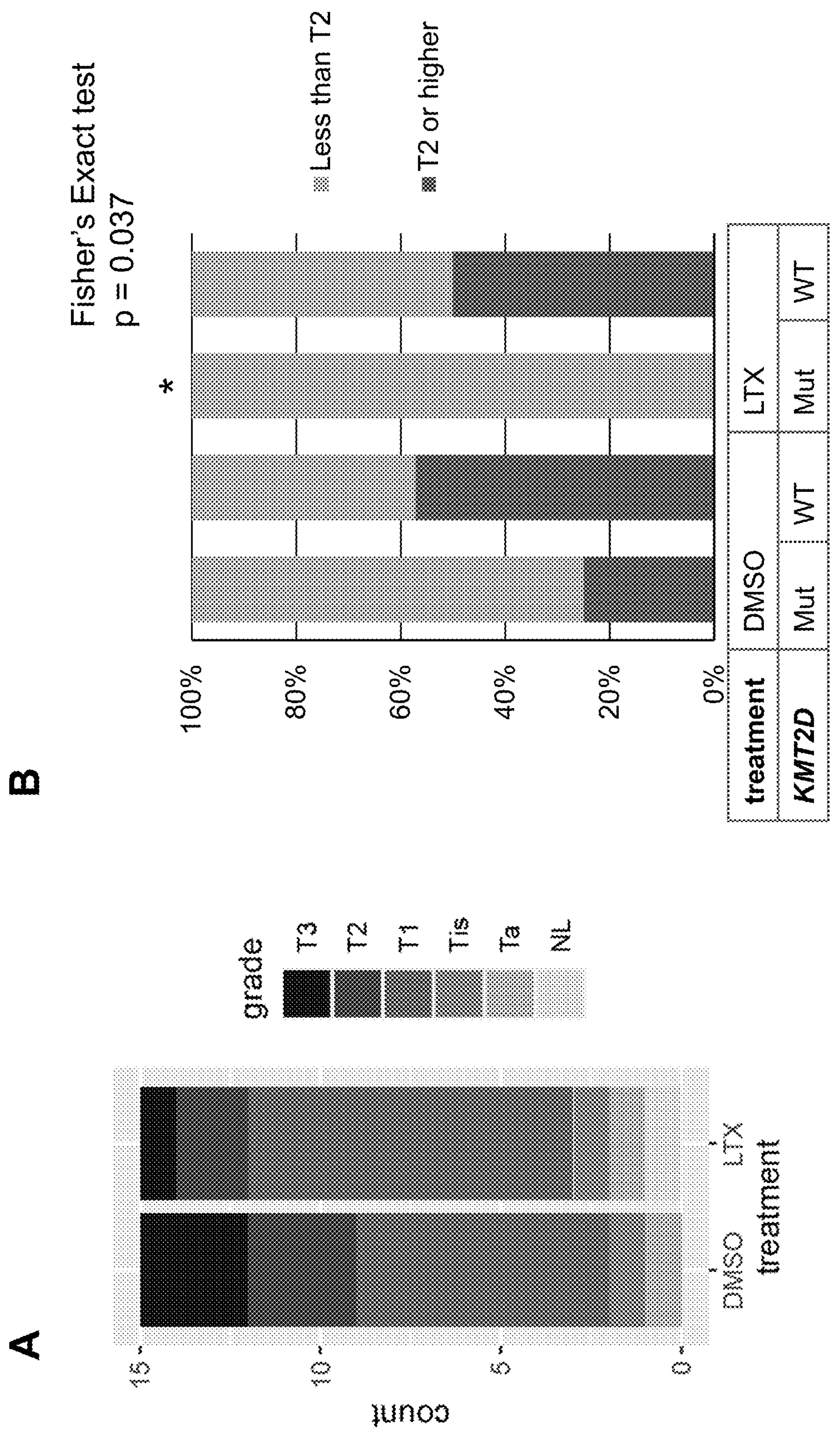
FIG. 21. MLL4 mutation as a biomarker for predicting sensitivity to metabolic inhibition. (A) Tumor grade classification in DMSO and LTX treated group. (B) A classification of tumor grade classification in DMSO and LTX treated group stratified based on MLL4 mutation status.

Results: The mice with MLL4 mutant tumors receiving lometrexol treatment has significant lowered tumor stages compared with other groups (Fisher's exact test, p=0.037) (FIG. 21A, B).

Discussion: Our results in BBN bladder cancer mouse model bucket trial revealed MLL4 mutation within COMPASS is a reliable stratification marker for lometrexol sensitivity, depicting a targetable metabolic dependency arising from epigenetic factor deficiency. Our study further provides insight to inform therapy for cancers with epigenetic alterations secondary to MLL3/4 COMPASS dysfunction.

REFERENCES

1. D. Fantini, J. J. Meeks, The BBN model: a mouse bladder cancer model featuring basal-subtype gene expression and MLL3/MLL4 genetic disruption. *Oncoscience* 5, 172-173 (2018).
2. D. Fantini et al., A Carcinogen-induced mouse model recapitulates the molecular alterations of human muscle invasive bladder cancer. *Oncogene* 37, 1911-1925 (2018).

What is claimed:

1. A method for treatment of a subject having a MLL3/4 COMPASS deficient cancer, the method comprising administering to the subject an effective amount of a nucleotide synthesis inhibitor.

2. The method of claim 1, wherein the subject has a MLL3/4 loss of function mutation.

3. The method of claim 1, wherein the MLL3/4 COMPASS deficient cancer is a colorectal cancer, a breast cancer, a lung cancer, an esophageal cancer, a gastric cancer, a prostate cancer, a bladder cancer, a lymphoma, a leukemia or a medulloblastoma.

4. The method of claim 1, wherein the nucleotide synthesis inhibitor is a de novo purine synthesis inhibitor.

5. The method of claim 4, wherein the nucleotide synthesis inhibitor comprises a glycinamide ribonucleotide formyltransferase (GARFT) inhibitor, a phosphoribosyl pyrophosphate amidotransferase (PPAT) inhibitor, a phosphoribosylformylglycinamidine synthase (PFAS) inhibitor, phosphoribosylaminoimidazole succinocarboxamide synthetase (PAICS) inhibitor, an adenylosuccinate lyase (ADSL) inhibitor, an adenylosuccinate synthetase (AdSS) inhibitor, or a guanosine monophosphate synthetase (GMPS) inhibitor.

6. The method of claim 5, wherein the nucleotide synthesis inhibitor comprises lometrexol, methotrexate, or pelitrexol.

7. The method of claim 1, wherein the nucleotide synthesis inhibitor is a de novo pyrimidine synthesis inhibitor.

8. The method of claim 7, wherein the nucleotide synthesis inhibitor comprises a carbamoyl-phosphate synthetase 2, aspartate transcarbamoylase, and dihydroorotase (CAD) inhibitor; a dihydroorotate dehydrogenase (DHODH) inhibitor; or a Uridine 5'-monophosphate (UMPS) inhibitor.

9. The method of claim 8, wherein the nucleotide synthesis inhibitor comprises Brequinar or Leflunomide.

10. A method for treatment of a subject having a MLL3/4 loss of function mutation, the method comprising administering the subject an effective amount of a nucleotide synthesis inhibitor.

11. The method of claim 10, wherein subject has a cancer.

12. The method of claim 11, wherein the cancer is a colorectal cancer, a breast cancer, a lung cancer, an esophageal cancer, a gastric cancer, a prostate cancer, a bladder cancer, a lymphoma, a leukemia or a medulloblastoma.

13. The method of claim 10, wherein the nucleotide synthesis inhibitor is a de novo purine synthesis inhibitor.

14. The method of claim 13, wherein the nucleotide synthesis inhibitor comprises a glycinamide ribonucleotide formyltransferase (GARFT) inhibitor, a phosphoribosyl pyrophosphate amidotransferase (PPAT) inhibitor, a phosphoribosylformylglycinamidine synthase (PFAS) inhibitor, phosphoribosylaminoimidazole succinocarboxamide synthetase (PAICS) inhibitor, an adenylosuccinate lyase (ADSL) inhibitor, an adenylosuccinate synthetase (AdSS) inhibitor, or a guanosine monophosphate synthetase (GMPS) inhibitor.

15. The method of claim 14, wherein the nucleotide synthesis inhibitor comprises lometrexol, methotrexate, or pelitrexol.

16. The method of claim 10, wherein the nucleotide synthesis inhibitor is a de novo pyrimidine synthesis inhibitor.

17. The method of claim 16, wherein the nucleotide synthesis inhibitor comprises a carbamoyl-phosphate synthetase 2, aspartate transcarbamoylase, and dihydroorotase (CAD) inhibitor; a dihydroorotate dehydrogenase (DHODH) inhibitor; or a Uridine 5'-monophosphate (UMPS) inhibitor.

18. The method of claim 17, wherein the nucleotide synthesis inhibitor comprises Brequinar or Leflunomide.

19. A method for the treatment of a subject, the method comprising obtaining a sample from a subject; testing the sample for the presence of a biomarker for a MLL3/4 COMPASS deficient cancer; and administering an effective amount of a nucleotide synthesis inhibitor to the subject if the sample tests positive for the biomarker.

20. The method of claim 19, wherein the biomarker is a MLL3/4 loss of function mutation.

21. The method of claim 1, wherein the nucleotide synthesis inhibitor does not comprise methotrexate.

22. The method of claim 10, wherein the nucleotide synthesis inhibitor does not comprise methotrexate.

23. The method of claim 19, wherein the nucleotide synthesis inhibitor does not comprise methotrexate.

* * * * *

SEQUENCE LISTING

```
Sequence total quantity: 33
SEQ ID NO: 1           moltype = DNA  length = 20
FEATURE                Location/Qualifiers
source                 1..20
                       mol_type = other DNA
                       organism = synthetic construct
SEQUENCE: 1
tggggatgga cagcccgacg                                              20

SEQ ID NO: 2           moltype = DNA  length = 20
FEATURE                Location/Qualifiers
source                 1..20
                       mol_type = other DNA
                       organism = synthetic construct
SEQUENCE: 2
ggtataatca atccgtcctt                                              20

SEQ ID NO: 3           moltype = DNA  length = 20
FEATURE                Location/Qualifiers
source                 1..20
                       mol_type = other DNA
                       organism = synthetic construct
SEQUENCE: 3
catatgctgt aggaaccgta                                              20
```

-continued

```
SEQ ID NO: 4            moltype = DNA  length = 20
FEATURE                 Location/Qualifiers
source                  1..20
                        mol_type = other DNA
                        organism = synthetic construct
SEQUENCE: 4
ttgggacagg tacgaaaata                                              20

SEQ ID NO: 5            moltype = DNA  length = 58
FEATURE                 Location/Qualifiers
source                  1..58
                        mol_type = other DNA
                        organism = synthetic construct
SEQUENCE: 5
ccgggcagga acagaagttc gctatctcga gatagcgaac ttctgttcct gctttttg    58

SEQ ID NO: 6            moltype = DNA  length = 58
FEATURE                 Location/Qualifiers
source                  1..58
                        mol_type = other DNA
                        organism = synthetic construct
SEQUENCE: 6
ccggcctaga caacgacaag tacatctcga gatgtacttg tcgttgtcta ggtttttg    58

SEQ ID NO: 7            moltype = DNA  length = 58
FEATURE                 Location/Qualifiers
source                  1..58
                        mol_type = other DNA
                        organism = synthetic construct
SEQUENCE: 7
ccggcttcga ccaaaccgtt tctctctcga gagagaaacg gtttggtcga agtttttg    58

SEQ ID NO: 8            moltype = DNA  length = 58
FEATURE                 Location/Qualifiers
source                  1..58
                        mol_type = other DNA
                        organism = synthetic construct
SEQUENCE: 8
ccgggccttg ttgatctatc ttgtactcga gtacaagata gatcaacaag gctttttg    58

SEQ ID NO: 9            moltype = DNA  length = 58
FEATURE                 Location/Qualifiers
source                  1..58
                        mol_type = other DNA
                        organism = synthetic construct
SEQUENCE: 9
ccgggcctac taccatcatc gagaactcga gttctcgatg atggtagtag gctttttg    58

SEQ ID NO: 10           moltype = DNA  length = 58
FEATURE                 Location/Qualifiers
source                  1..58
                        mol_type = other DNA
                        organism = synthetic construct
SEQUENCE: 10
ccggagcaag cactaaggat caaagctcga gctttgatcc ttagtgcttg ctttttg     58

SEQ ID NO: 11           moltype = DNA  length = 58
FEATURE                 Location/Qualifiers
source                  1..58
                        mol_type = other DNA
                        organism = synthetic construct
SEQUENCE: 11
ccgggattcg agagacagag gtcatctcga gatgacctct gtctctcgaa tctttttg    58

SEQ ID NO: 12           moltype = DNA  length = 58
FEATURE                 Location/Qualifiers
source                  1..58
                        mol_type = other DNA
                        organism = synthetic construct
SEQUENCE: 12
ccggcgctta aatgccggag aagttctcga gaacttctcc ggcatttaag cgtttttg    58

SEQ ID NO: 13           moltype = DNA  length = 58
FEATURE                 Location/Qualifiers
source                  1..58
                        mol_type = other DNA
                        organism = synthetic construct
SEQUENCE: 13
```

```
ccgggccttt aatatggacc ctgttctcga gaacagggtc catattaaag gctttttg    58

SEQ ID NO: 14           moltype = DNA  length = 58
FEATURE                 Location/Qualifiers
source                  1..58
                        mol_type = other DNA
                        organism = synthetic construct
SEQUENCE: 14
ccggcttctg gatattcatg gacaactcga gttgtccatg aatatccaga agtttttg    58

SEQ ID NO: 15           moltype = DNA  length = 59
FEATURE                 Location/Qualifiers
source                  1..59
                        mol_type = other DNA
                        organism = synthetic construct
SEQUENCE: 15
ccggcctaga gtacagggtg aacatctcga gatgttcacc ctgtactcta ggtttttg   59

SEQ ID NO: 16           moltype = DNA  length = 59
FEATURE                 Location/Qualifiers
source                  1..59
                        mol_type = other DNA
                        organism = synthetic construct
SEQUENCE: 16
ccggggcgag ctgagatttg gatatctcga gatatccaaa tctcagctcg cctttttg   59

SEQ ID NO: 17           moltype = DNA  length = 59
FEATURE                 Location/Qualifiers
source                  1..59
                        mol_type = other DNA
                        organism = synthetic construct
SEQUENCE: 17
ccgggaagag aagtcttcgt caattctcga gaattgacga agacttctct tctttttg   59

SEQ ID NO: 18           moltype = DNA  length = 58
FEATURE                 Location/Qualifiers
source                  1..58
                        mol_type = other DNA
                        organism = synthetic construct
SEQUENCE: 18
ccggcgctaa tttgatcctg tgtttctcga gaaacacagg atcaaattag cgtttttg    58

SEQ ID NO: 19           moltype = DNA  length = 58
FEATURE                 Location/Qualifiers
source                  1..58
                        mol_type = other DNA
                        organism = synthetic construct
SEQUENCE: 19
ccggcgagac ccattggcaa tactactcga gtagtattgc caatgggtct cgtttttg    58

SEQ ID NO: 20           moltype = DNA  length = 58
FEATURE                 Location/Qualifiers
source                  1..58
                        mol_type = other DNA
                        organism = synthetic construct
SEQUENCE: 20
ccggcgggac gccttcgata ctcttctcga gaagagtatc gaaggcgtcc cgtttttg    58

SEQ ID NO: 21           moltype = DNA  length = 58
FEATURE                 Location/Qualifiers
source                  1..58
                        mol_type = other DNA
                        organism = synthetic construct
SEQUENCE: 21
ccgggctgac atacattgat gacaactcga gttgtcatca atgtatgtca gctttttg    58

SEQ ID NO: 22           moltype = DNA  length = 59
FEATURE                 Location/Qualifiers
source                  1..59
                        mol_type = other DNA
                        organism = synthetic construct
SEQUENCE: 22
ccggcacctt catgtctgca tatttctcga gaaatatgca gacatgaagg tgtttttg   59

SEQ ID NO: 23           moltype = DNA  length = 58
FEATURE                 Location/Qualifiers
source                  1..58
                        mol_type = other DNA
                        organism = synthetic construct
```

-continued

```
SEQUENCE: 23
ccggccagtg atgctgtaag tcattctcga gaatgactta cagcatcact ggtttttg    58

SEQ ID NO: 24          moltype = DNA  length = 21
FEATURE                Location/Qualifiers
source                 1..21
                       mol_type = other DNA
                       organism = synthetic construct
SEQUENCE: 24
ccctaactgt tgtcatggca a                                            21

SEQ ID NO: 25          moltype = DNA  length = 21
FEATURE                Location/Qualifiers
source                 1..21
                       mol_type = other DNA
                       organism = synthetic construct
SEQUENCE: 25
gcacagtctc atcatgtcaa a                                            21

SEQ ID NO: 26          moltype = DNA  length = 21
FEATURE                Location/Qualifiers
source                 1..21
                       mol_type = other DNA
                       organism = synthetic construct
SEQUENCE: 26
cgcagtgtga aatgattcca a                                            21

SEQ ID NO: 27          moltype = DNA  length = 21
FEATURE                Location/Qualifiers
source                 1..21
                       mol_type = other DNA
                       organism = synthetic construct
SEQUENCE: 27
gctgctcaga tatttgggtt a                                            21

SEQ ID NO: 28          moltype = DNA  length = 22
FEATURE                Location/Qualifiers
source                 1..22
                       mol_type = other DNA
                       organism = synthetic construct
SEQUENCE: 28
gcctgaaggg atgtggtatt ag                                           22

SEQ ID NO: 29          moltype = DNA  length = 22
FEATURE                Location/Qualifiers
source                 1..22
                       mol_type = other DNA
                       organism = synthetic construct
SEQUENCE: 29
cctgttaagg tagcagtgag tt                                           22

SEQ ID NO: 30          moltype = DNA  length = 22
FEATURE                Location/Qualifiers
source                 1..22
                       mol_type = other DNA
                       organism = synthetic construct
SEQUENCE: 30
gagaagagcc ctgattgtac tg                                           22

SEQ ID NO: 31          moltype = DNA  length = 20
FEATURE                Location/Qualifiers
source                 1..20
                       mol_type = other DNA
                       organism = synthetic construct
SEQUENCE: 31
acctcccatc ctctcttctt                                              20

SEQ ID NO: 32          moltype = DNA  length = 20
FEATURE                Location/Qualifiers
source                 1..20
                       mol_type = other DNA
                       organism = synthetic construct
```

-continued

```
SEQUENCE: 32
aacagcaact cccactcttc                                    20

SEQ ID NO: 33            moltype = DNA  length = 20
FEATURE                  Location/Qualifiers
source                   1..20
                         mol_type = other DNA
                         organism = synthetic construct
SEQUENCE: 33
cctgttgctg tagccgtatt                                    20
```